(12) United States Patent
Chern et al.

(10) Patent No.: US 8,415,482 B2
(45) Date of Patent: Apr. 9, 2013

(54) PROLINE DERIVATIVES

(75) Inventors: Jyh-Haur Chern, Taipei (TW); Yu-Sheng Chao, Monmouth Junction, NJ (US)

(73) Assignee: National Health Research Institutes, Zhunan Town, Miaoli County (TW)

( * ) Notice: Subject to any disclaimer, the term of this patent is extended or adjusted under 35 U.S.C. 154(b) by 78 days.

(21) Appl. No.: 12/958,734

(22) Filed: Dec. 2, 2010

(65) Prior Publication Data

US 2011/0136799 A1 Jun. 9, 2011

Related U.S. Application Data

(60) Provisional application No. 61/266,584, filed on Dec. 4, 2009.

(51) Int. Cl.
| | |
|---|---|
| C07D 277/30 | (2006.01) |
| C07D 413/00 | (2006.01) |
| C07D 401/00 | (2006.01) |
| C07D 417/14 | (2006.01) |
| A61K 31/535 | (2006.01) |
| A61K 31/445 | (2006.01) |
| A61K 31/44 | (2006.01) |

(52) U.S. Cl. .......... 548/204; 546/256; 546/187; 544/82; 514/229.2; 514/316; 514/333

(58) Field of Classification Search .................. 548/204; 544/82; 546/256, 187; 514/229.2, 316, 333
See application file for complete search history.

(56) References Cited

U.S. PATENT DOCUMENTS

| | | | |
|---|---|---|---|
| 2008/0050336 A1 | 2/2008 | Bachand et al. | |
| 2008/0311075 A1 * | 12/2008 | Bachand et al. | 424/85.2 |
| 2009/0043107 A1 | 2/2009 | Pack et al. | |

FOREIGN PATENT DOCUMENTS

| | | |
|---|---|---|
| WO | 2008/021928 | 2/2008 |
| WO | 2008/021936 | 2/2008 |
| WO | WO 2008021936 A2 * | 2/2008 |
| WO | WO 2008144380 A1 * | 11/2008 |

* cited by examiner

*Primary Examiner* — Joseph K. McKane
*Assistant Examiner* — Nyeemah A Grazier
(74) *Attorney, Agent, or Firm* — Occhiuti Rohlicek & Tsao LLP

(57) ABSTRACT

Compounds useful for treating hepatitis C virus infection. The compounds are of formula (I):

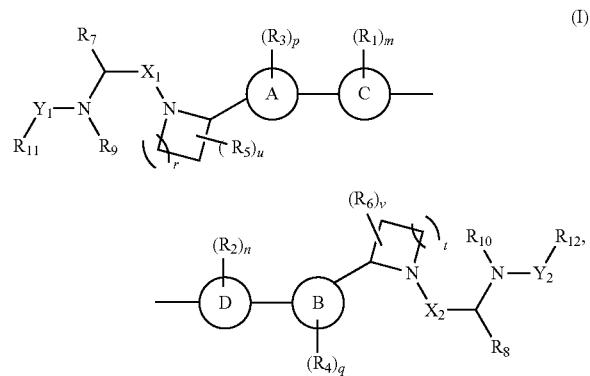

wherein A, B, C, D, $R_1$, $R_2$, $R_3$, $R_4$, $R_5$, $R_6$, $R_7$, $R_8$, $R_9$, $R_{10}$, $R_{11}$, $R_{12}$, m, n, p, q, r, t, u, and v are defined herein. Also disclosed is a method for treating hepatitis C virus infection with these compounds.

30 Claims, No Drawings

PROLINE DERIVATIVES

CROSS-REFERENCE TO RELATED APPLICATION

Pursuant to 35 U.S.C. §119(e), this application claims the benefit of the priority of U.S. Provisional Patent Application No. 61/266,584, filed Dec. 4, 2009. The content of the prior application is incorporated herein by its entirety.

BACKGROUND

Hepatitis C virus (HCV) infection is estimated to affect 170 million individuals worldwide. This disease is primarily transmitted through contaminated blood products. Although its spread has been slowed as a result of improvement in blood screening in many countries, it remains the leading cause of liver disease-related deaths in the world. For example, it causes about 10,000 deaths annually in the U.S. alone. In the absence of effective therapies, the death rate is expected to triple over the next 2 decades.

Current treatments based on interferon-alpha have low success rates, particularly for genotype-1 infections predominant in Europe, Japan, and the U.S. Also, they are expensive and poorly received by patients. Thus, there is a need to develop better therapeutic agents for treating HCV infection.

SUMMARY

This invention is based on the unexpected discovery that certain multicyclic compounds are effective in treating hepatitis C virus infection.

In one aspect, this invention relates to a compound of formula (I):

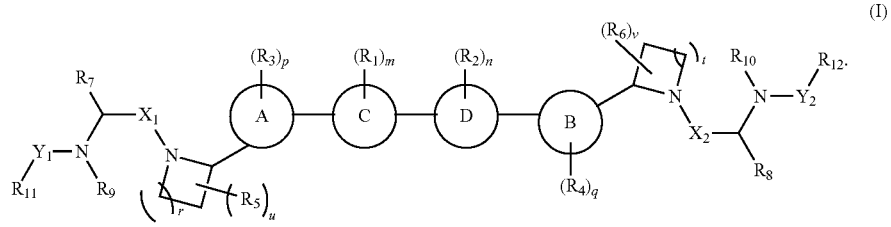

In formula (I), A is

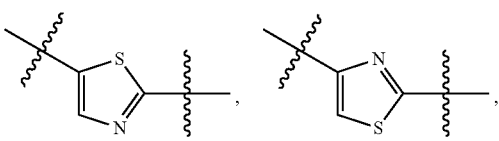

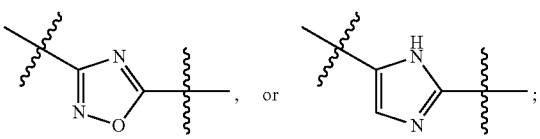

B is

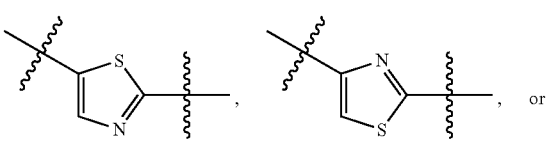

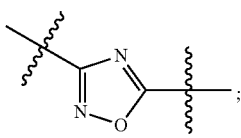

each of C and D, independently, is arylene or heteroarylene; each of $R_1$, $R_2$, $R_3$, $R_4$, $R_5$, and $R_6$, independently, is alkyl, alkenyl, alkynyl, aryl, heteroaryl, cycloalkyl, cycloalkenyl, heterocycloalkyl, halo, heterocycloalkenyl, cyano, or nitro; each of $R_7$ and $R_8$, independently, is H, alkyl, alkenyl, alkynyl, aryl, heteroaryl, cycloalkyl, cycloalkenyl, heterocycloalkyl, or heterocycloalkenyl; each of $R_9$ and $R_{10}$, independently, is H or alkyl; each of $R_{11}$ and $R_{12}$, independently, is H, alkyl, alkenyl, alkynyl, aryl, heteroaryl, cycloalkyl, cycloalkenyl, heterocycloalkyl, or heterocycloalkenyl; each of $X_1$ and $X_2$, independently, is C(O) or C(S); each of $Y_1$ and $Y_2$, independently, is deleted, SO, $SO_2$, C(O), C(O)O, C(O)$NR_a$, C(S)$NR_a$, or $SO_2NR_a$, in which $R_a$ is H, alkyl, cycloalkyl, heterocycloalkyl, aryl, or heteroaryl; each of m and n, independently, is 0, 1, 2, 3, or 4; each of p and q, independently, is 0 or 1; each of r and t, independently, is 1, 2, or 3; and each of u and v, independently, is 0, 1, 2, 3, 4, 5, 6, 7, or 8.

For example, the compounds of this invention are of formula (II) below:

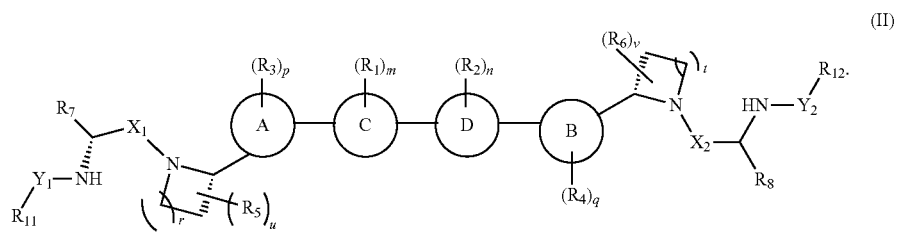

Particularly, they are of formula (III) below:

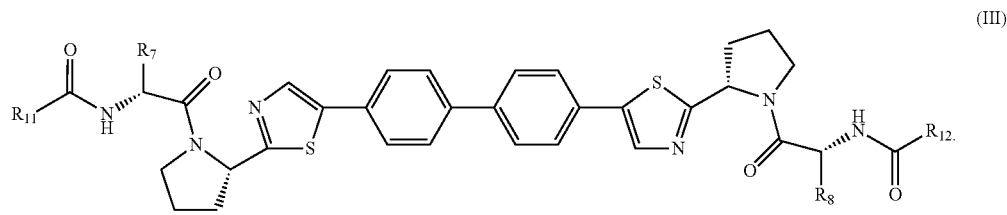

The above-described compounds may include one or more of the following features. Each of A and B is

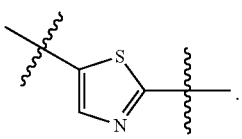

Each of C and D is phenylene. Each of $X_1$ and $X_2$ is C(O). Each of $Y_1$ and $Y_2$, independently, is $SO_2$, C(O), or C(O)O. Each of $R_7$ and $R_8$ is phenyl. Each of $R_{11}$ and $R_{12}$, independently, is $C_{1-5}$ alkyl or $C_{3-5}$ cycloalkyl. Each of t and r is 2. A and B are different. Each of p, m, n, q, u and v is 0. Each of p, m, n, and q is 0, each of u and v is 1, and each $R_5$ and $R_6$ is F.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, or 14-carbon tricyclic aromatic ring system. Examples of aryl groups include, but are not limited to, phenyl, naphthyl, and anthracenyl. The term "arylene" refers to a divalent 6-carbon monocyclic (e.g., phenylene), 10-carbon bicyclic (e.g., naphthylene), or 14-carbon tricyclic aromatic ring system. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a divalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, aryl, arylene, heteroaryl, and heteroarylene mentioned above include both substituted and unsubstituted moieties. Possible substituents on cycloalkyl, heterocycloalkyl, cycloalkenyl, heterocycloalkenyl, aryl, and heteroaryl include, but are not limited to, $C_1$-$C_{10}$ alkyl (e.g., trifluoromethyl), $C_2$-$C_{10}$ alkenyl, $C_2$-$C_{16}$ alkynyl (e.g., arylalkynyl), $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl (e.g., haloaryl or aryl substituted with halo), aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The multicyclic compounds described above include the compounds themselves, as well as their salts, their solvates, and their prodrugs, if applicable. A salt, for example, can be formed between an anion and a positively charged group (e.g., amino) on a multicyclic compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a multicyclic compound. Suitable cations include sodium ion, potassium ion, magnesium ion, calcium ion, and an ammonium cation such as tetramethylammonium ion. The multicyclic compounds also include those salts containing quaternary nitrogen atoms. Examples of prodrugs include esters and other pharmaceutically acceptable derivatives, which, upon administration to a subject, are capable of providing active multicyclic compounds.

In another aspect, this invention relates to a method for treating HCV infection by administering to a subject infected with HCV an effective amount of one or more of the multicyclic compounds described above.

Also within the scope of this invention is a pharmaceutical composition containing one or more of the above-described multicyclic compounds for use in treating HCV infection, as well as this therapeutic use and use of the compounds for the manufacture of a medicament for treating HCV infection.

The details of one or more embodiments of the invention are set forth in the description below. Other features, objects, and advantages of the invention will be apparent from the description and from the claims.

DETAILED DESCRIPTION

Shown in Table 1 below are exemplary compounds of this invention.

TABLE 1

| | Structure | $[M + H]^+$ |
|---|---|---|
| 6a | 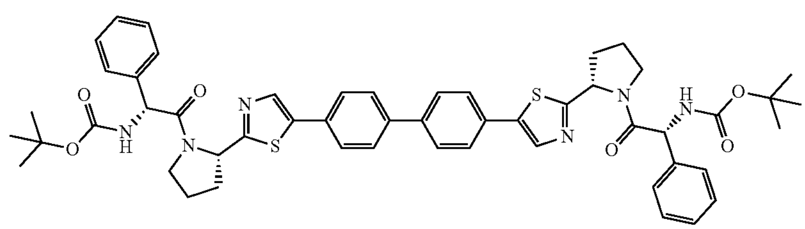 [SMILES: CC(C)(C)OC(=O)N[C@@H](C(=O)N1CCC[C@H]1c1ncc(-c2ccc(-c3ccc(-c4cnc([C@@H]5CCCN5C(=O)[C@H](NC(=O)OC(C)(C)C)c5ccccc5)s4)cc3)cc2)s1)c1ccccc1] | 925 |
| 7a-A | 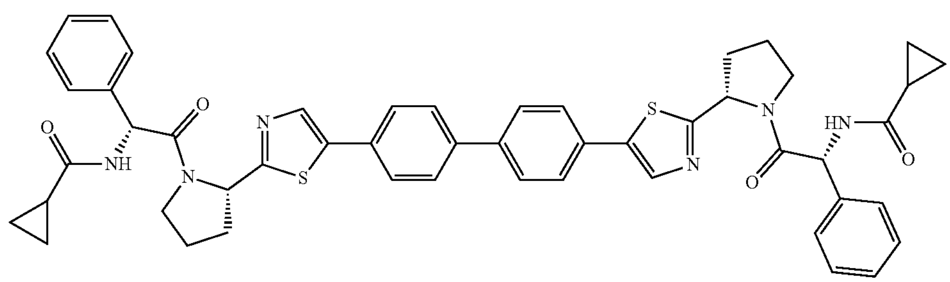 [SMILES: O=C(N[C@@H](C(=O)N1CCC[C@H]1c1ncc(-c2ccc(-c3ccc(-c4cnc([C@@H]5CCCN5C(=O)[C@H](NC(=O)C5CC5)c5ccccc5)s4)cc3)cc2)s1)c1ccccc1)C1CC1] | 861 |
| 7b-A | 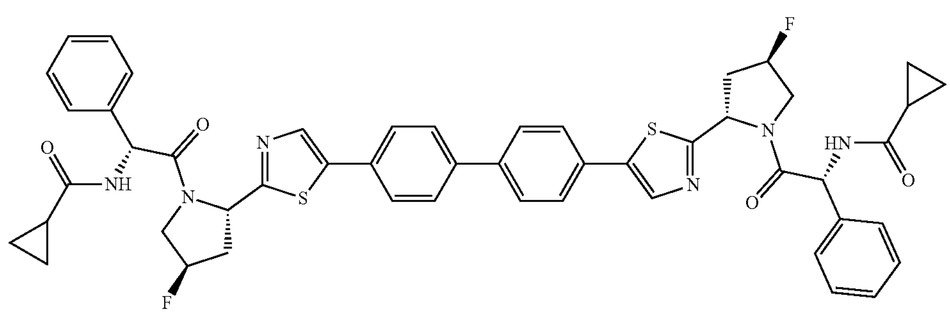 [SMILES: O=C(N[C@@H](C(=O)N1C[C@H](F)C[C@H]1c1ncc(-c2ccc(-c3ccc(-c4cnc([C@@H]5C[C@@H](F)CN5C(=O)[C@H](NC(=O)C5CC5)c5ccccc5)s4)cc3)cc2)s1)c1ccccc1)C1CC1] | 897 |

TABLE 1-continued

| | Structure | [M + H]+ |
|---|---|---|
| 7c-A | 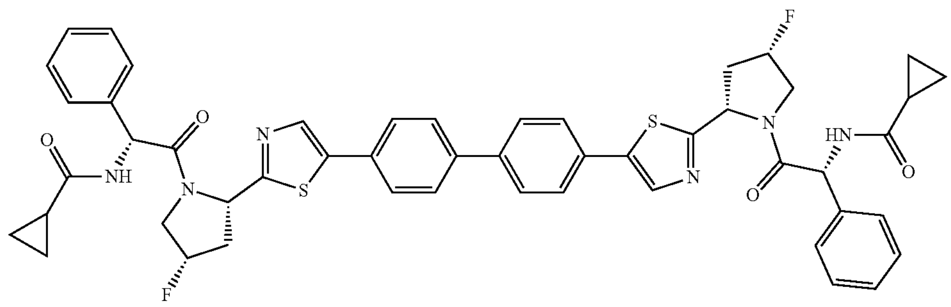 [SMILES: O=C(N[C@@H](C(=O)N1C[C@@H](F)C[C@H]1c1ncc(-c2ccc(-c3ccc(-c4cnc([C@@H]5C[C@H](F)CN5C(=O)[C@H](NC(=O)C5CC5)c5ccccc5)s4)cc3)cc2)s1)c1ccccc1)C1CC1] | 897 |
| 7a-B | 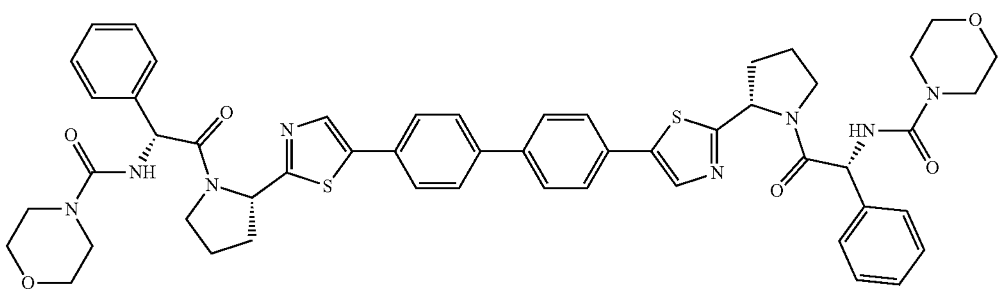 [SMILES: O=C(N[C@@H](C(=O)N1CCC[C@H]1c1ncc(-c2ccc(-c3ccc(-c4cnc([C@@H]5CCCN5C(=O)[C@H](NC(=O)N5CCOCC5)c5ccccc5)s4)cc3)cc2)s1)c1ccccc1)N1CCOCC1] | 951 |
| 7b-B | 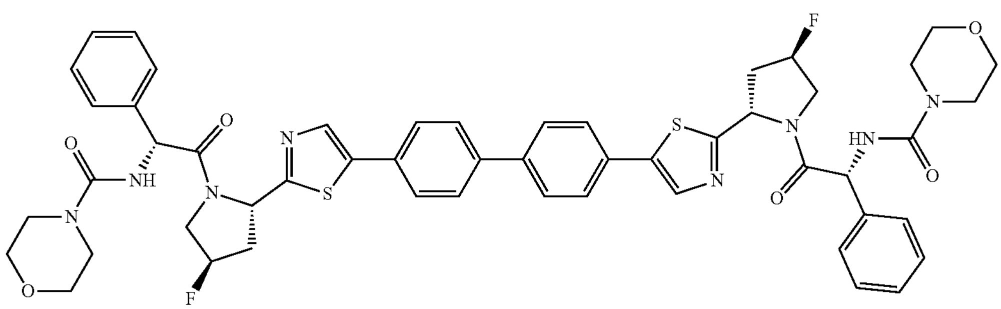 [SMILES: O=C(N[C@@H](C(=O)N1C[C@H](F)C[C@H]1c1ncc(-c2ccc(-c3ccc(-c4cnc([C@@H]5C[C@@H](F)CN5C(=O)[C@H](NC(=O)N5CCOCC5)c5ccccc5)s4)cc3)cc2)s1)c1ccccc1)N1CCOCC1] | 987 |
| 7c-B | 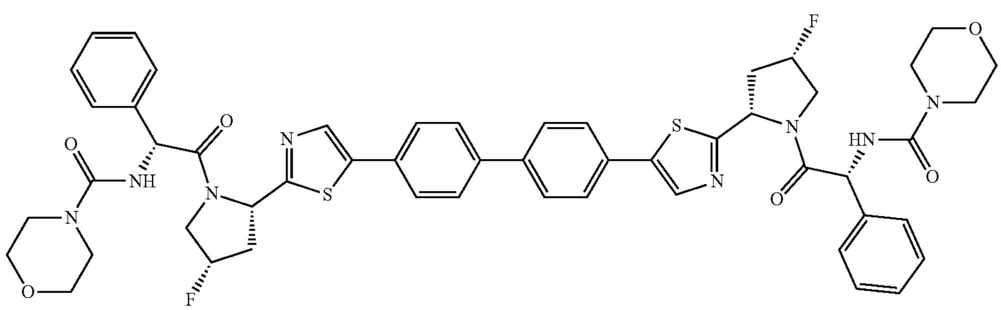 [SMILES: O=C(N[C@@H](C(=O)N1C[C@@H](F)C[C@H]1c1ncc(-c2ccc(-c3ccc(-c4cnc([C@@H]5C[C@H](F)CN5C(=O)[C@H](NC(=O)N5CCOCC5)c5ccccc5)s4)cc3)cc2)s1)c1ccccc1)N1CCOCC1] | 987 |
| 25a | 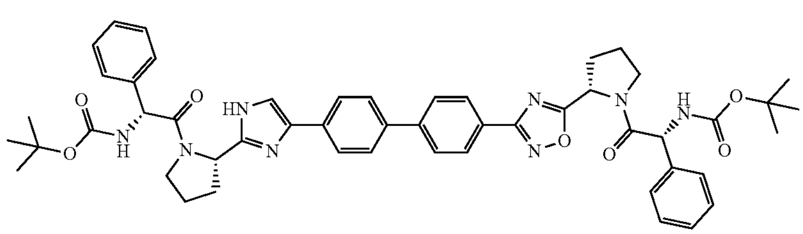 [SMILES: CC(C)(C)OC(=O)N[C@@H](C(=O)N1CCC[C@H]1c1nc(-c2ccc(-c3ccc(-c4noc([C@@H]5CCCN5C(=O)[C@H](NC(=O)OC(C)(C)C)c5ccccc5)n4)cc3)cc2)c[nH]1)c1ccccc1] | 893 |

TABLE 1-continued

| | Structure | [M + H]+ |
|---|---|---|
| 26a | 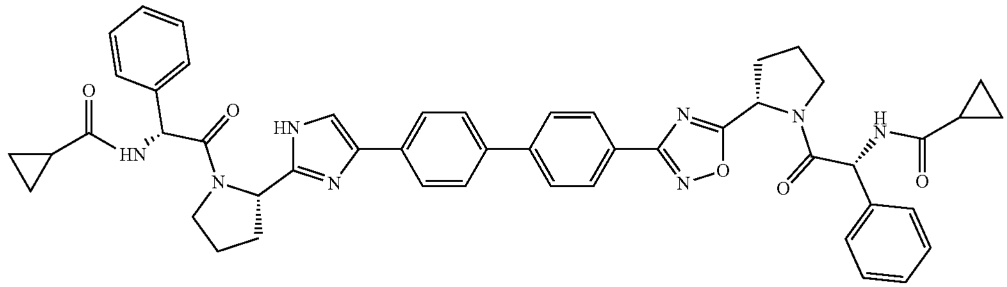 [SMILES: O=C(N[C@@H](C(=O)N1CCC[C@H]1c1nc(-c2ccc(-c3ccc(-c4noc([C@@H]5CCCN5C(=O)[C@H](NC(=O)C5CC5)c5ccccc5)n4)cc3)cc2)c[nH]1)c1ccccc1)C1CC1] | 829 |
| 29a | 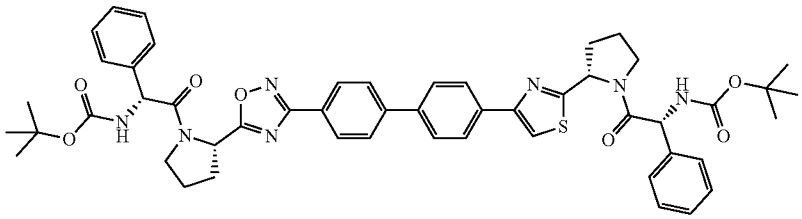 [SMILES: CC(C)(C)OC(=O)N[C@@H](C(=O)N1CCC[C@H]1c1nc(-c2ccc(-c3ccc(-c4csc([C@@H]5CCCN5C(=O)[C@H](NC(=O)OC(C)(C)C)c5ccccc5)n4)cc3)cc2)no1)c1ccccc1] | 910 |
| 30a | 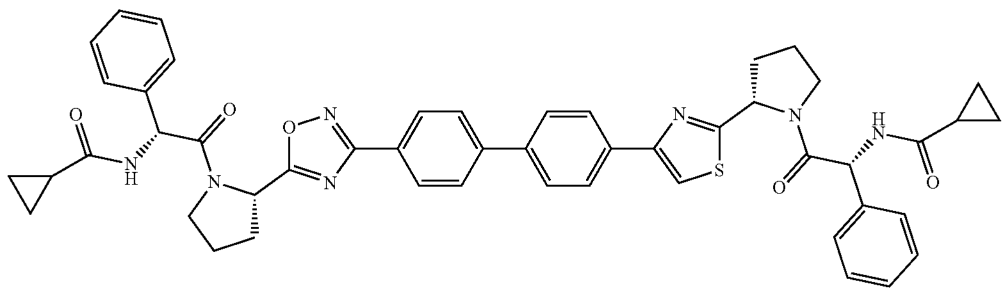 [SMILES: O=C(N[C@@H](C(=O)N1CCC[C@H]1c1nc(-c2ccc(-c3ccc(-c4csc([C@@H]5CCCN5C(=O)[C@H](NC(=O)C5CC5)c5ccccc5)n4)cc3)cc2)no1)c1ccccc1)C1CC1] | 846 |
| 33a | 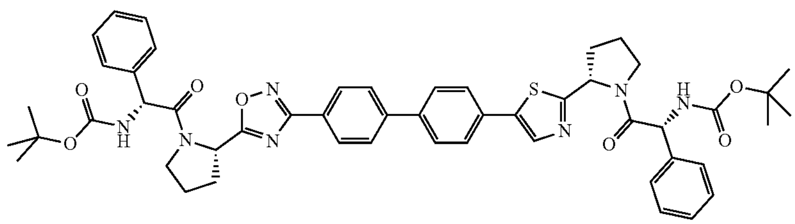 [SMILES: CC(C)(C)OC(=O)N[C@@H](C(=O)N1CCC[C@H]1c1nc(-c2ccc(-c3ccc(-c4cnc([C@@H]5CCCN5C(=O)[C@H](NC(=O)OC(C)(C)C)c5ccccc5)s4)cc3)cc2)no1)c1ccccc1] | 910 |
| 34a | 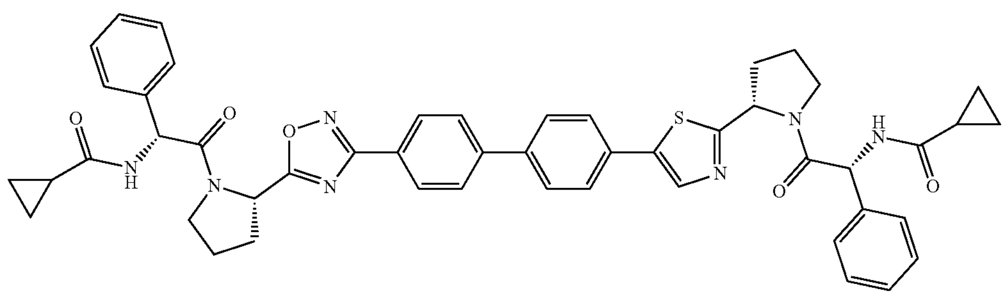 [SMILES: O=C(N[C@@H](C(=O)N1CCC[C@H]1c1nc(-c2ccc(-c3ccc(-c4cnc([C@@H]5CCCN5C(=O)[C@H](NC(=O)C5CC5)c5ccccc5)s4)cc3)cc2)no1)c1ccccc1)C1CC1] | 846 |
| 37a | 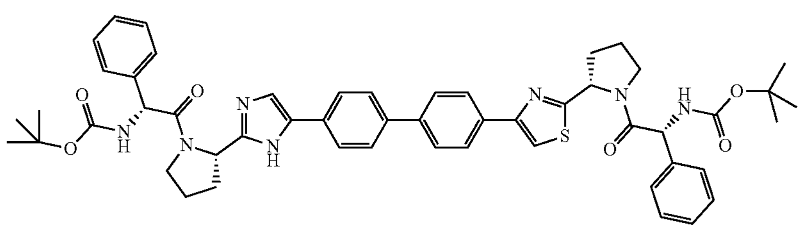 [SMILES: CC(C)(C)OC(=O)N[C@@H](C(=O)N1CCC[C@H]1c1ncc(-c2ccc(-c3ccc(-c4csc([C@@H]5CCCN5C(=O)[C@H](NC(=O)OC(C)(C)C)c5ccccc5)n4)cc3)cc2)[nH]1)c1ccccc1] | 908 |

TABLE 1-continued

| | Structure | [M + H]+ |
|---|---|---|
| 38a | 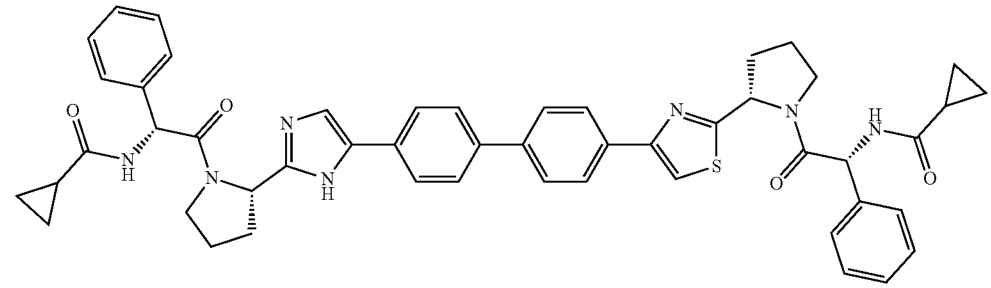 [SMILES: O=C(N[C@@H](C(=O)N1CCC[C@H]1c1ncc(-c2ccc(-c3ccc(-c4csc([C@@H]5CCCN5C(=O)[C@H](NC(=O)C5CC5)c5ccccc5)n4)cc3)cc2)[nH]1)c1ccccc1)C1CC1] | 844 |
| 41a | 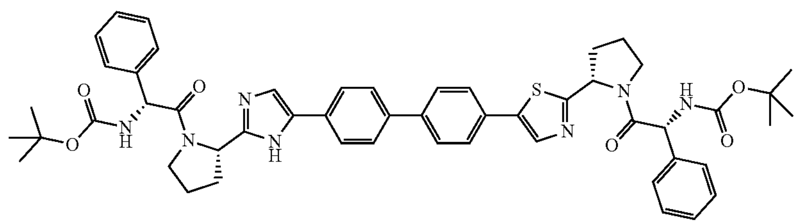 [SMILES: CC(C)(C)OC(=O)N[C@@H](C(=O)N1CCC[C@H]1c1ncc(-c2ccc(-c3ccc(-c4cnc([C@@H]5CCCN5C(=O)[C@H](NC(=O)OC(C)(C)C)c5ccccc5)s4)cc3)cc2)[nH]1)c1ccccc1] | 908 |
| 42a | 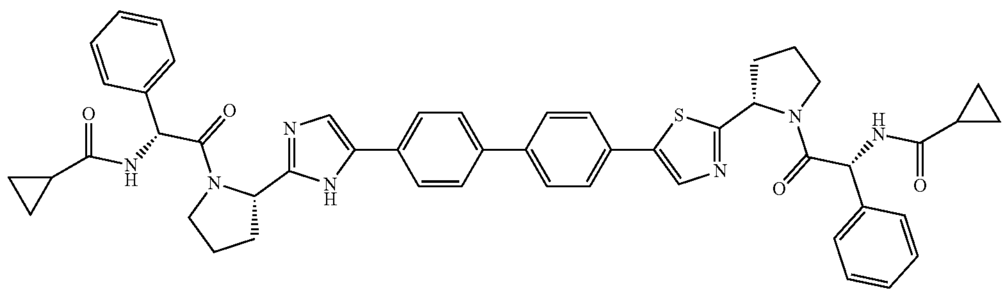 [SMILES: O=C(N[C@@H](C(=O)N1CCC[C@H]1c1ncc(-c2ccc(-c3ccc(-c4cnc([C@@H]5CCCN5C(=O)[C@H](NC(=O)C5CC5)c5ccccc5)s4)cc3)cc2)[nH]1)c1ccccc1)C1CC1] | 844 |
| 45a | 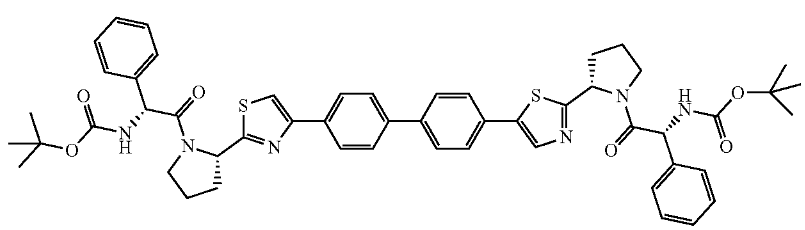 [SMILES: CC(C)(C)OC(=O)N[C@@H](C(=O)N1CCC[C@H]1c1nc(-c2ccc(-c3ccc(-c4cnc([C@@H]5CCCN5C(=O)[C@H](NC(=O)OC(C)(C)C)c5ccccc5)s4)cc3)cc2)cs1)c1ccccc1] | 925 |
| 46a | 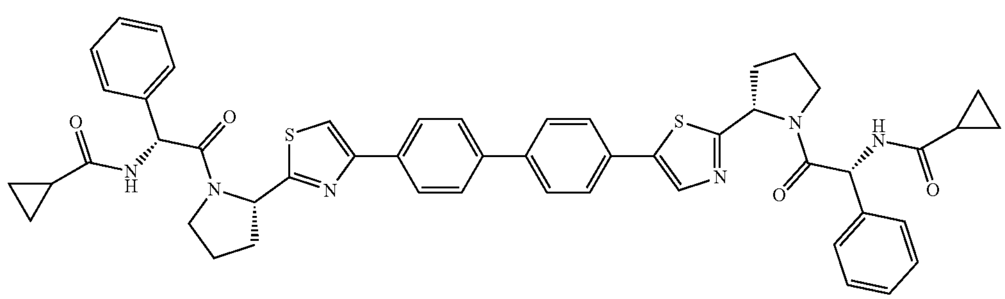 [SMILES: O=C(N[C@@H](C(=O)N1CCC[C@H]1c1nc(-c2ccc(-c3ccc(-c4cnc([C@@H]5CCCN5C(=O)[C@H](NC(=O)C5CC5)c5ccccc5)s4)cc3)cc2)cs1)c1ccccc1)C1CC1] | 861 |

TABLE 1-continued

| | Structure | [M + H]+ |
|---|---|---|
| 50a | 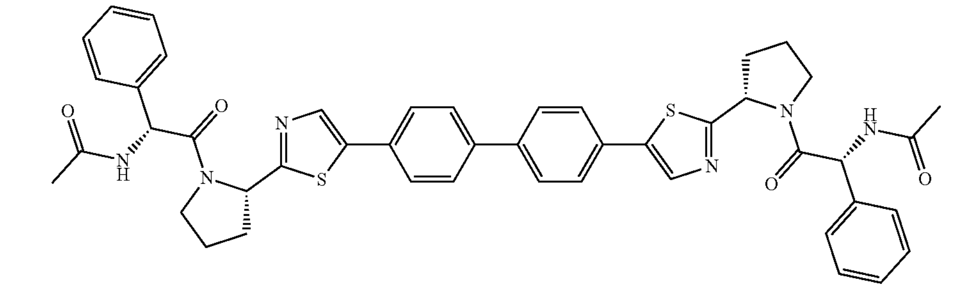 [SMILES: CC(=O)N[C@@H](C(=O)N1CCC[C@H]1c1ncc(-c2ccc(-c3ccc(-c4cnc([C@@H]5CCCN5C(=O)[C@H](NC(C)=O)c5ccccc5)s4)cc3)cc2)s1)c1ccccc1] | 809 |
| 51a | 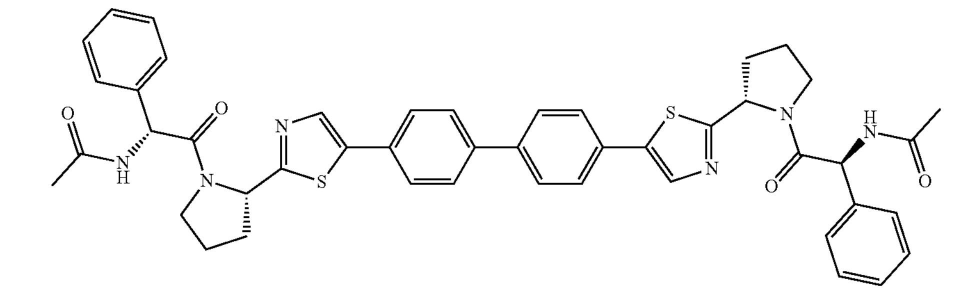 [SMILES: CC(=O)N[C@H](C(=O)N1CCC[C@H]1c1ncc(-c2ccc(-c3ccc(-c4cnc([C@@H]5CCCN5C(=O)[C@H](NC(C)=O)c5ccccc5)s4)cc3)cc2)s1)c1ccccc1] | 809 |
| 52a | 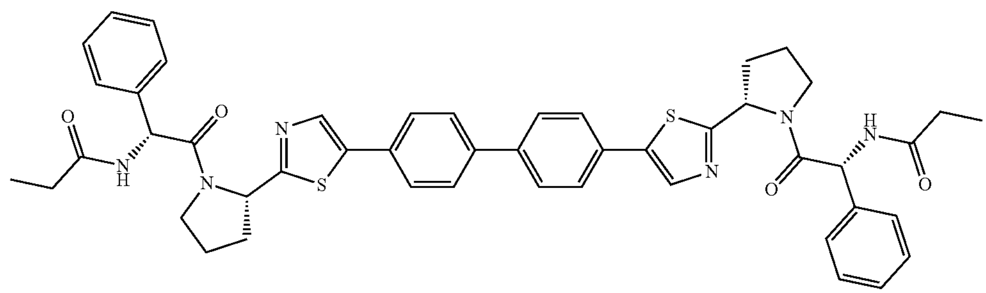 [SMILES: CCC(=O)N[C@@H](C(=O)N1CCC[C@H]1c1ncc(-c2ccc(-c3ccc(-c4cnc([C@@H]5CCCN5C(=O)[C@H](NC(=O)CC)c5ccccc5)s4)cc3)cc2)s1)c1ccccc1] | 837 |
| 53a | 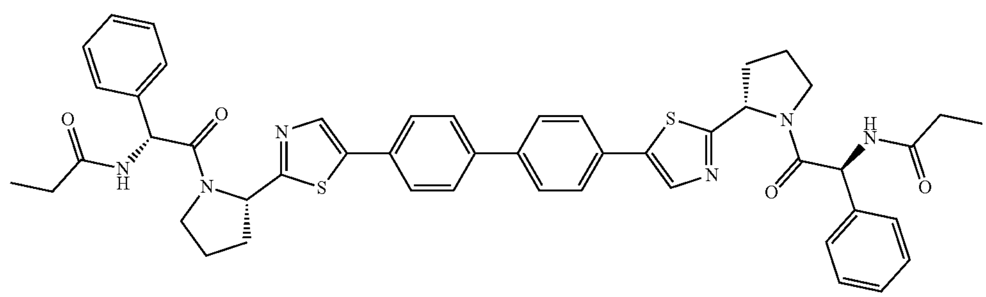 [SMILES: CCC(=O)N[C@H](C(=O)N1CCC[C@H]1c1ncc(-c2ccc(-c3ccc(-c4cnc([C@@H]5CCCN5C(=O)[C@H](NC(=O)CC)c5ccccc5)s4)cc3)cc2)s1)c1ccccc1] | 837 |
| 54a | 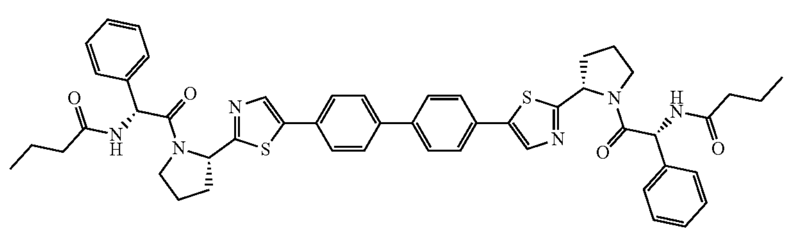 [SMILES: CCCC(=O)N[C@@H](C(=O)N1CCC[C@H]1c1ncc(-c2ccc(-c3ccc(-c4cnc([C@@H]5CCCN5C(=O)[C@H](NC(=O)CCC)c5ccccc5)s4)cc3)cc2)s1)c1ccccc1] | 865 |

TABLE 1-continued

| | Structure | [M + H]+ |
|---|---|---|
| 55a | 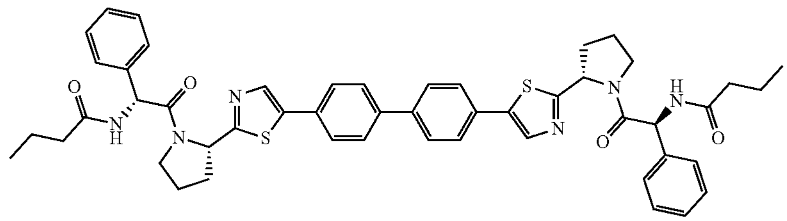 [SMILES: CCCC(=O)N[C@H](C(=O)N1CCC[C@H]1c1ncc(-c2ccc(-c3ccc(-c4cnc([C@@H]5CCCN5C(=O)[C@H](NC(=O)CCC)c5ccccc5)s4)cc3)cc2)s1)c1ccccc1] | 865 |
| 56a | 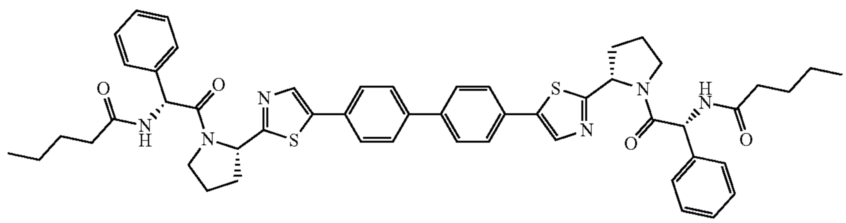 [SMILES: CCCCC(=O)N[C@@H](C(=O)N1CCC[C@H]1c1ncc(-c2ccc(-c3ccc(-c4cnc([C@@H]5CCCN5C(=O)[C@H](NC(=O)CCCC)c5ccccc5)s4)cc3)cc2)s1)c1ccccc1] | 893 |
| 57a | 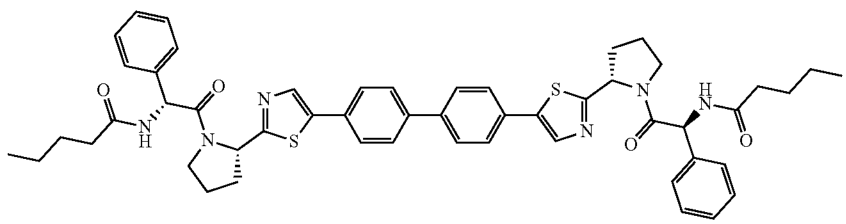 [SMILES: CCCCC(=O)N[C@H](C(=O)N1CCC[C@H]1c1ncc(-c2ccc(-c3ccc(-c4cnc([C@@H]5CCCN5C(=O)[C@H](NC(=O)CCCC)c5ccccc5)s4)cc3)cc2)s1)c1ccccc1] | 893 |
| 58a | 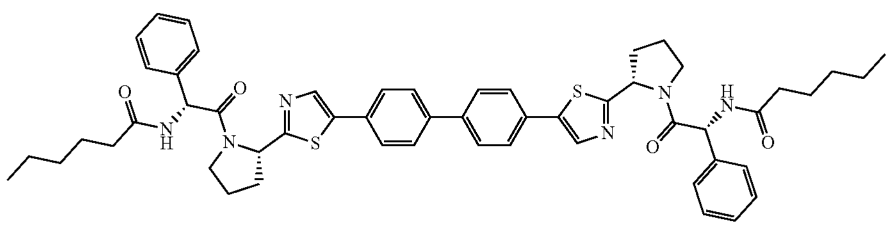 [SMILES: CCCCCC(=O)N[C@@H](C(=O)N1CCC[C@H]1c1ncc(-c2ccc(-c3ccc(-c4cnc([C@@H]5CCCN5C(=O)[C@H](NC(=O)CCCCC)c5ccccc5)s4)cc3)cc2)s1)c1ccccc1] | 921 |
| 59a | 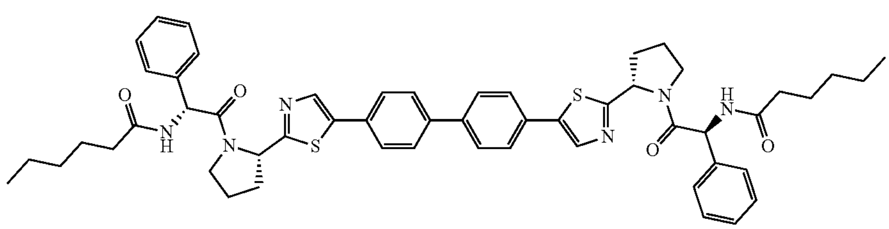 [SMILES: CCCCCC(=O)N[C@H](C(=O)N1CCC[C@H]1c1ncc(-c2ccc(-c3ccc(-c4cnc([C@@H]5CCCN5C(=O)[C@H](NC(=O)CCCCC)c5ccccc5)s4)cc3)cc2)s1)c1ccccc1] | 921 |
| 60a | 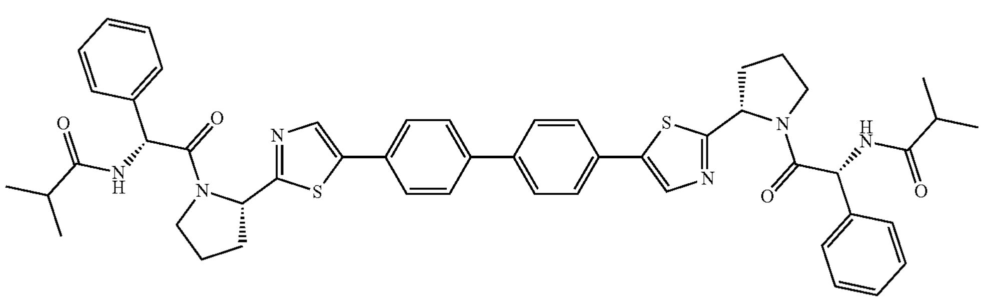 [SMILES: CC(C)C(=O)N[C@@H](C(=O)N1CCC[C@H]1c1ncc(-c2ccc(-c3ccc(-c4cnc([C@@H]5CCCN5C(=O)[C@H](NC(=O)C(C)C)c5ccccc5)s4)cc3)cc2)s1)c1ccccc1] | 865 |

TABLE 1-continued

| Structure | [M + H]+ |
|---|---|
| 61a | 865 |
| 62a | 921 |
| 63a | 921 |
| 64a | 893 |
| 65a | 893 |

TABLE 1-continued

| | Structure | [M + H]+ |
|---|---|---|
| 66a | 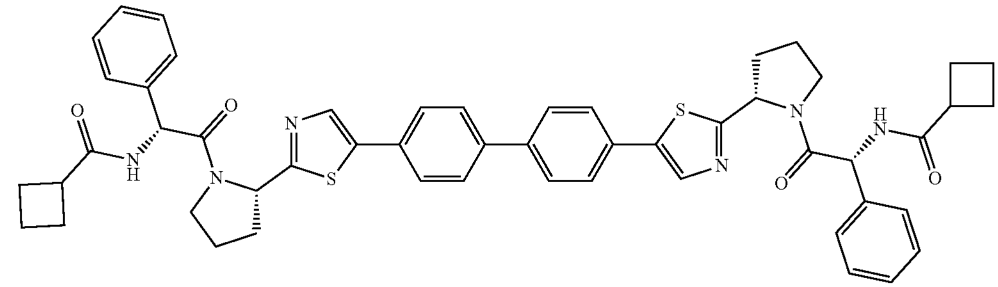 [SMILES: O=C(N[C@@H](C(=O)N1CCC[C@H]1c1ncc(-c2ccc(-c3ccc(-c4cnc([C@@H]5CCCN5C(=O)[C@H](NC(=O)C5CCC5)c5ccccc5)s4)cc3)cc2)s1)c1ccccc1)C1CCC1] | 889 |
| 67a | 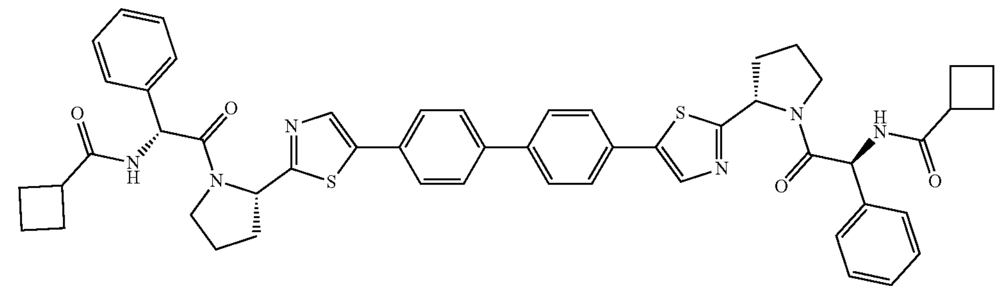 [SMILES: O=C(N[C@H](C(=O)N1CCC[C@H]1c1ncc(-c2ccc(-c3ccc(-c4cnc([C@@H]5CCCN5C(=O)[C@H](NC(=O)C5CCC5)c5ccccc5)s4)cc3)cc2)s1)c1ccccc1)C1CCC1] | 889 |
| 68a | 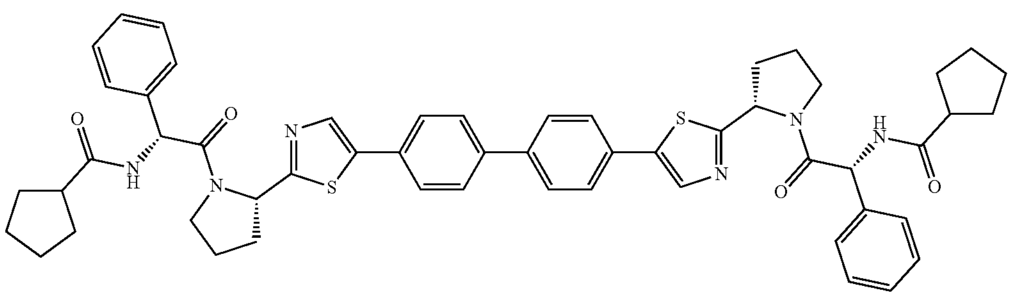 | 917 |
| 69a | 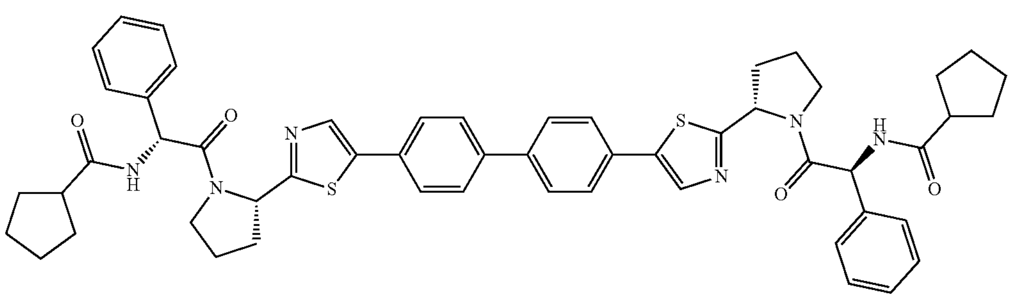 | 917 |
| 70a | 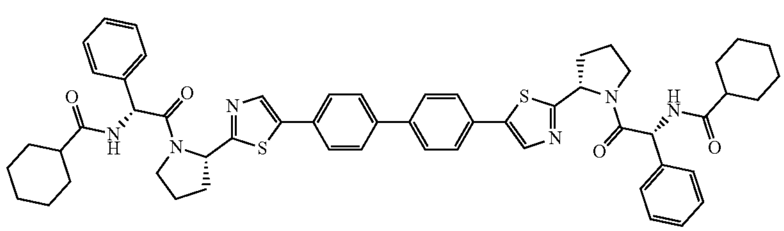 [SMILES: O=C(N[C@@H](C(=O)N1CCC[C@H]1c1ncc(-c2ccc(-c3ccc(-c4cnc([C@@H]5CCCN5C(=O)[C@H](NC(=O)C5CCCCC5)c5ccccc5)s4)cc3)cc2)s1)c1ccccc1)C1CCCCC1] | 945 |

TABLE 1-continued

| | Structure | [M + H]+ |
|---|---|---|
| 71a | 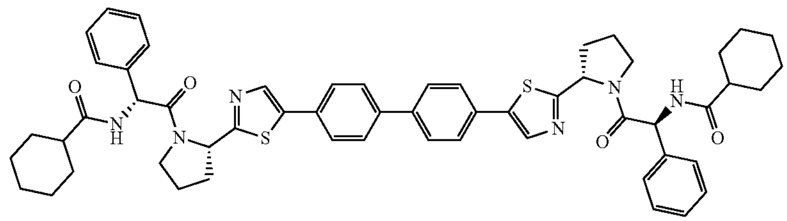 [SMILES: O=C(N[C@H](C(=O)N1CCC[C@H]1c1ncc(-c2ccc(-c3ccc(-c4cnc([C@@H]5CCCN5C(=O)[C@H](NC(=O)C5CCCCC5)c5ccccc5)s4)cc3)cc2)s1)c1ccccc1)C1CCCCC1] | 945 |
| 72a | 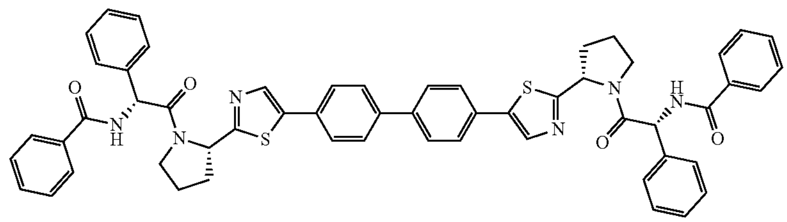 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccccc5)c5ccccc5)s4)cc3)cc2)s1)c1ccccc1)c1ccccc1] | 933 |
| 73a | 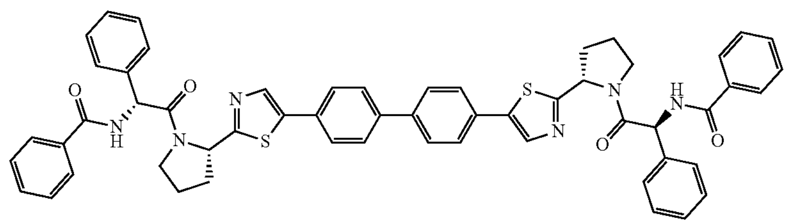 [SMILES: O=C(N[C@H](C(=O)N1CCC[C@H]1c1ncc(-c2ccc(-c3ccc(-c4cnc([C@@H]5CCCN5C(=O)[C@H](NC(=O)c5ccccc5)c5ccccc5)s4)cc3)cc2)s1)c1ccccc1)c1ccccc1] | 933 |
| 74a | 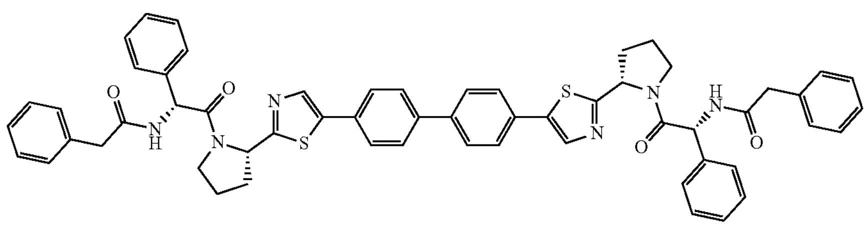 [SMILES: O=C(Cc1ccccc1)N[C@@H](C(=O)N1CCC[C@H]1c1ncc(-c2ccc(-c3ccc(-c4cnc([C@@H]5CCCN5C(=O)[C@H](NC(=O)Cc5ccccc5)c5ccccc5)s4)cc3)cc2)s1)c1ccccc1] | 961 |
| 75a | 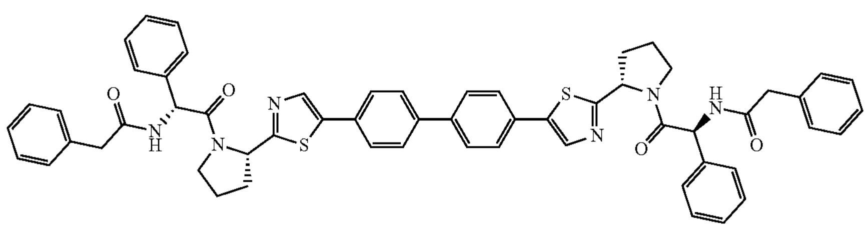 [SMILES: O=C(Cc1ccccc1)N[C@H](C(=O)N1CCC[C@H]1c1ncc(-c2ccc(-c3ccc(-c4cnc([C@@H]5CCCN5C(=O)[C@H](NC(=O)Cc5ccccc5)c5ccccc5)s4)cc3)cc2)s1)c1ccccc1] | 961 |
| 76a | 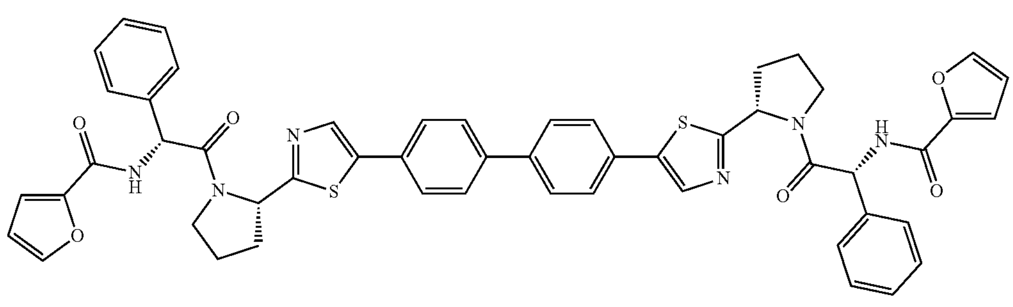 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccco5)c5ccccc5)s4)cc3)cc2)s1)c1ccccc1)c1ccco1] | 913 |

TABLE 1-continued

| | Structure | [M + H]+ |
|---|---|---|
| 77a | 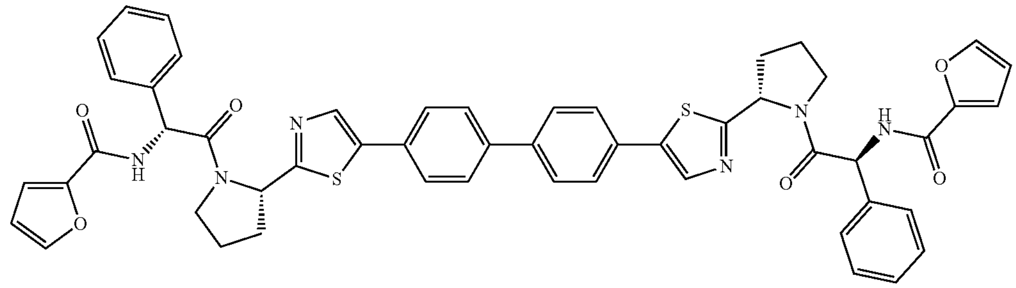 [SMILES: O=C(N[C@H](C(=O)N1CCC[C@H]1c1ncc(-c2ccc(-c3ccc(-c4cnc([C@@H]5CCCN5C(=O)[C@H](NC(=O)c5ccco5)c5ccccc5)s4)cc3)cc2)s1)c1ccccc1)c1ccco1] | 913 |
| 78a | 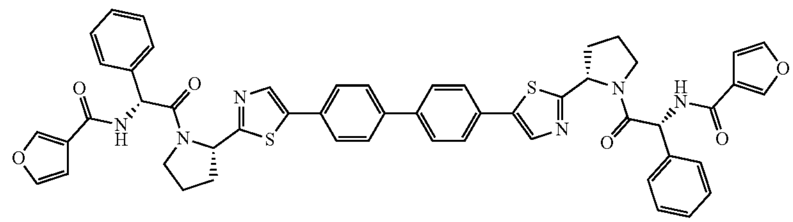 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccoc5)c5ccccc5)s4)cc3)cc2)s1)c1ccccc1)c1ccoc1] | 913 |
| 79a | 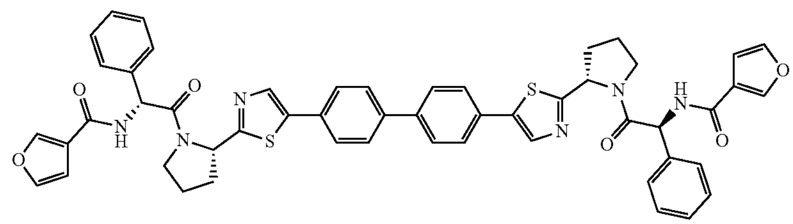 [SMILES: O=C(N[C@H](C(=O)N1CCC[C@H]1c1ncc(-c2ccc(-c3ccc(-c4cnc([C@@H]5CCCN5C(=O)[C@H](NC(=O)c5ccoc5)c5ccccc5)s4)cc3)cc2)s1)c1ccccc1)c1ccoc1] | 913 |
| 80a | 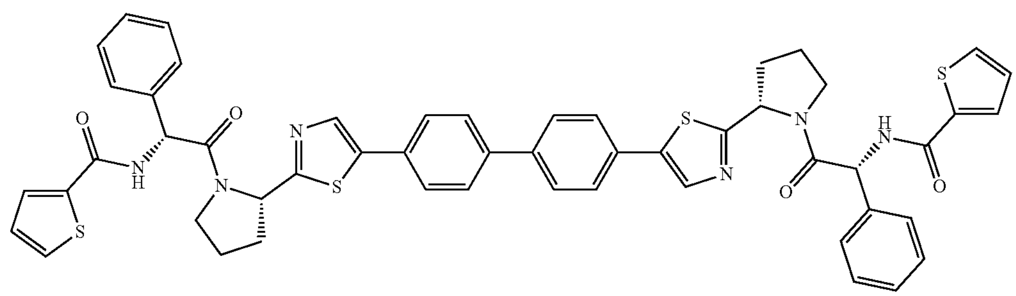 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5cccs5)c5ccccc5)s4)cc3)cc2)s1)c1ccccc1)c1cccs1] | 945 |
| 81a | 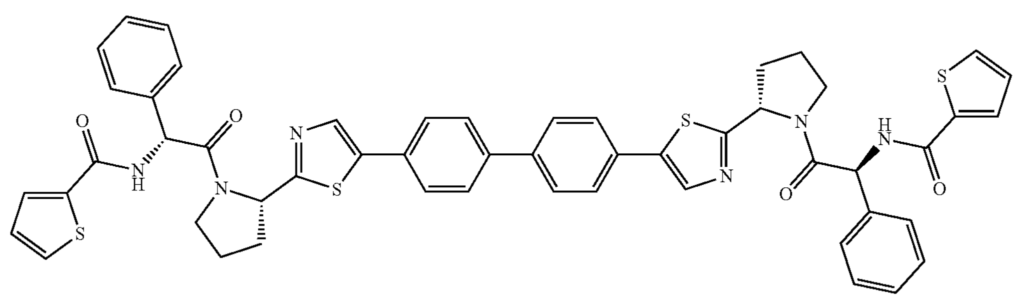 [SMILES: O=C(N[C@H](C(=O)N1CCC[C@H]1c1ncc(-c2ccc(-c3ccc(-c4cnc([C@@H]5CCCN5C(=O)[C@H](NC(=O)c5cccs5)c5ccccc5)s4)cc3)cc2)s1)c1ccccc1)c1cccs1] | 945 |
| 82a | 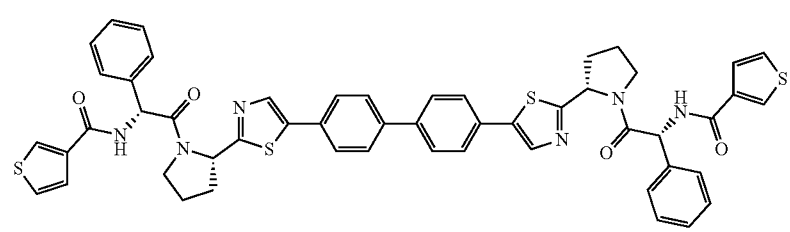 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccsc5)c5ccccc5)s4)cc3)cc2)s1)c1ccccc1)c1ccsc1] | 945 |

TABLE 1-continued
| | Structure | [M + H]+ |
|---|---|---|
| 83a | 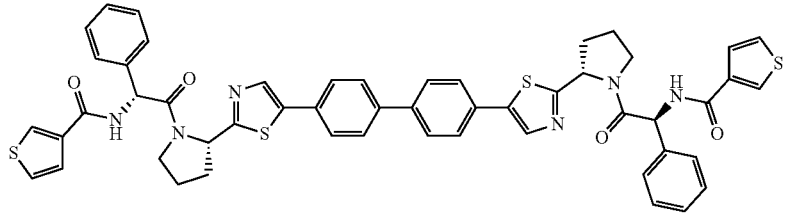 [SMILES: O=C(N[C@H](C(=O)N1CCC[C@H]1c1ncc(-c2ccc(-c3ccc(-c4cnc([C@@H]5CCCN5C(=O)[C@H](NC(=O)c5ccsc5)c5ccccc5)s4)cc3)cc2)s1)c1ccccc1)c1ccsc1] | 945 |
| 84a | 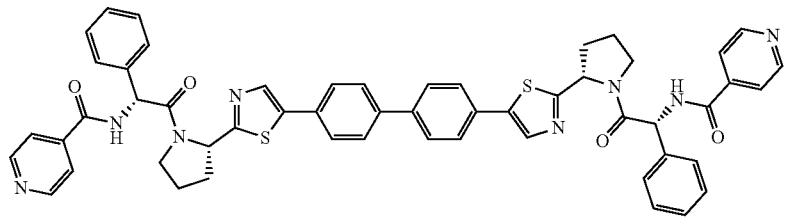 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccncc5)c5ccccc5)s4)cc3)cc2)s1)c1ccccc1)c1ccncc1] | 935 |
| 85a | 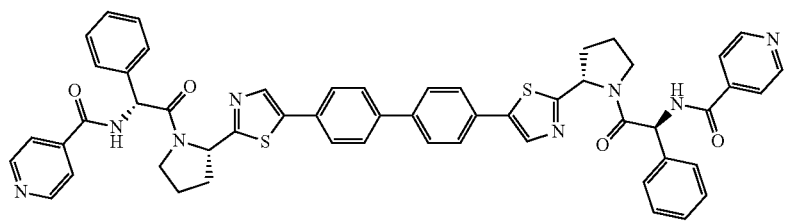 [SMILES: O=C(N[C@H](C(=O)N1CCC[C@H]1c1ncc(-c2ccc(-c3ccc(-c4cnc([C@@H]5CCCN5C(=O)[C@H](NC(=O)c5ccncc5)c5ccccc5)s4)cc3)cc2)s1)c1ccccc1)c1ccncc1] | 935 |
| 86a | 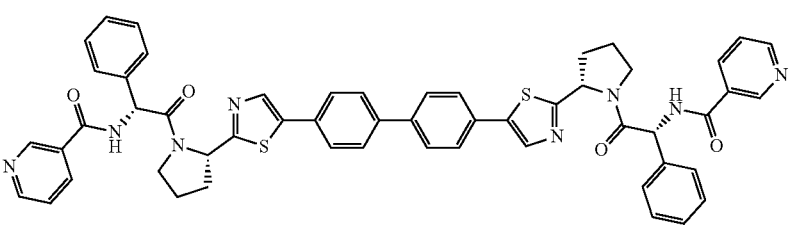 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5cccnc5)c5ccccc5)s4)cc3)cc2)s1)c1ccccc1)c1cccnc1] | 935 |
| 87a | 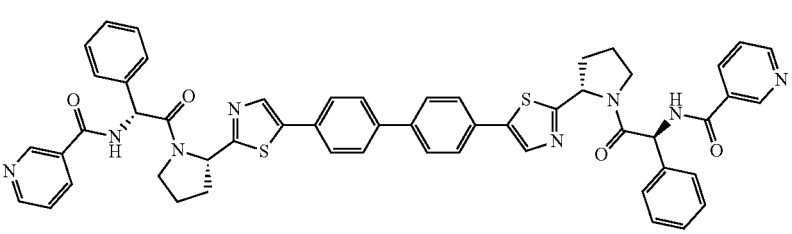 [SMILES: O=C(N[C@H](C(=O)N1CCC[C@H]1c1ncc(-c2ccc(-c3ccc(-c4cnc([C@@H]5CCCN5C(=O)[C@H](NC(=O)c5cccnc5)c5ccccc5)s4)cc3)cc2)s1)c1ccccc1)c1cccnc1] | 935 |
| 88a | 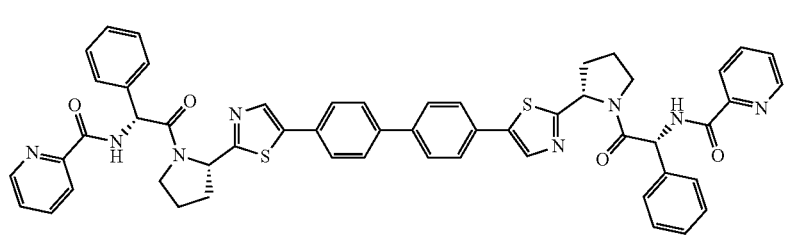 [SMILES: O=C(N[C@@H](C(=O)N1CCC[C@H]1c1ncc(-c2ccc(-c3ccc(-c4cnc([C@@H]5CCCN5C(=O)[C@H](NC(=O)c5ccccn5)c5ccccc5)s4)cc3)cc2)s1)c1ccccc1)c1ccccn1] | 935 |
| 89a | 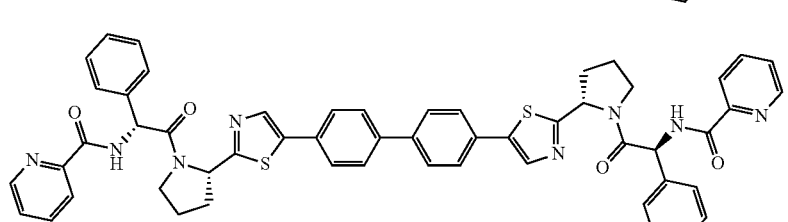 | 935 |

TABLE 1-continued

| | Structure | [M + H]+ |
|---|---|---|
| 90a | 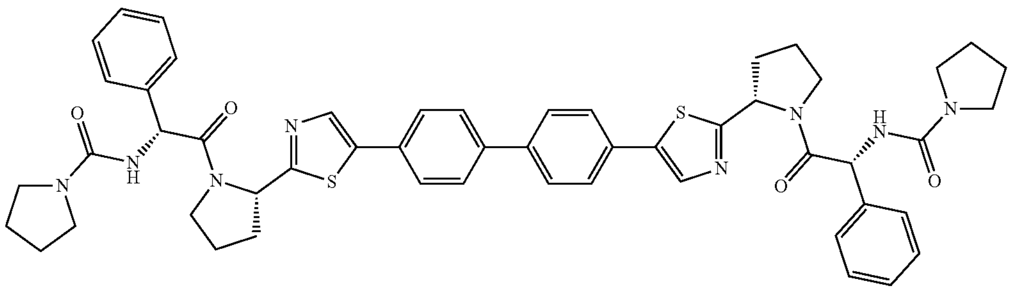 [SMILES: O=C(N[C@@H](C(=O)N1CCC[C@H]1c1ncc(-c2ccc(-c3ccc(-c4cnc([C@@H]5CCCN5C(=O)[C@H](NC(=O)N5CCCC5)c5ccccc5)s4)cc3)cc2)s1)c1ccccc1)N1CCCC1] | 919 |
| 91a | 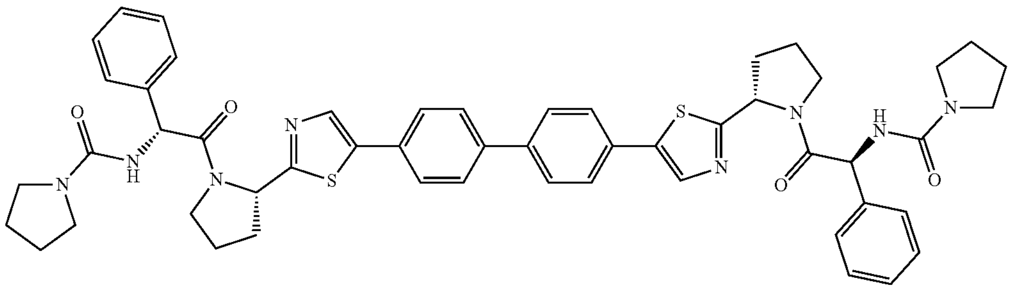 [SMILES: O=C(N[C@H](C(=O)N1CCC[C@H]1c1ncc(-c2ccc(-c3ccc(-c4cnc([C@@H]5CCCN5C(=O)[C@H](NC(=O)N5CCCC5)c5ccccc5)s4)cc3)cc2)s1)c1ccccc1)N1CCCC1] | 919 |
| 92a | 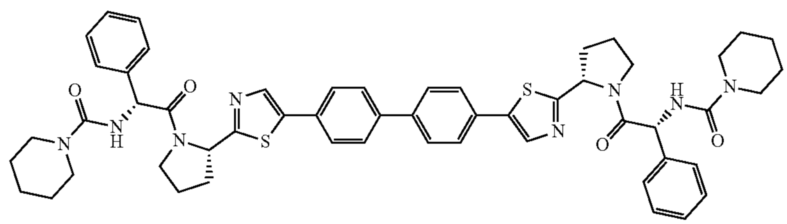 [SMILES: O=C(N[C@@H](C(=O)N1CCC[C@H]1c1ncc(-c2ccc(-c3ccc(-c4cnc([C@@H]5CCCN5C(=O)[C@H](NC(=O)N5CCCCC5)c5ccccc5)s4)cc3)cc2)s1)c1ccccc1)N1CCCCC1] | 947 |
| 95a | 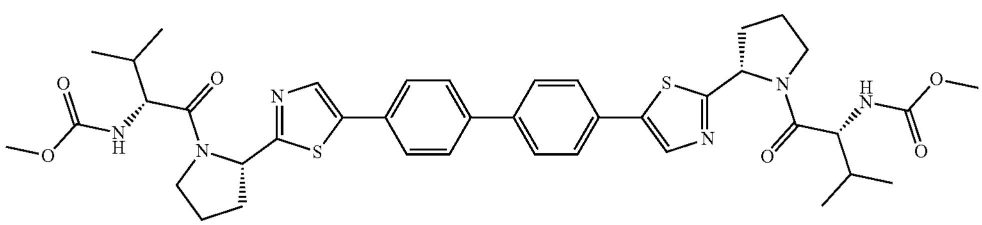 | 773 |
| 96a | 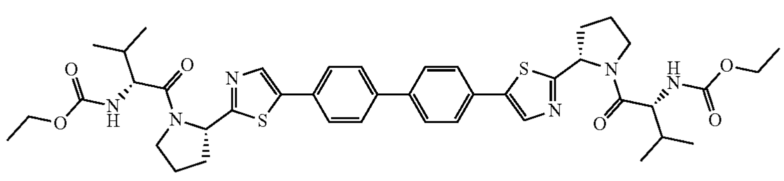 [SMILES: CCOC(=O)N[C@@H](C(=O)N1CCC[C@H]1c1ncc(-c2ccc(-c3ccc(-c4cnc([C@@H]5CCCN5C(=O)[C@H](NC(=O)OCC)C(C)C)s4)cc3)cc2)s1)C(C)C] | 801 |
| 97a | 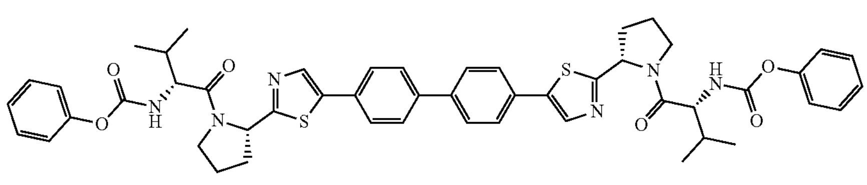 [SMILES: CC(C)[C@@H](NC(=O)Oc1ccccc1)C(=O)N1CCC[C@H]1c1ncc(-c2ccc(-c3ccc(-c4cnc([C@@H]5CCCN5C(=O)[C@H](NC(=O)Oc5ccccc5)C(C)C)s4)cc3)cc2)s1] | 897 |
| 98a | 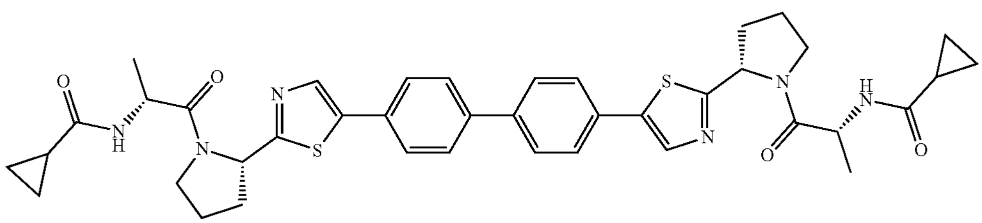 [SMILES: C[C@@H](NC(=O)C1CC1)C(=O)N1CCC[C@H]1c1ncc(-c2ccc(-c3ccc(-c4cnc([C@@H]5CCCN5C(=O)[C@@H](C)NC(=O)C5CC5)s4)cc3)cc2)s1] | 737 |

TABLE 1-continued
| | Structure | [M + H]+ |
|---|---|---|
| 99a | 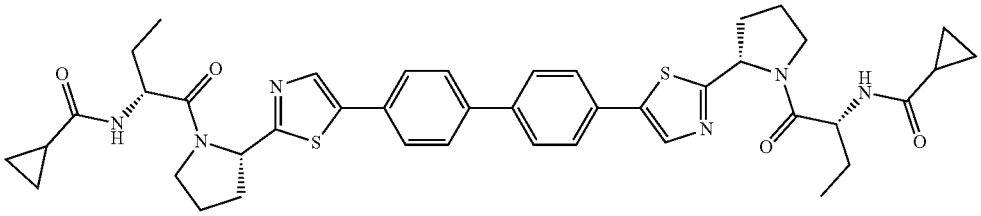 [SMILES: CC[C@@H](NC(=O)C1CC1)C(=O)N1CCC[C@H]1c1ncc(-c2ccc(-c3ccc(-c4cnc([C@@H]5CCCN5C(=O)[C@@H](CC)NC(=O)C5CC5)s4)cc3)cc2)s1] | 765 |
| 100a | 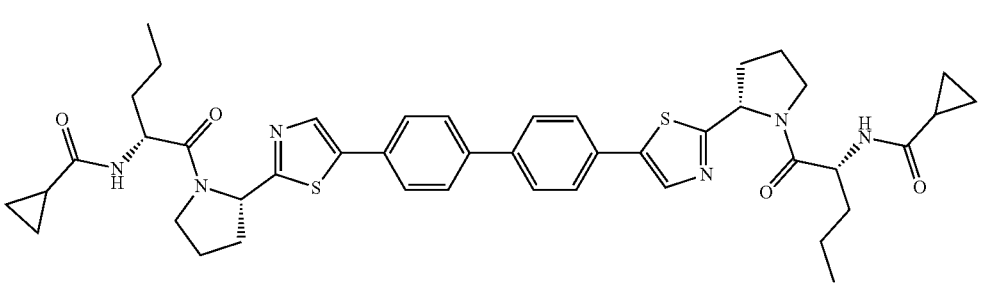 [SMILES: CCC[C@@H](NC(=O)C1CC1)C(=O)N1CCC[C@H]1c1ncc(-c2ccc(-c3ccc(-c4cnc([C@@H]5CCCN5C(=O)[C@@H](CCC)NC(=O)C5CC5)s4)cc3)cc2)s1] | 793 |
| 101a | 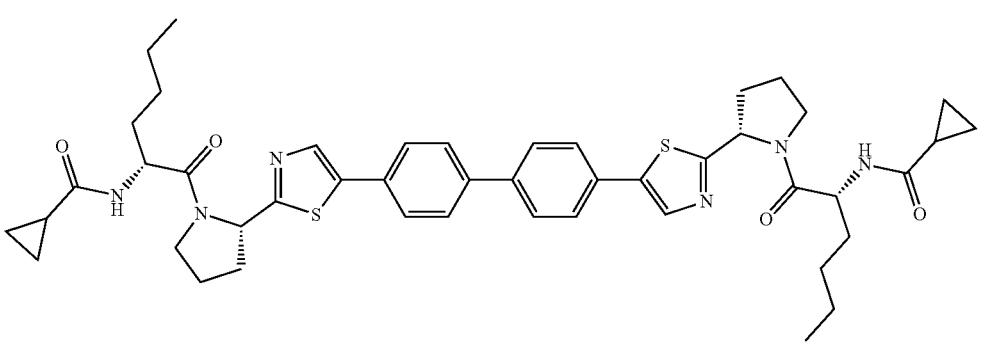 [SMILES: CCCC[C@@H](NC(=O)C1CC1)C(=O)N1CCC[C@H]1c1ncc(-c2ccc(-c3ccc(-c4cnc([C@@H]5CCCN5C(=O)[C@@H](CCCC)NC(=O)C5CC5)s4)cc3)cc2)s1] | 821 |
| 102a | 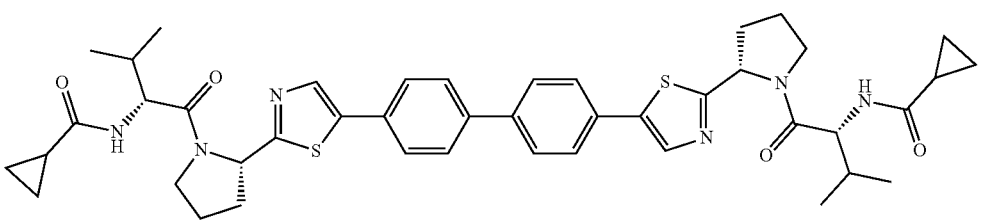 [SMILES: CC(C)[C@@H](NC(=O)C1CC1)C(=O)N1CCC[C@H]1c1ncc(-c2ccc(-c3ccc(-c4cnc([C@@H]5CCCN5C(=O)[C@H](NC(=O)C5CC5)C(C)C)s4)cc3)cc2)s1] | 793 |
| 103a | 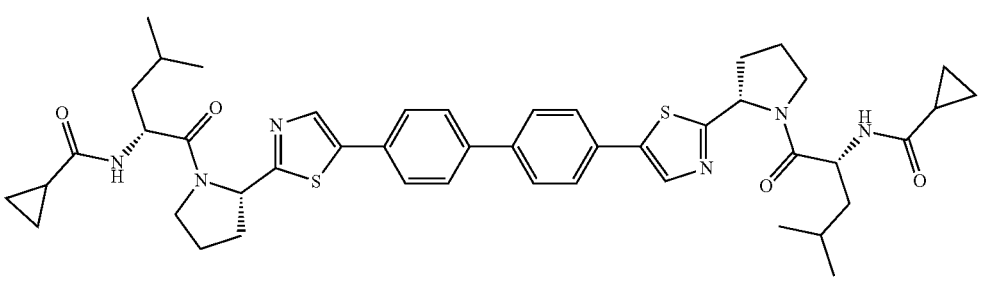 [SMILES: CC(C)C[C@@H](NC(=O)C1CC1)C(=O)N1CCC[C@H]1c1ncc(-c2ccc(-c3ccc(-c4cnc([C@@H]5CCCN5C(=O)[C@@H](CC(C)C)NC(=O)C5CC5)s4)cc3)cc2)s1] | 821 |
| 104a | 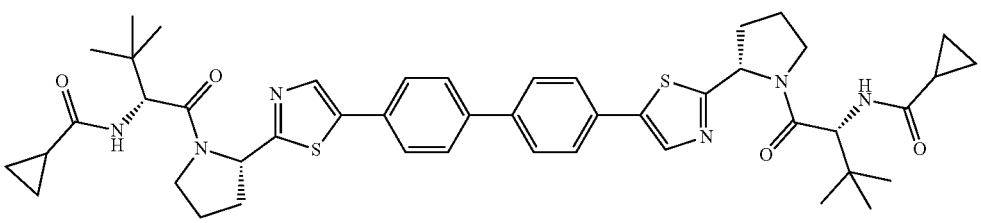 [SMILES: CC(C)(C)[C@@H](NC(=O)C1CC1)C(=O)N1CCC[C@H]1c1ncc(-c2ccc(-c3ccc(-c4cnc([C@@H]5CCCN5C(=O)[C@H](NC(=O)C5CC5)C(C)(C)C)s4)cc3)cc2)s1] | 821 |

TABLE 1-continued

| | Structure | [M + H]⁺ |
|---|---|---|
| 105a | 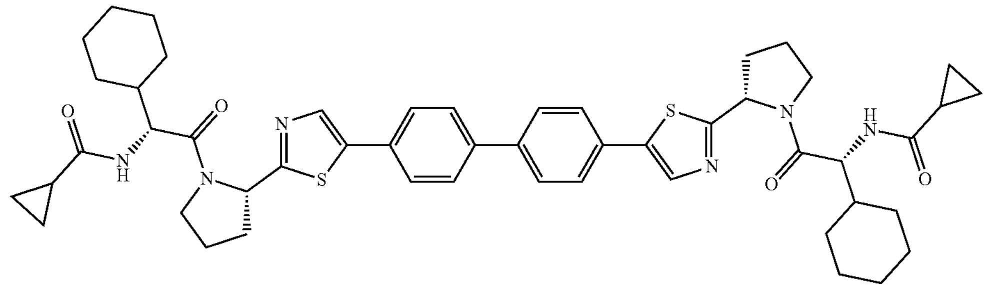 [SMILES: O=C(N[C@@H](C(=O)N1CCC[C@H]1c1ncc(-c2ccc(-c3ccc(-c4cnc([C@@H]5CCCN5C(=O)[C@H](NC(=O)C5CC5)C5CCCCC5)s4)cc3)cc2)s1)C1CCCCC1)C1CC1] | 873 |
| 106a | 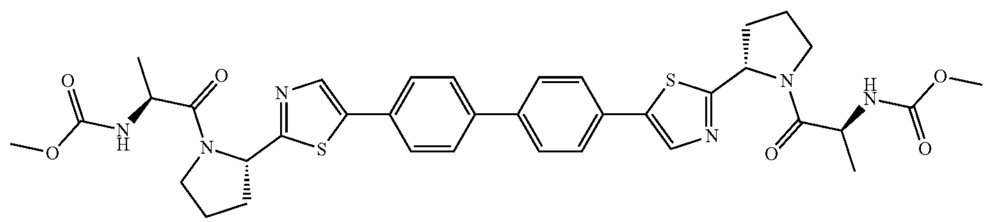 | 717 |
| 107a | 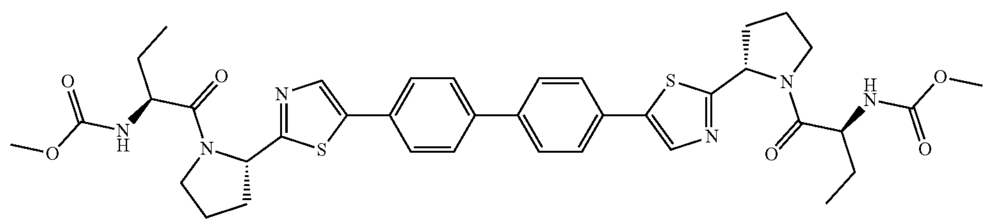 | 745 |
| 108a | 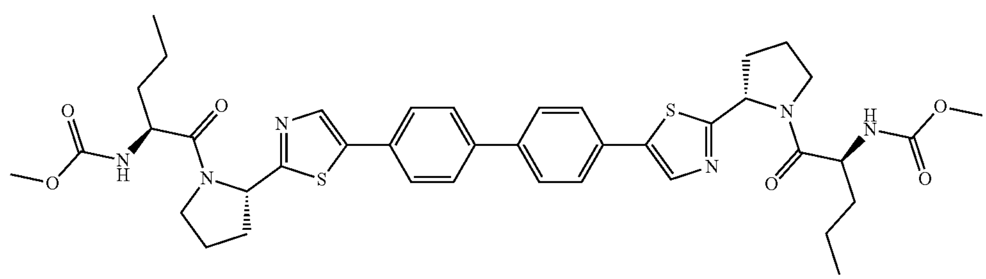 | 773 |
| 109a | 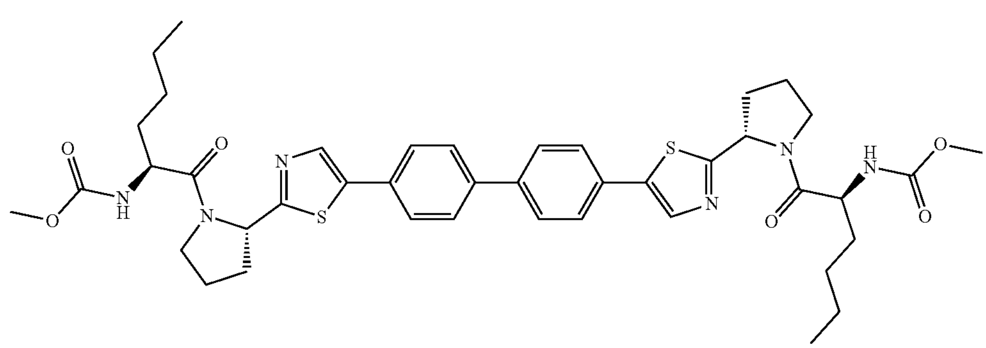 | 801 |

TABLE 1-continued

| | Structure | [M + H]+ |
|---|---|---|
| 110a | 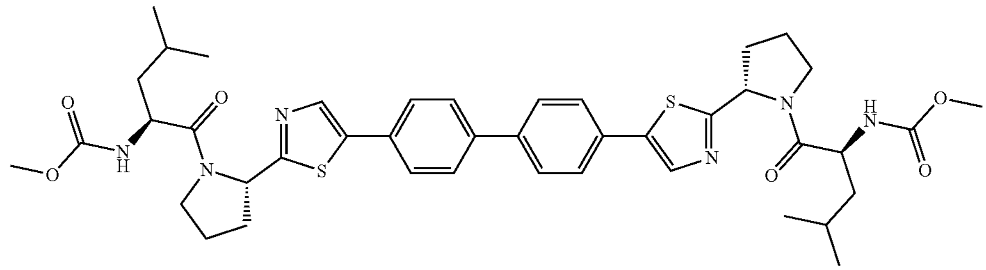 | 801 |
| 111a | 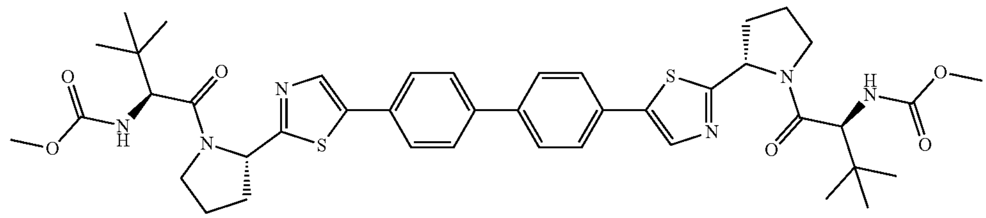 | 801 |
| 112a | 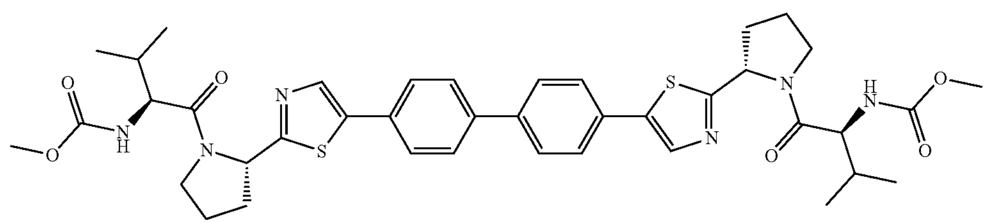 | 773 |
| 113a | 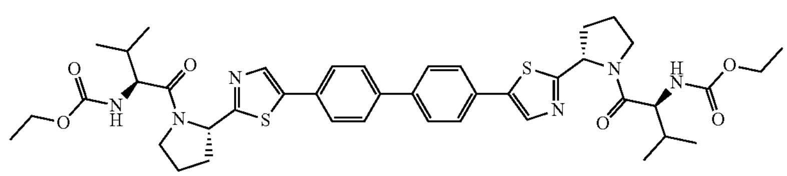 [SMILES: CCOC(=O)N[C@H](C(=O)N1CCC[C@H]1c1ncc(-c2ccc(-c3ccc(-c4cnc([C@@H]5CCCN5C(=O)[C@@H](NC(=O)OCC)C(C)C)s4)cc3)cc2)s1)C(C)C] | 801 |
| 114a | 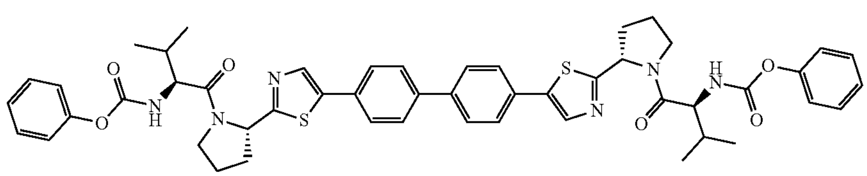 [SMILES: CC(C)[C@H](NC(=O)Oc1ccccc1)C(=O)N1CCC[C@H]1c1ncc(-c2ccc(-c3ccc(-c4cnc([C@@H]5CCCN5C(=O)[C@@H](NC(=O)Oc5ccccc5)C(C)C)s4)cc3)cc2)s1] | 897 |
| 123a | 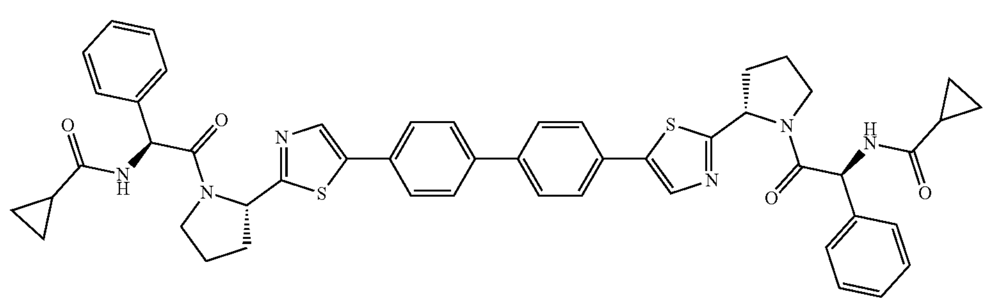 [SMILES: O=C(N[C@H](C(=O)N1CCC[C@H]1c1ncc(-c2ccc(-c3ccc(-c4cnc([C@@H]5CCCN5C(=O)[C@@H](NC(=O)C5CC5)c5ccccc5)s4)cc3)cc2)s1)c1ccccc1)C1CC1] | 861 |

TABLE 1-continued
| | Structure | [M + H]+ |
|---|---|---|
| 124a | 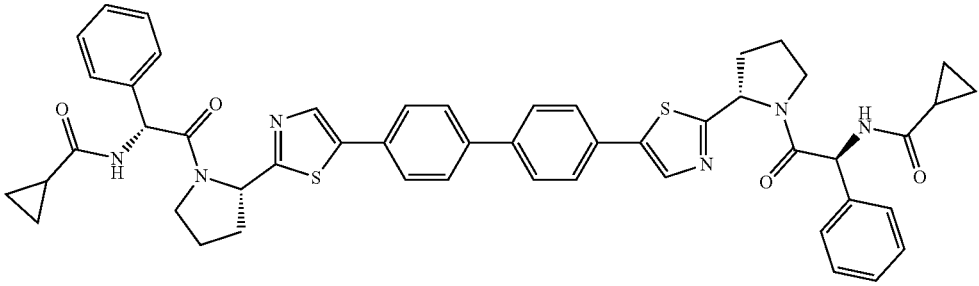 [SMILES: O=C(N[C@H](C(=O)N1CCC[C@H]1c1ncc(-c2ccc(-c3ccc(-c4cnc([C@@H]5CCCN5C(=O)[C@H](NC(=O)C5CC5)c5ccccc5)s4)cc3)cc2)s1)c1ccccc1)C1CC1] | 861 |
| 125a | 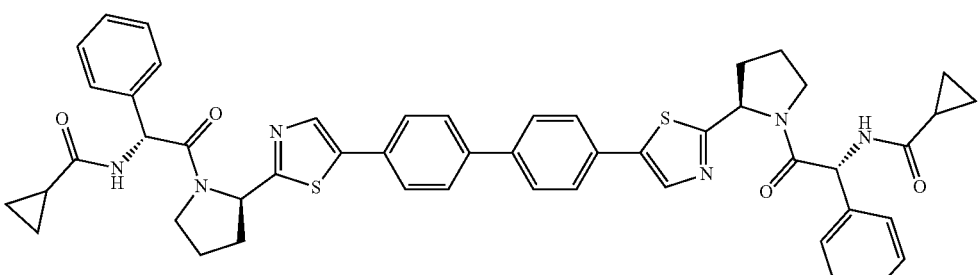 | 861 |
| 126a | 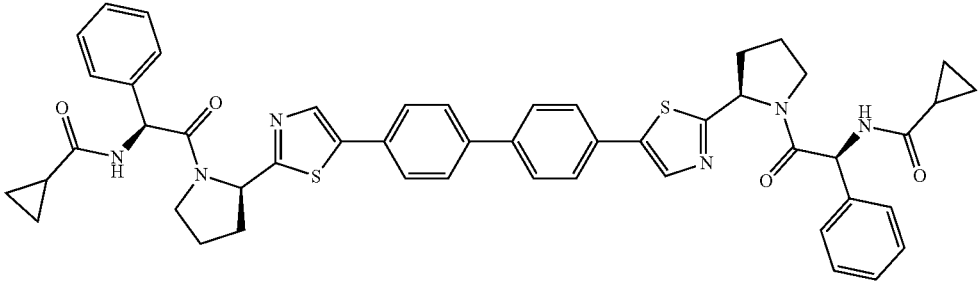 [SMILES: O=C(N[C@H](C(=O)N1CCC[C@@H]1c1ncc(-c2ccc(-c3ccc(-c4cnc([C@H]5CCCN5C(=O)[C@@H](NC(=O)C5CC5)c5ccccc5)s4)cc3)cc2)s1)c1ccccc1)C1CC1] | 861 |
| 127a | 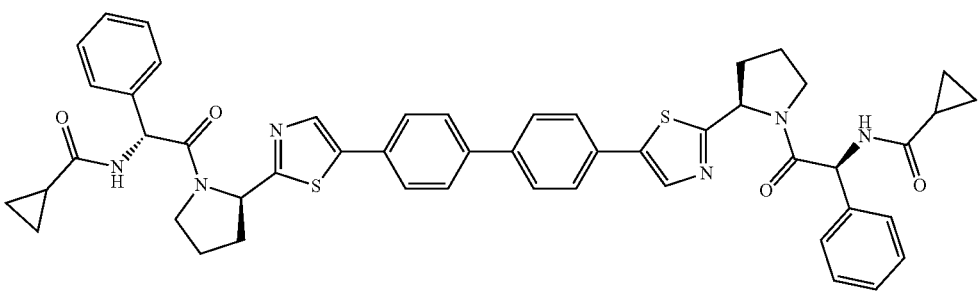 [SMILES: O=C(N[C@H](C(=O)N1CCC[C@@H]1c1ncc(-c2ccc(-c3ccc(-c4cnc([C@H]5CCCN5C(=O)[C@H](NC(=O)C5CC5)c5ccccc5)s4)cc3)cc2)s1)c1ccccc1)C1CC1] | 861 |
| 128a | 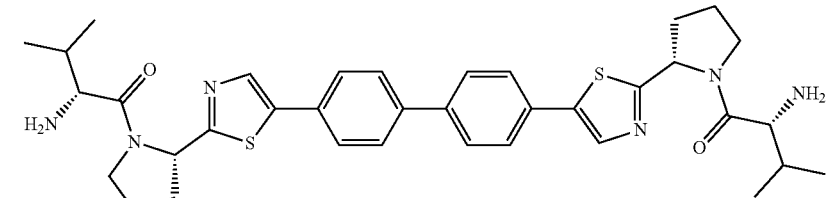 | 657 |

TABLE 1-continued
| | Structure | [M + H]+ |
|---|---|---|
| 129a | 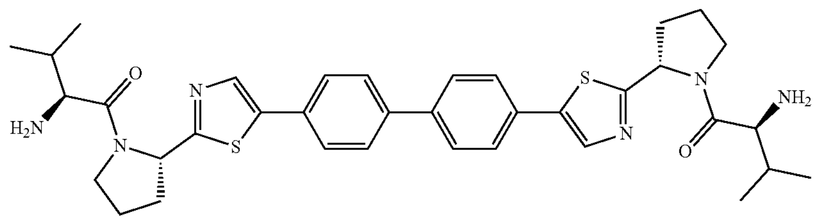 [SMILES: CC(C)[C@H](N)C(=O)N1CCC[C@H]1c1ncc(-c2ccc(-c3ccc(-c4cnc([C@@H]5CCCN5C(=O)[C@@H](N)C(C)C)s4)cc3)cc2)s1] | 657 |
Some additional exemplary compounds are shown below:
130a
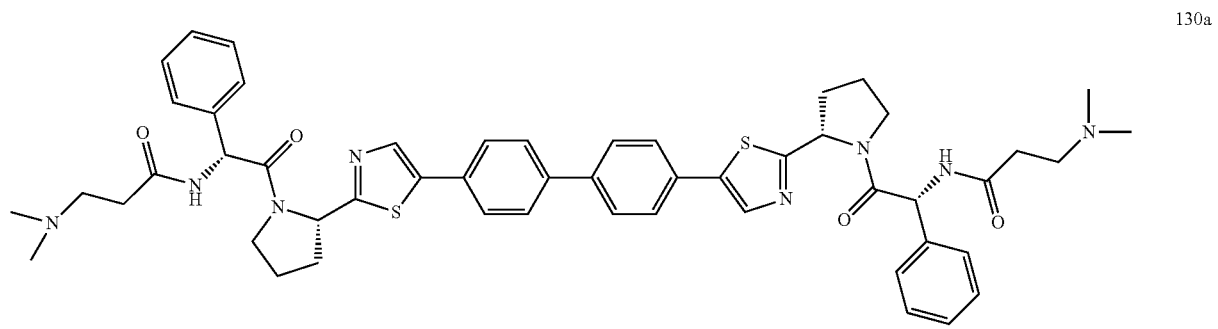
131a
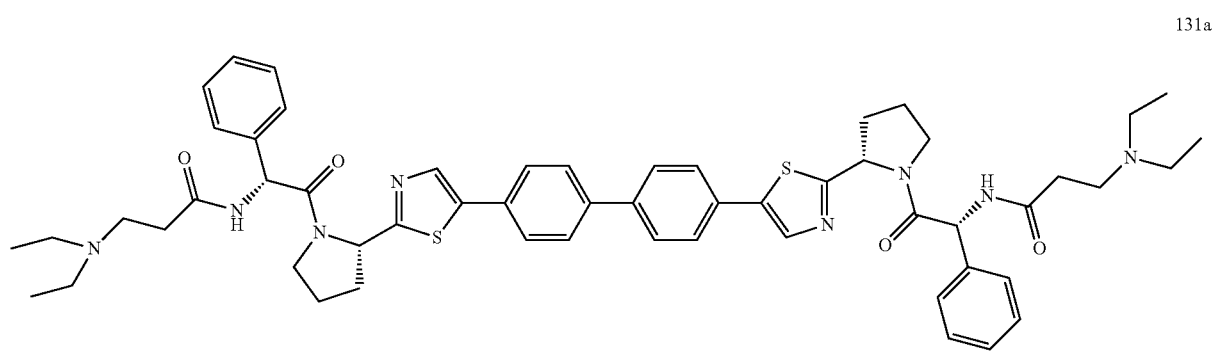
132a
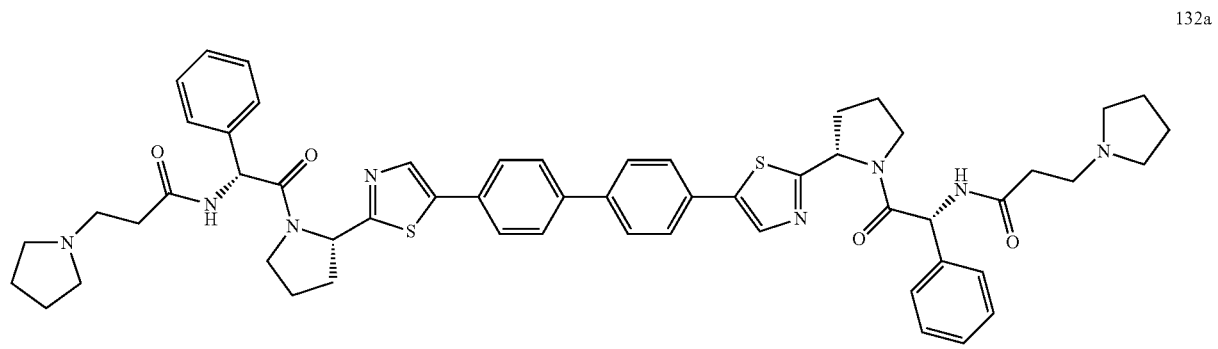

133a
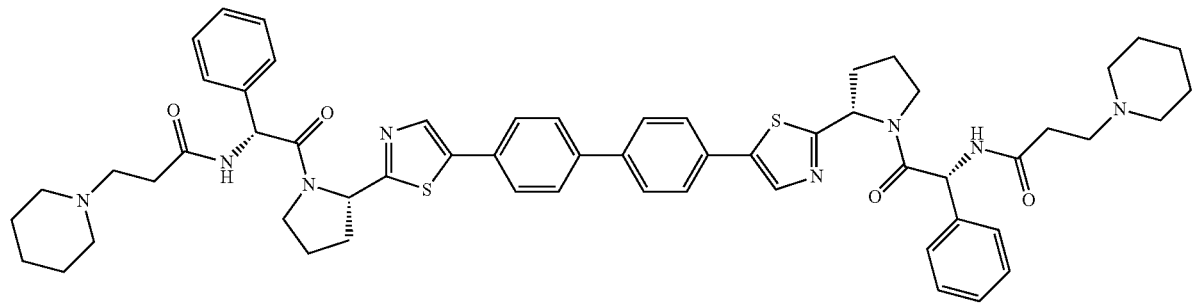
134a
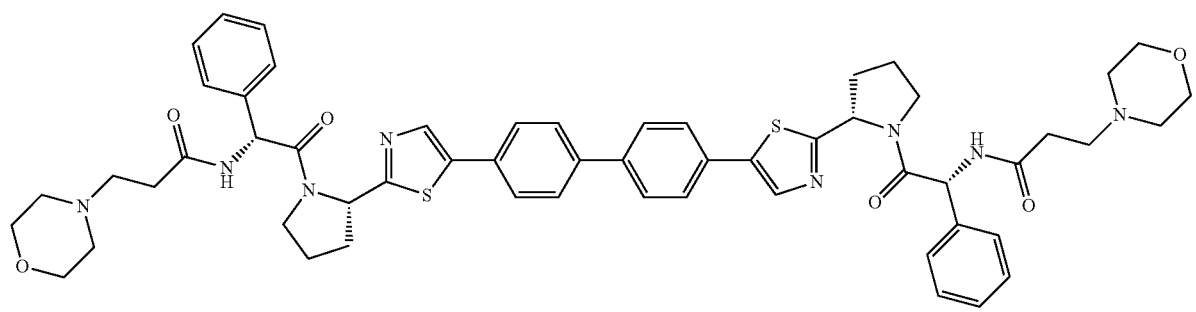
135a
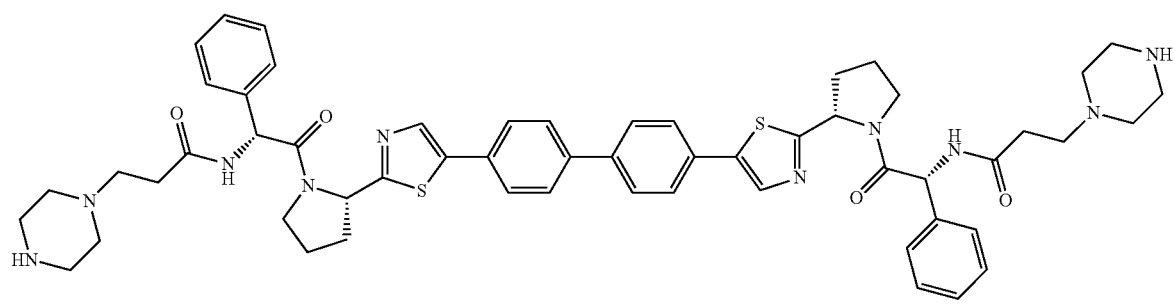
136a
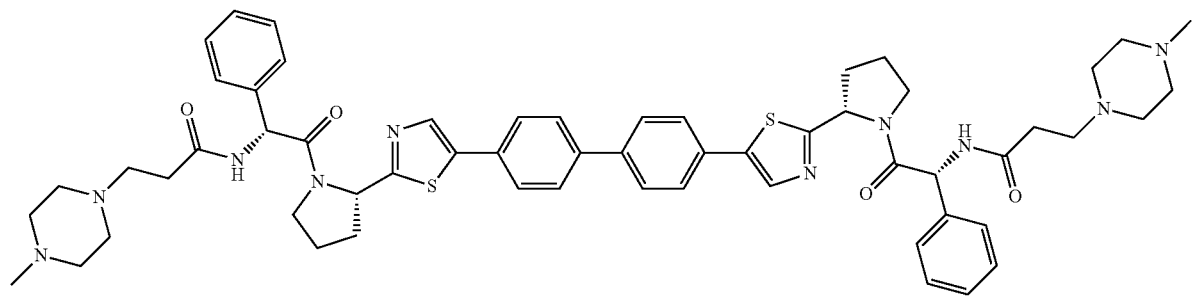
137a
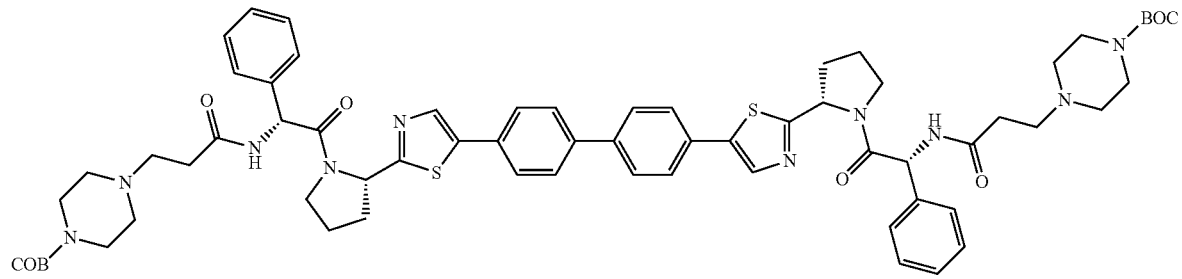

-continued
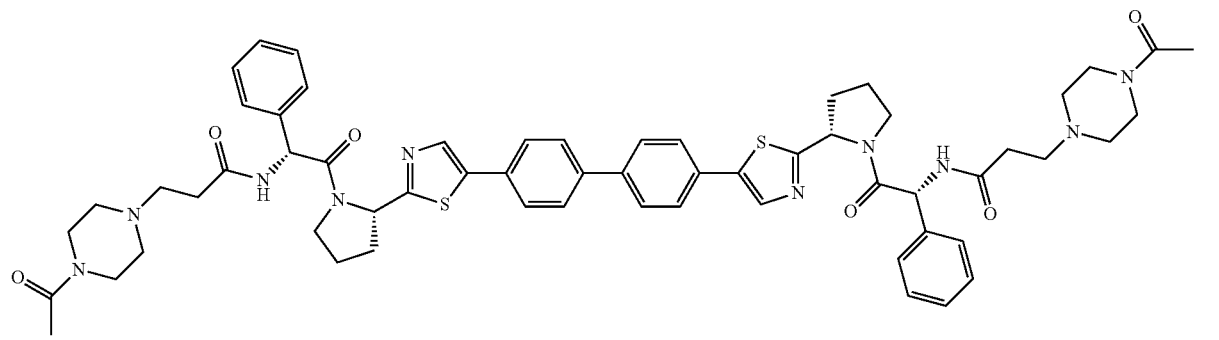
138a
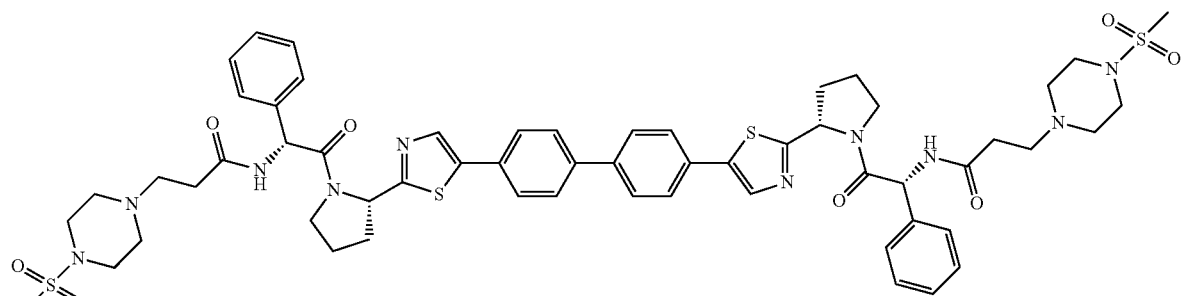
139a
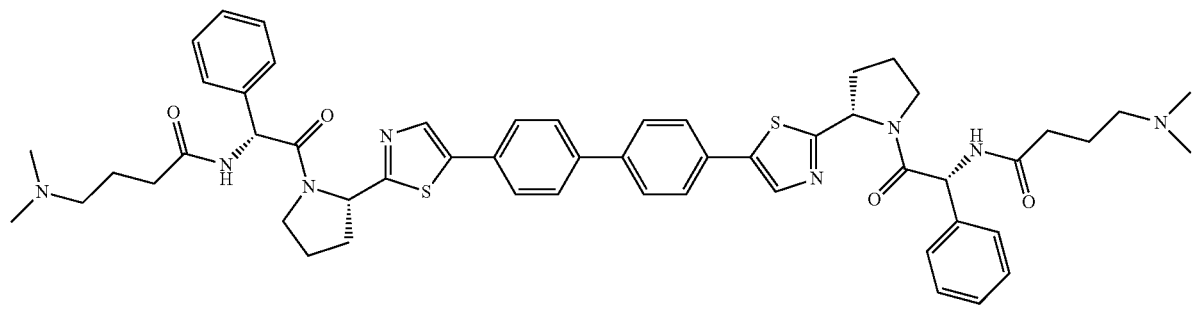
140a
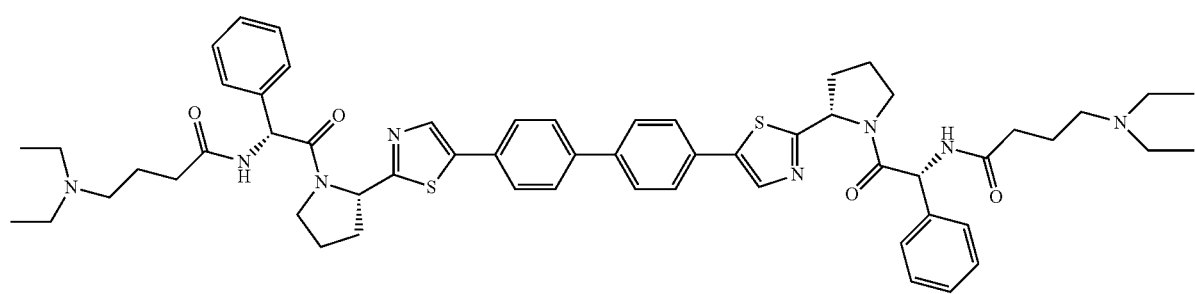
141a
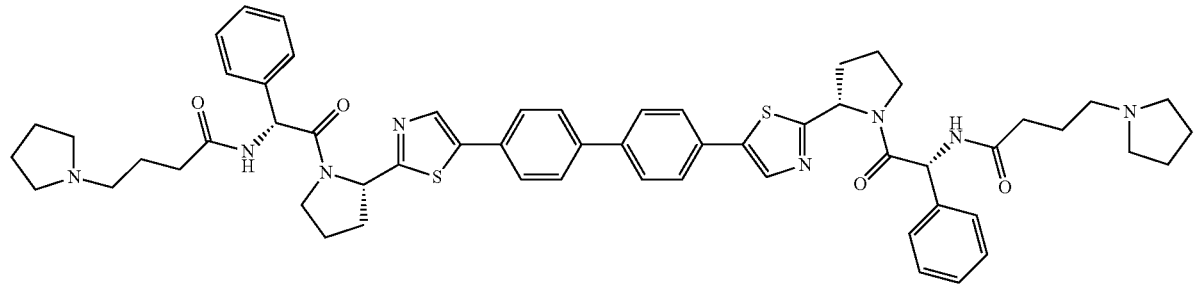
142a

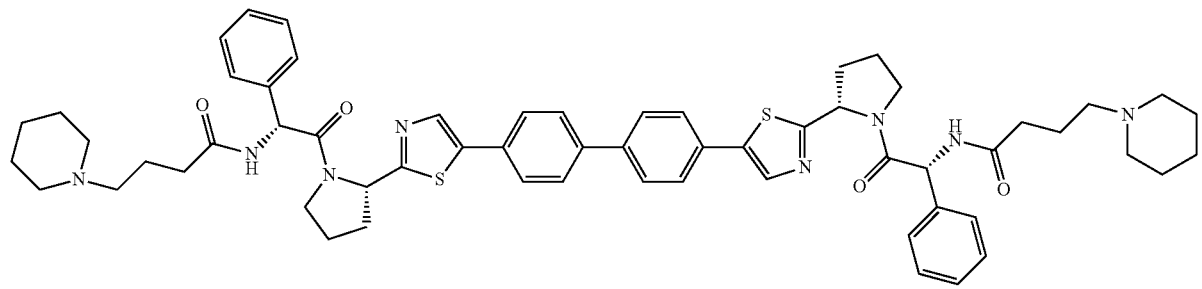
143a
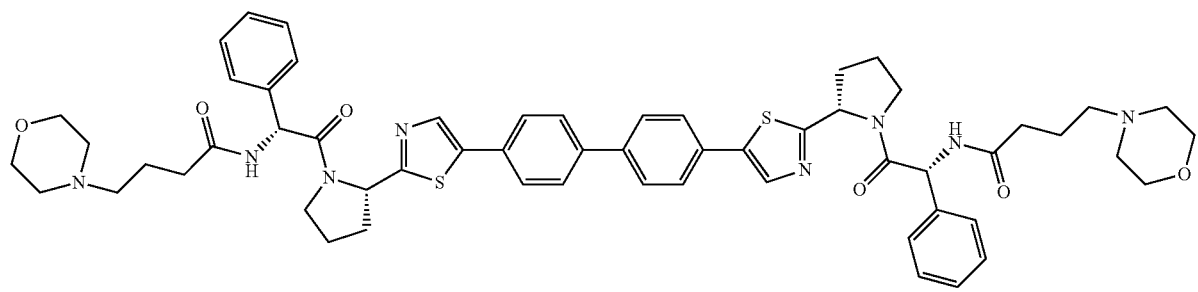
144a
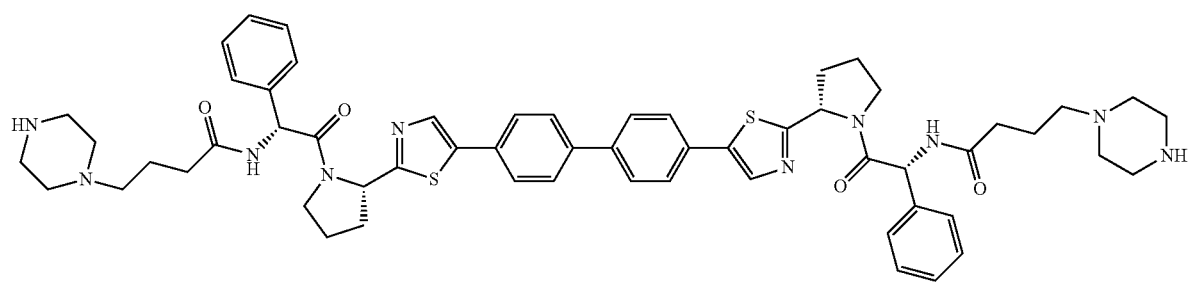
145a
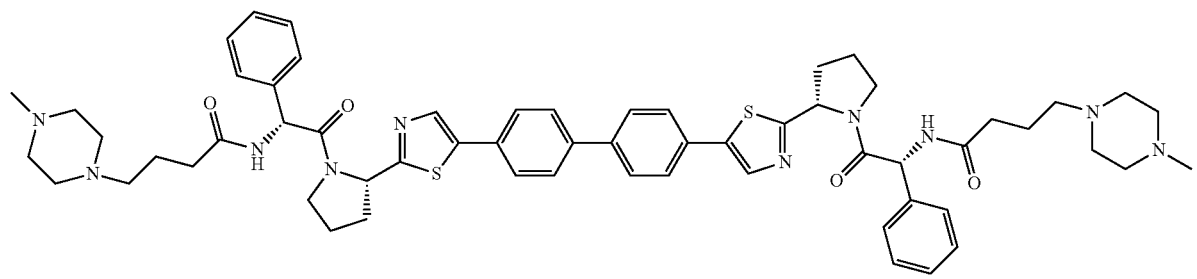
146a
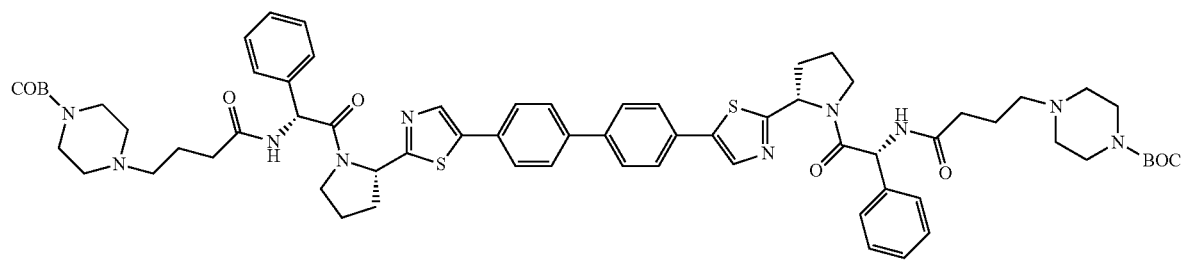
147a

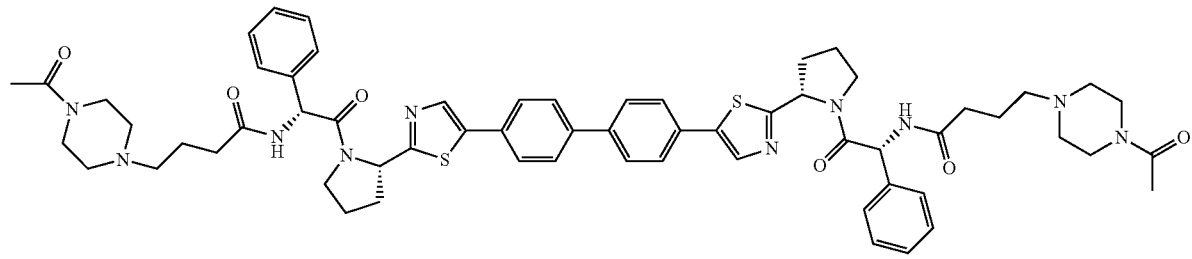
148a
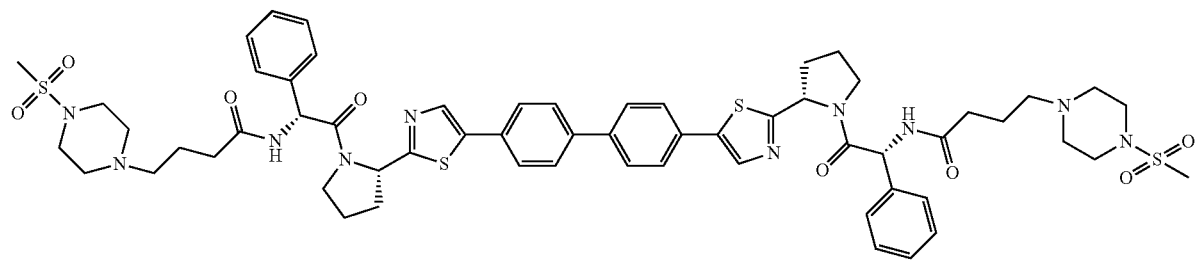
149a
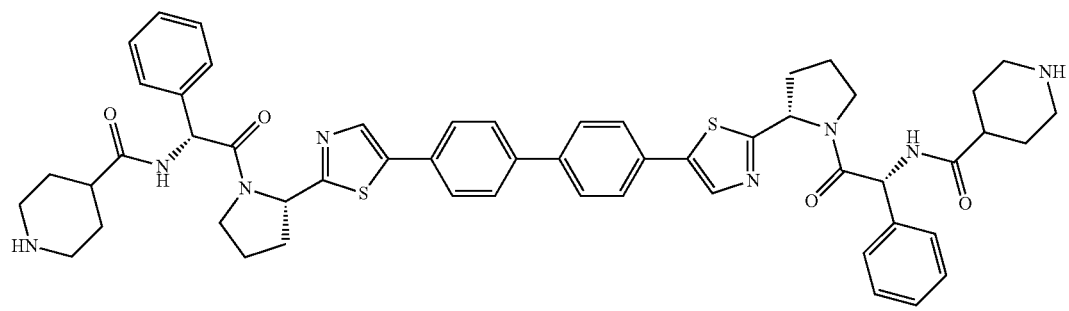
150a
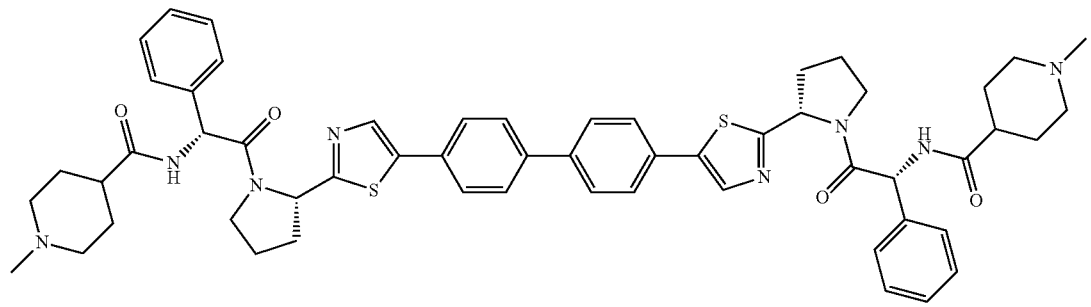
151a
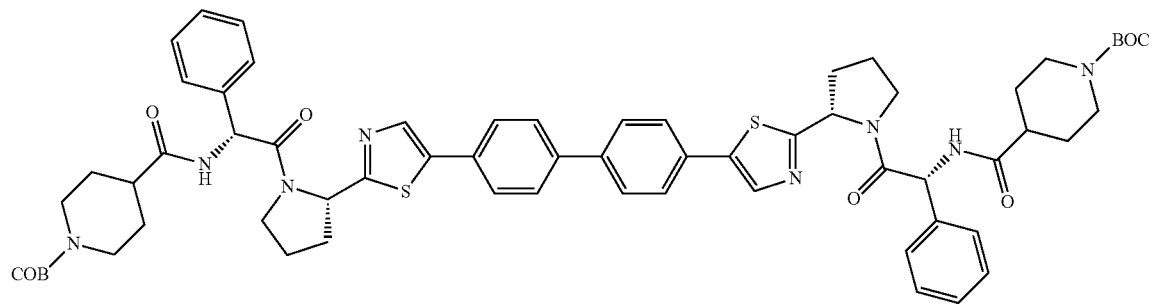
152a

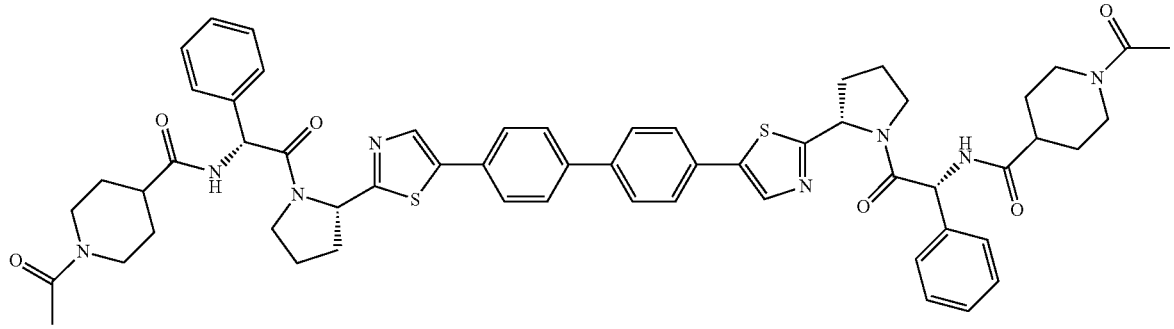

153a

The compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-13 below show transformations for synthesizing compounds of this invention.

Scheme 1 shows preparation of symmetric dithiazolylbiphenyl analogs 7a-c. 2-Amino-1-(4-bromophenyl)ethanone hydrochloride is coupled with N-Boc-L-Proline to yield 1,4-dicarbonyl compounds 1a-c. Subsequently, 1,4-dicarbonyl intermediates 1a-c are treated with Lawesson's reagent to produce aryl bromides 2a-c. To construct a symmetric biphenyl skeleton, aryl bromides 2a-c are reacted with bis(pinacolato)diboron to generate the corresponding arylboronic esters 3a-c, which are coupled with another equivalent of arylthiazole bromides 2a-c under Suzuki-Miyaura coupling conditions to afford the symmetric dithiazolylbiphenyl (compounds 4a-c). N-deprotection of compounds 4a-c in acid affords derivatives 5a-c, which are coupled with N-protected phenylglycine to afford the N-protected symmetric biphenyl peptides 6a-c. Boc-protecting groups are removed by treating 6a-c with acid. The crude product can be subsequently reacted with various alkyl or aryl acetyl chlorides to produce the final acylated products 7a-c.

Scheme 1

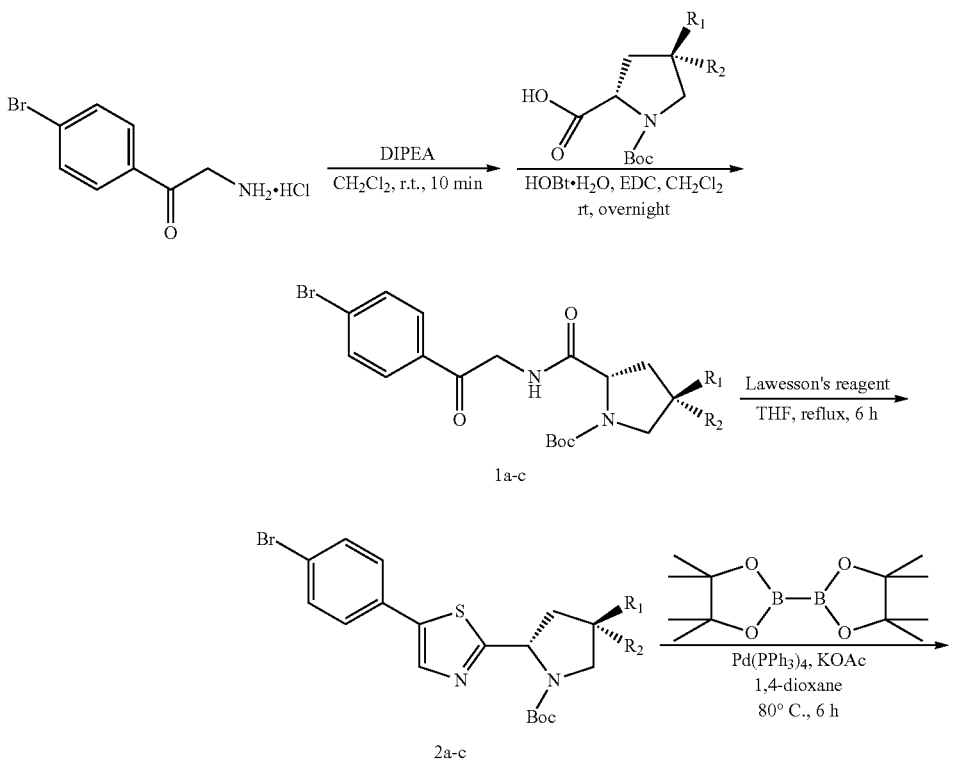

-continued
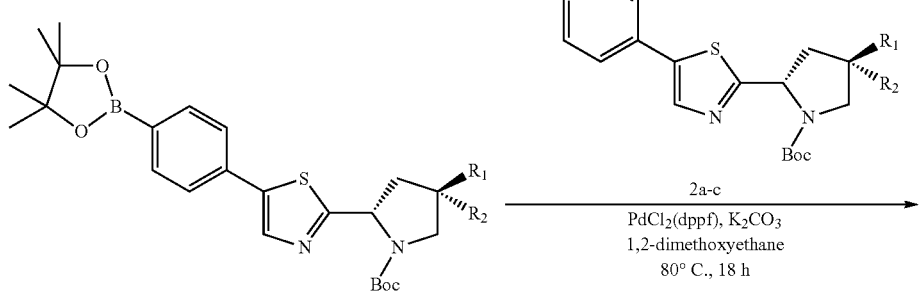
3a-c
2a-c
PdCl₂(dppf), K₂CO₃
1,2-dimethoxyethane
80° C., 18 h
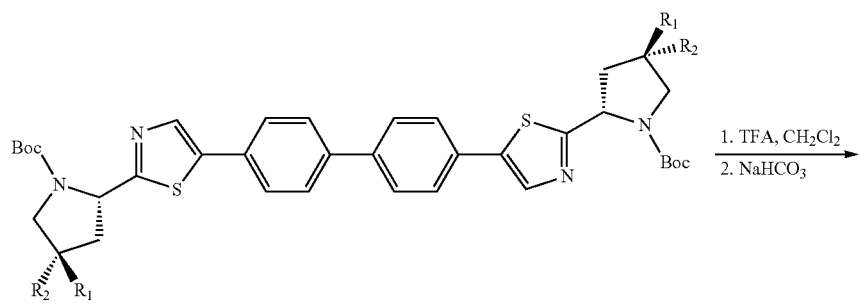
4a-c
1. TFA, CH₂Cl₂
2. NaHCO₃
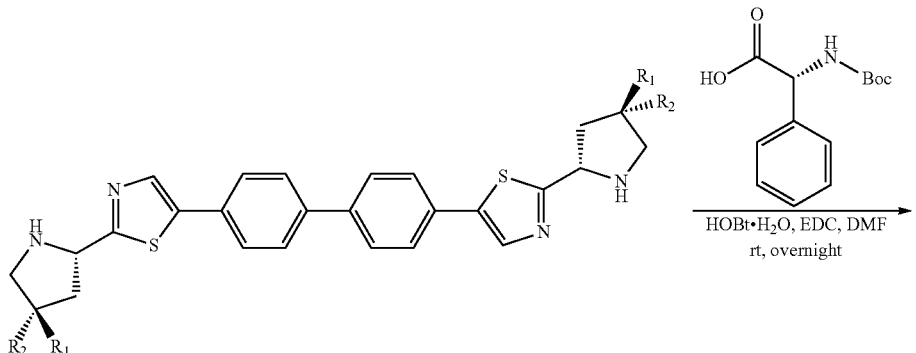
5a-c
HOBt·H₂O, EDC, DMF
rt, overnight
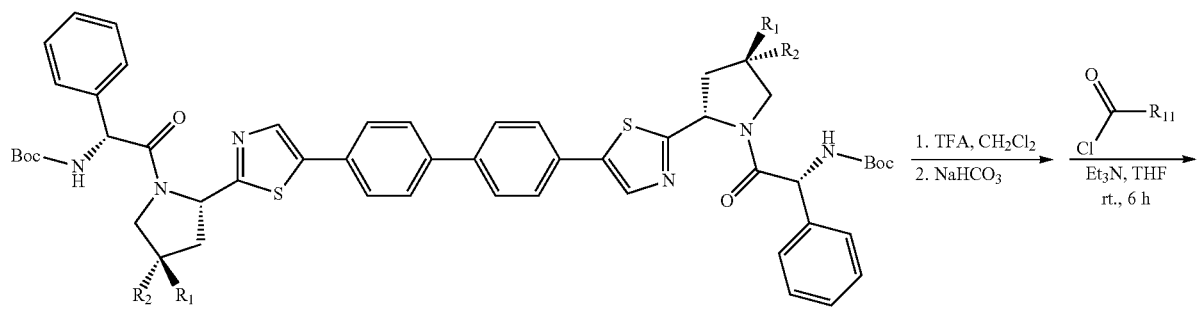
6a-c
1. TFA, CH₂Cl₂
2. NaHCO₃
Et₃N, THF
rt., 6 h

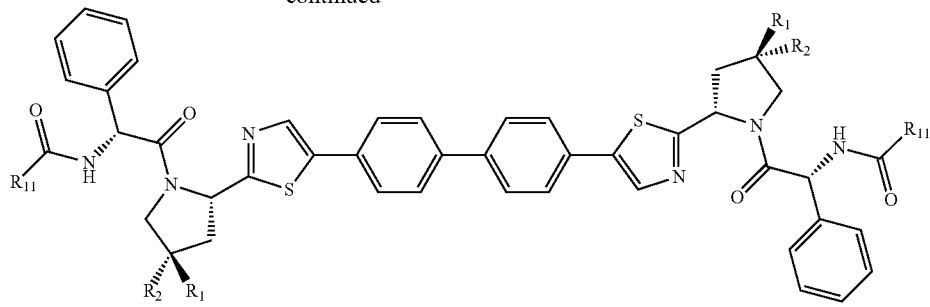

7a-c a: $R_1$ = H; $R_2$ = H
b: $R_1$ = F; $R_2$ = H or
c: $R_1$ = H; $R_2$ = F

An alternative synthetic route as shown in Scheme 2 below can be used to obtain symmetric dithiazolylbiphenyl analogs 7a-c. In this synthetic route, the essential intermediate, 4,4'-bis(2((S)-pyrrolidin-2-yl)thiazol-5-yl)biphenyls (compounds 5a-c), can be prepared in a similar manner as shown in Scheme 1; subsequent coupling of 5a-c with compound 8 affords analogues 7a-c.

Scheme 2

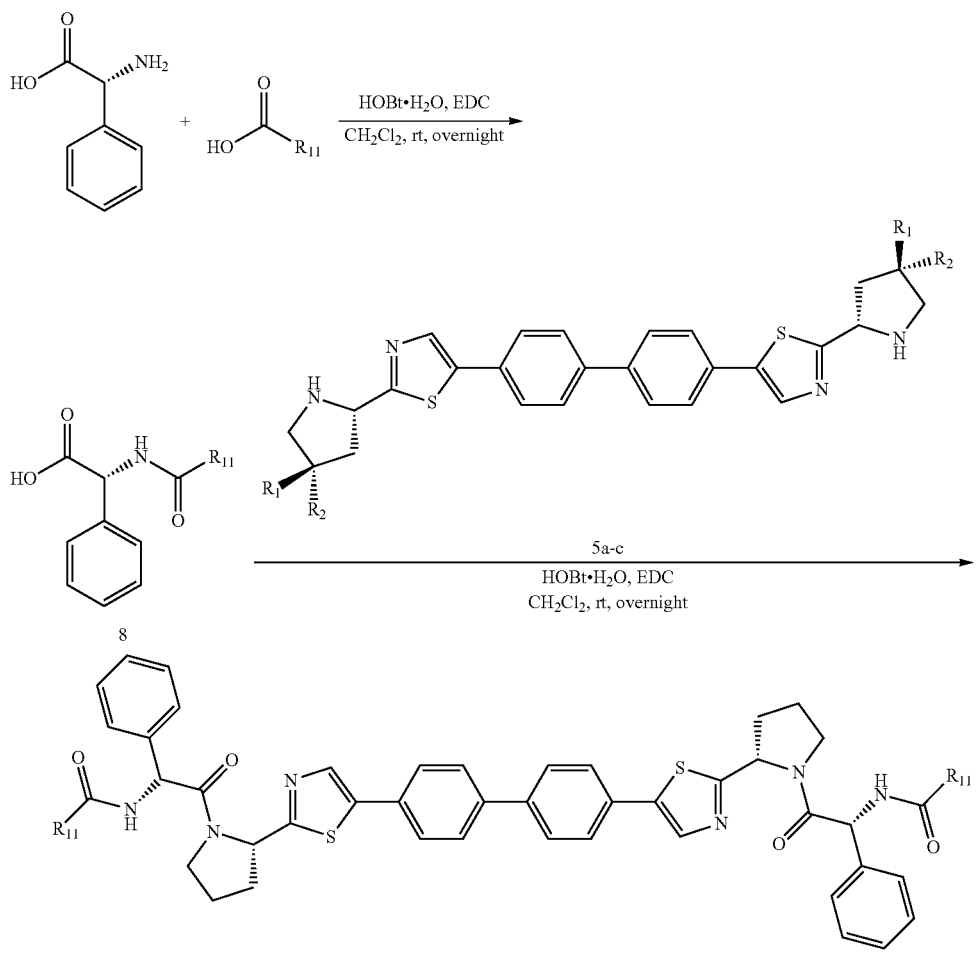

7a-c a: $R_1$ = H; $R_2$ = H
b: $R_1$ = F; $R_2$ = H or
c: $R_1$ = H; $R_2$ = F

Modification of the synthetic routes shown in Schemes 1 and 2 leads to preparation of certain compounds of this invention. For example, various multi-heteroaryl moieties of the compounds of this invention can be synthesized by coupling heteroaryl bromides (e.g., 12a~c, 16a~c, or 21a~c shown in Schemes 3-6 below) with arylboronic ester derivatives (e.g., 13a~c, 20a~c, or 22a~c also shown in Schemes 3-6 below).

As shown in Scheme 3 below, a simple method can be utilized to directly convert commercially available N-Boc-L-Proline 9a~c into primary amide 10a~c in good yield by using ammonium carbonate. (S)—N-Boc prolinamides 10a~c are treated with Lawesson's reagent at elevated temperature to give (S)—N-Boc carbamothioylpyrrolidine 11a~c. Condensation of 11a-c with 4-bromophenacyl bromide at room temperature can provid 1,3-thiazoles 12a~c in high yields. Utilizing bis(pinacolato)diboron as a substrate, the preparation of thiazyl arylboronic ester derivative 13a~c can be accomplished through Miyaura boration, which uses PdCl$_2$(dppf) and potassium acetate as catalysts.

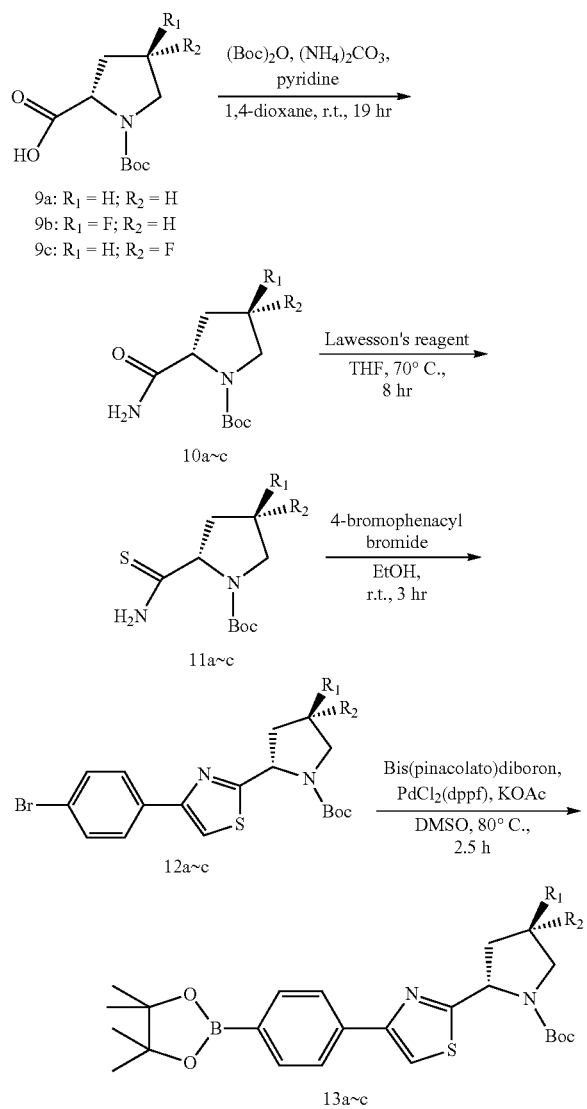

mobenzonitrile 14 with hydroxylamine hydrochloride in basic media under refluxing. Without further purification, amidoximes 15 are used to prepare bromophenyl 1,2,4-oxadiazole derivatives 16a~c. More specifically, condensing 4-bromobenzamidoxime 15 and commercially available N-protected L-proline 9a~c under alkali conditions affords compounds 16a~c in good yields.

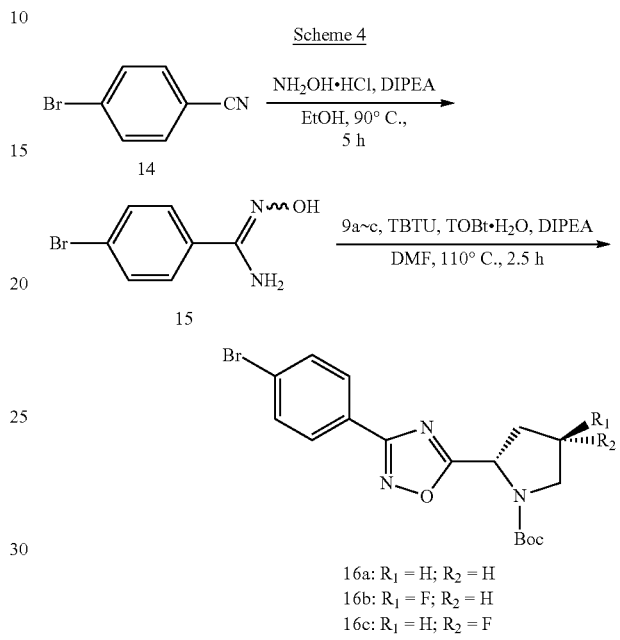

As shown in Scheme 5 below, aminoarylethanone salt 17 is coupled with N-Boc-L-Proline 9a~c to give compounds 18a~c, which are used to prepare both of phenylimidazoles (as shown in Scheme 5) and phenylthiazoles (as shown in Scheme 6). Compounds 18a~c can then be cyclized with ammonium acetate under thermal conditions to form phenylimidazole bromide derivatives 19a~c, which are converted to imidazolyl arylboronic ester derivative 20a~c through Miyaura boration.

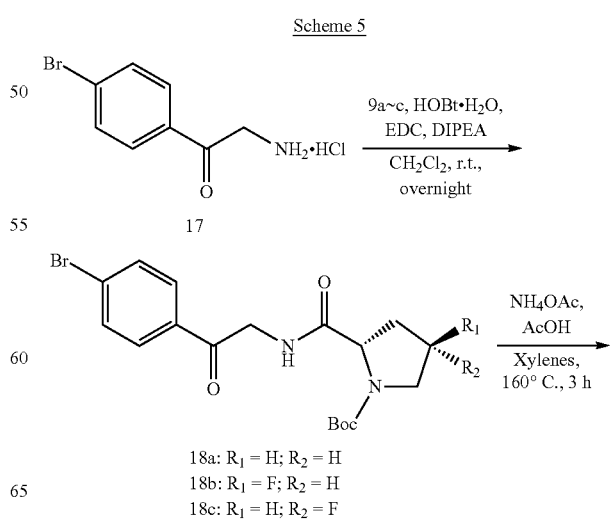

As shown in Scheme 4 below, amidoximes 15 (including syn- and/or anti-isomers) can be prepared by reacting 4-bro-

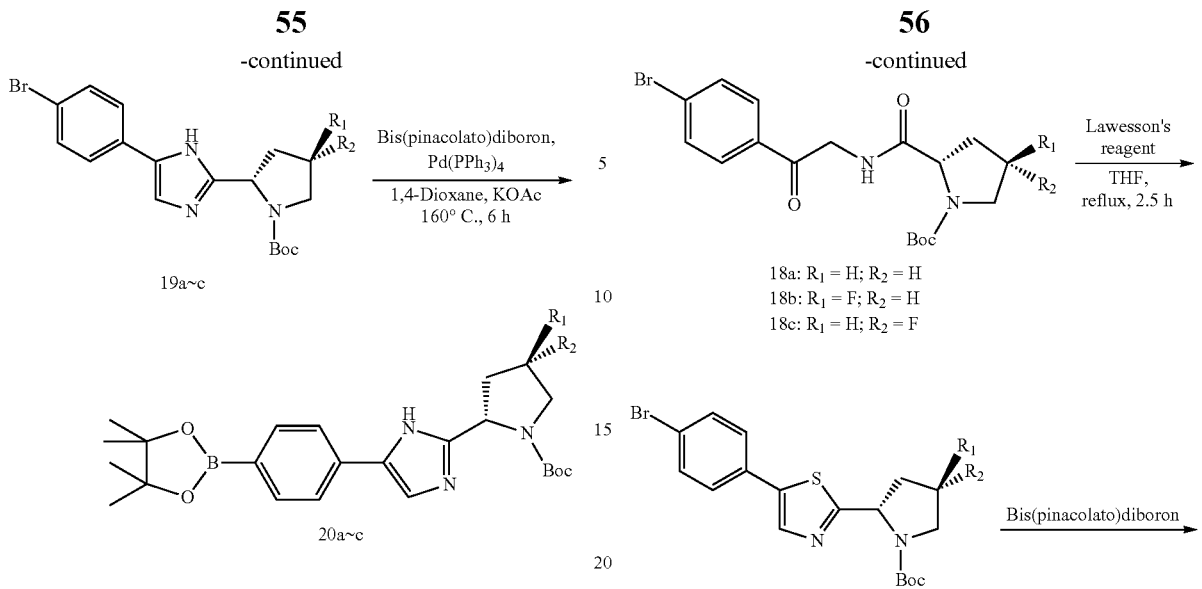

As shown in Scheme 6 below, compounds 18a~c are cyclized by utilizing Lawesson's reagent under reflux at a short time to yield phenylthiazole bromide 21a~c. Arylboronic ester derivatives 22a~c can be prepared from phenylthiazole bromide 21a~c through Miyaura boration.

Scheme 6

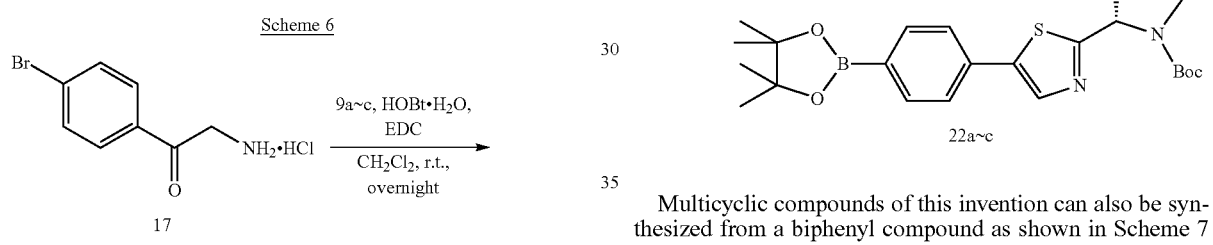

Multicyclic compounds of this invention can also be synthesized from a biphenyl compound as shown in Scheme 7 below:

Scheme 7

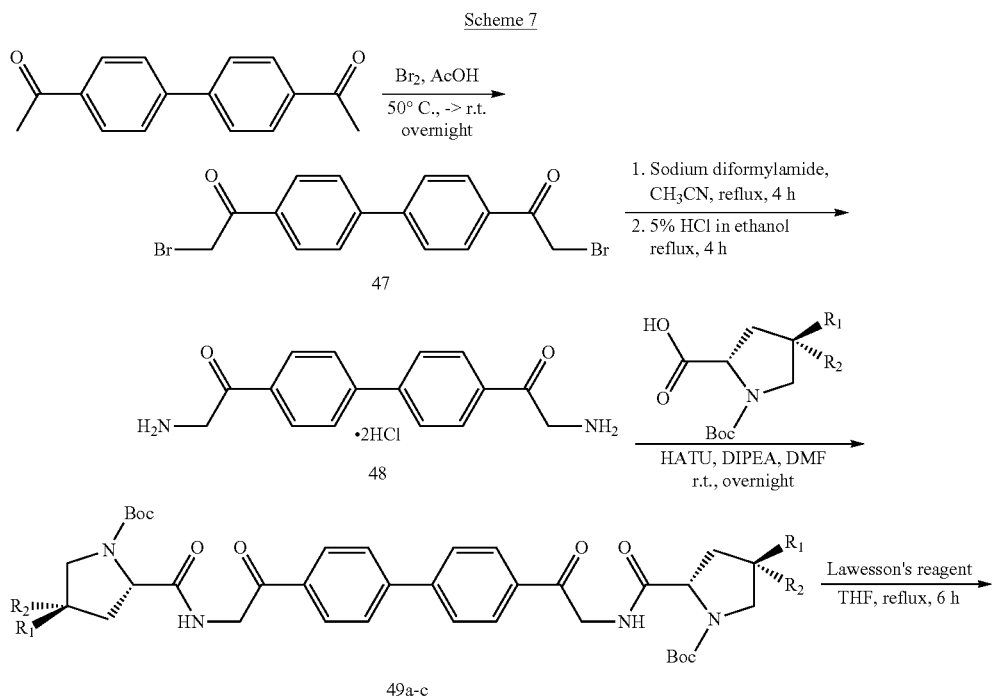

-continued
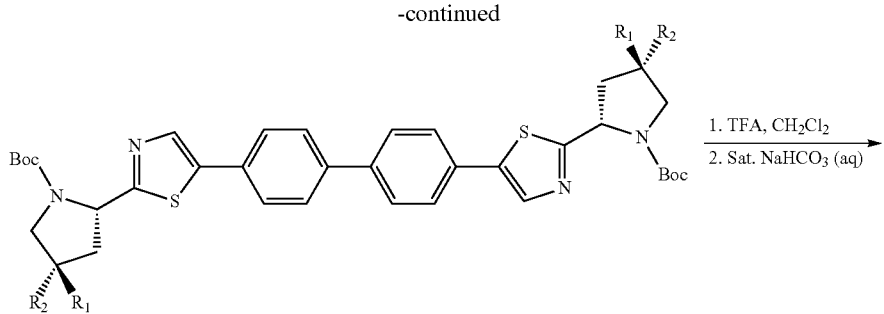
4a-c
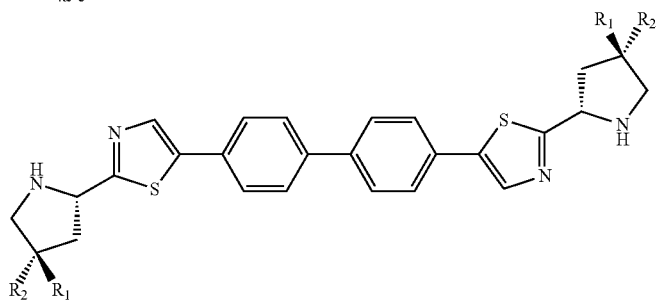
5a-c
a: $R_1$ = H; $R_2$ = H
b: $R_1$ = F; $R_2$ = H
c: $R_1$ = H; $R_2$ = F
Scheme 8 below illustrates another modified method for preparing multicyclic compounds of this invention. In this synthetic route, 4,4'-bis(2-((S)-pyrrolidin-2-yl)thiazol-5-yl) biphenyl (compound 5a in scheme 1), the essentially intermediate, is coupled with compound 93 or 94 to afford analogues 95a-105a and 106a-114a.
Scheme 8
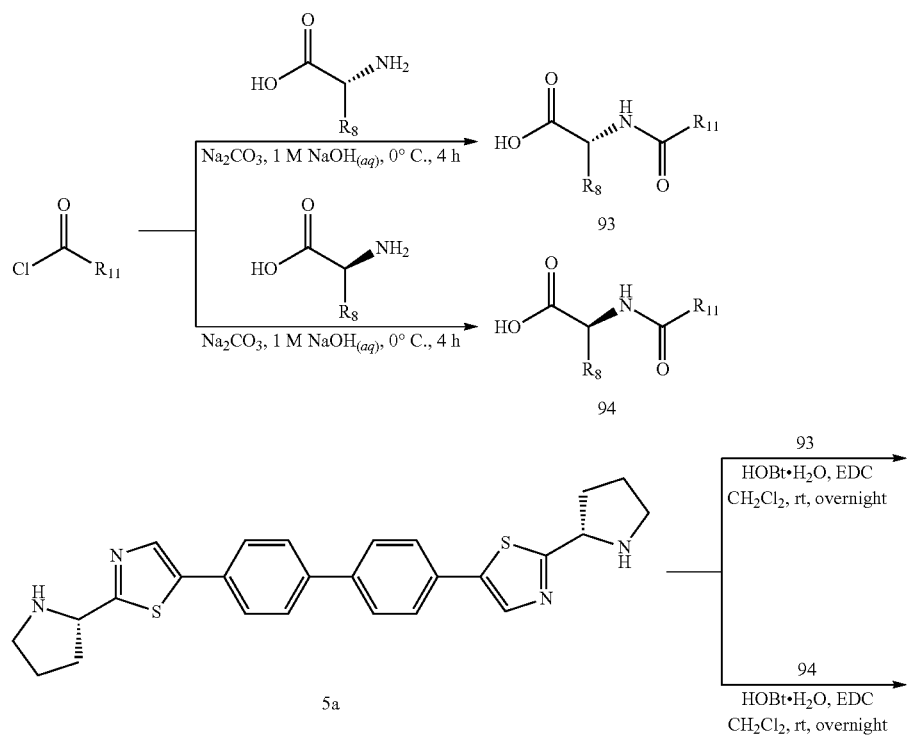

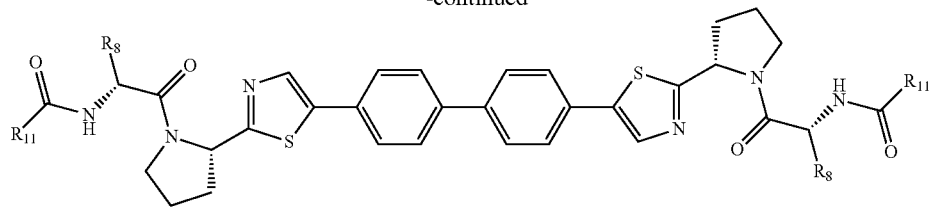
95a-105a
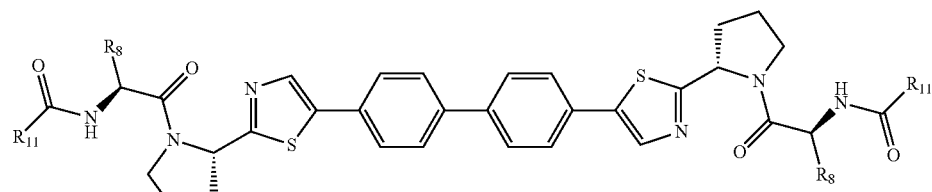
106a-114a
Scheme 9 below shows a method for synthesizing dithiazolylbiphenyl 119a, a stereoisomer of dithiazolylbiphenyl 5a.
Scheme 9
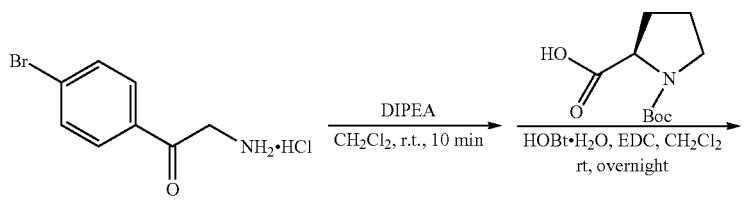
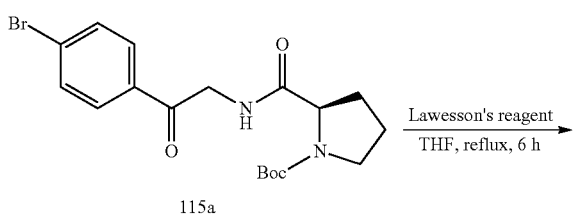
115a
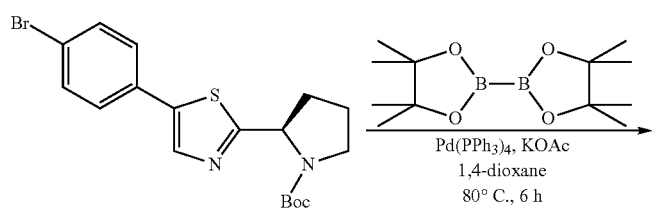
116a

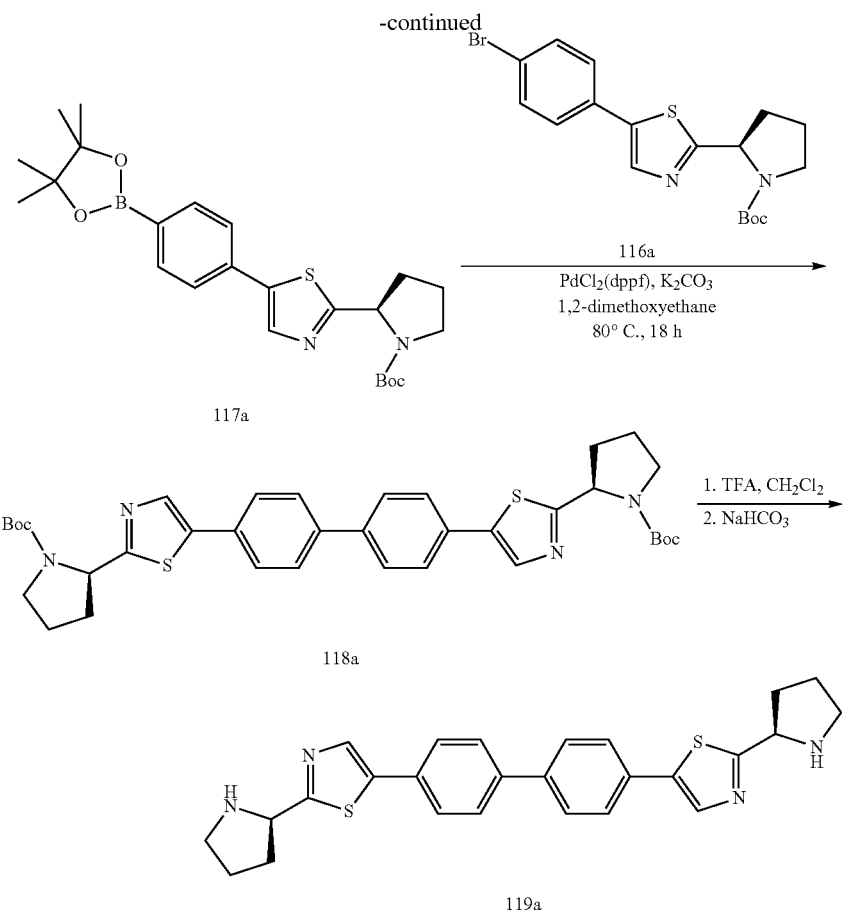
Scheme 10 shown below illustrates synthesizing dithiazolylbiphenyl peptides 6a, 120a, 121a, and 122a from compound 5a and 119a via peptide coupling conditions (e.g., HOBt·H₂O and EDC). These dithiazolylbiphenyl peptides are deprotected and subsequently reacted with various alkyl or aryl acetyl chlorides to produce desired compounds 7a and 123a-127a.
Scheme 10
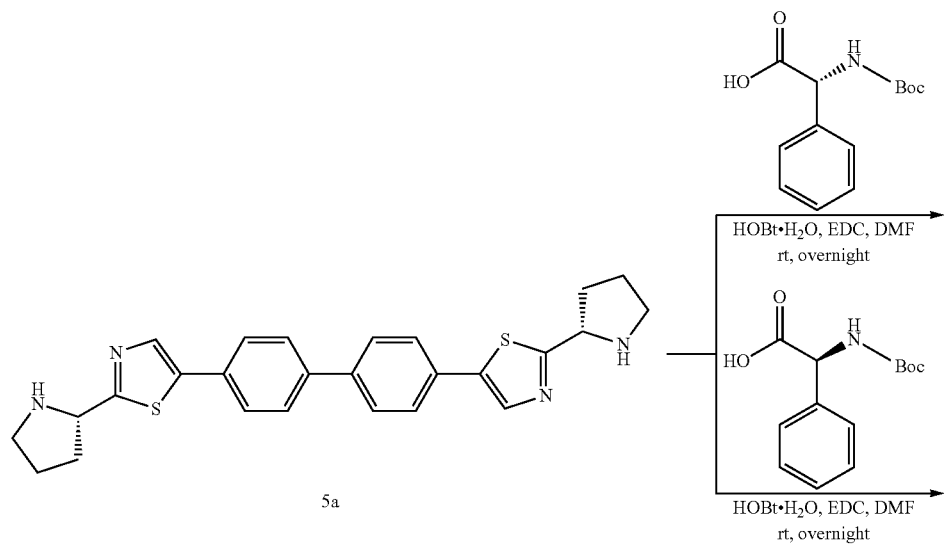

-continued
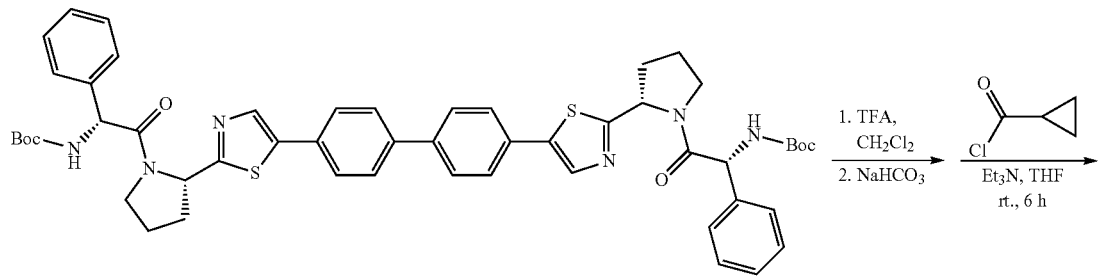
6a
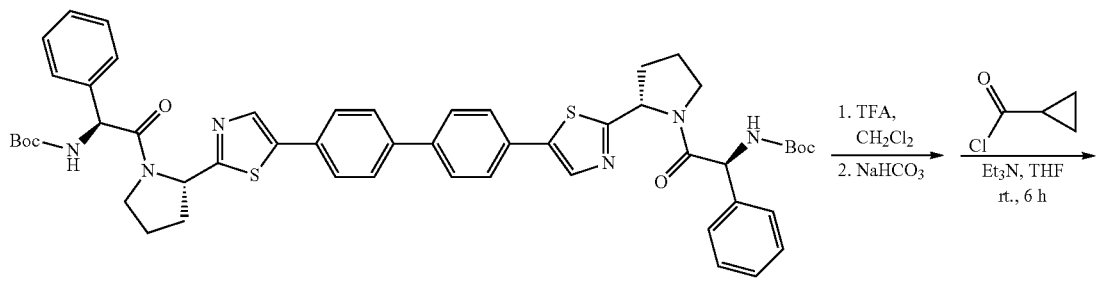
120a
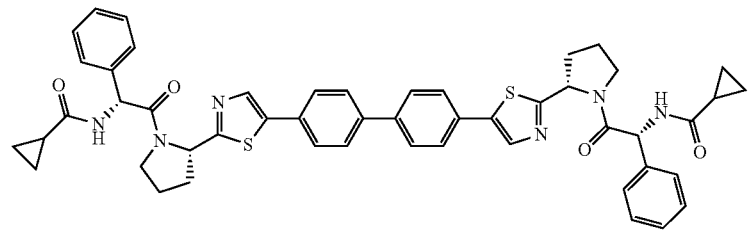
7a-A
+
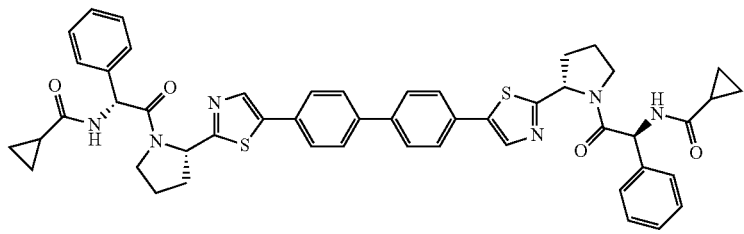
124a

-continued
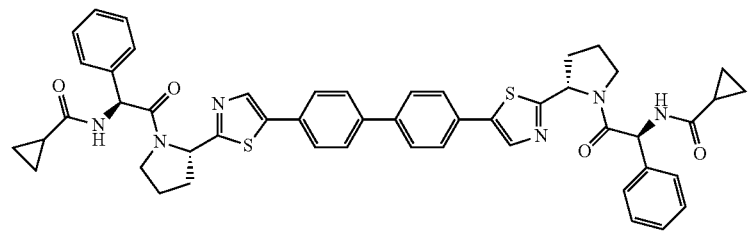
123a
+
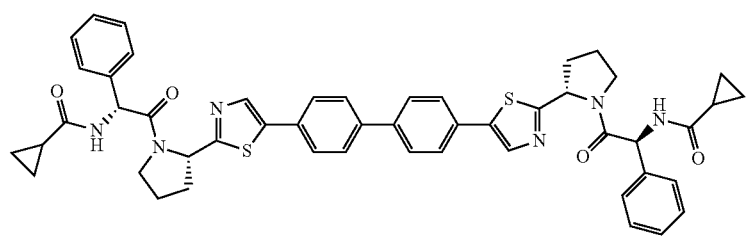
124a
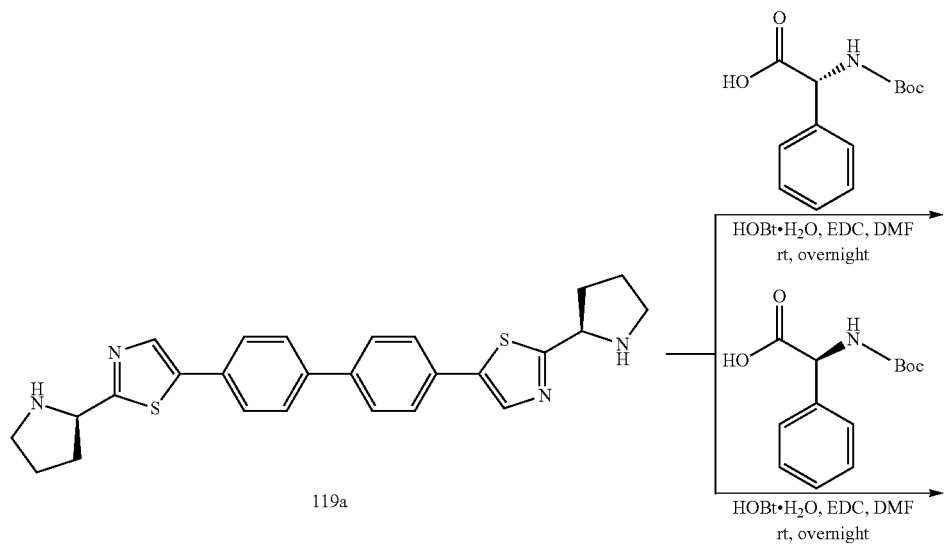

-continued
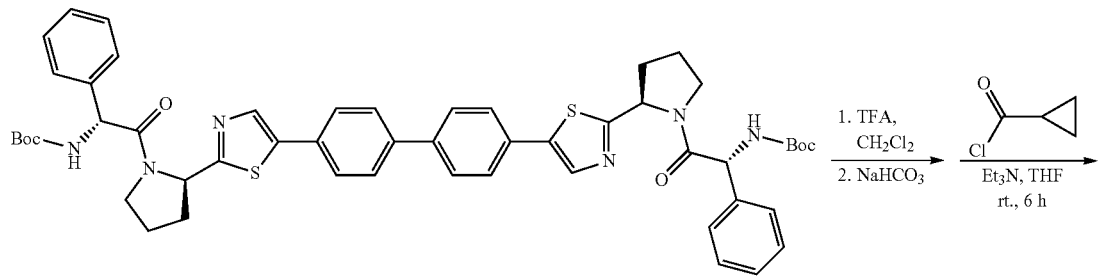
121a
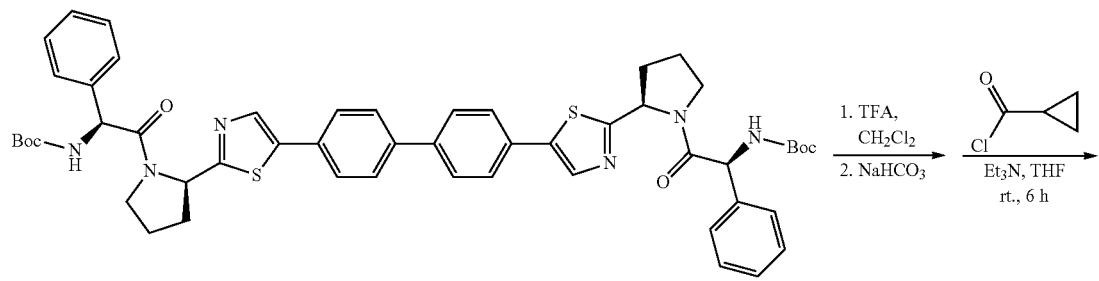
122a
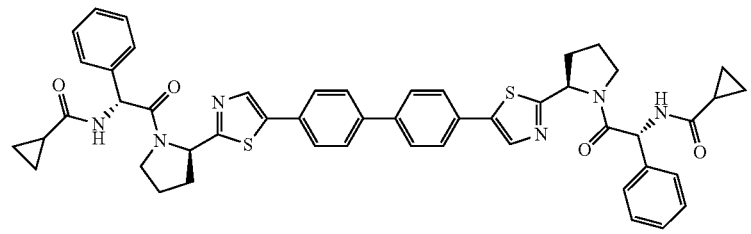
125a
+
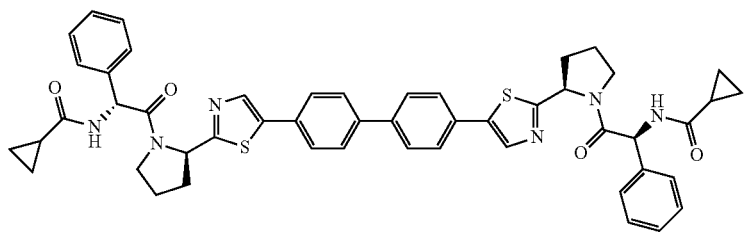
127a

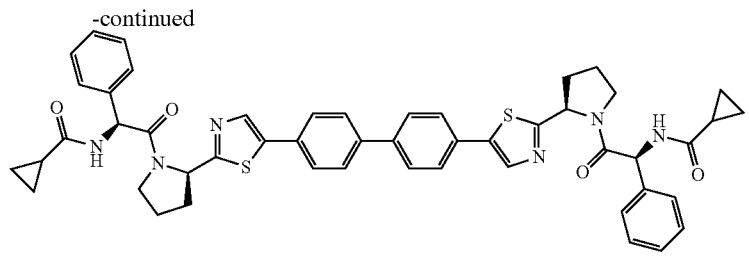

126a

+

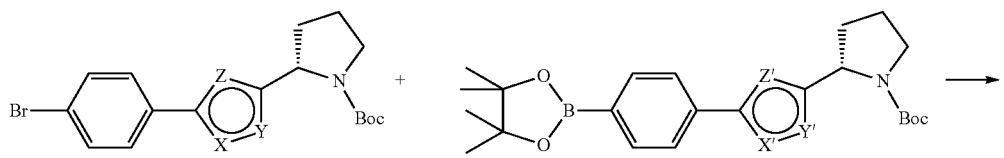

127a

Schemes 11-13 below show typical synthetic routes to multicyclic compounds of this invention. Aryl bromides (e.g., 12a~c, 16a~c, or 21a~c above) are reacted with arylboronic esters (e.g., 13a~c, 20a~c, or 22a~c above) under Suzuki-Miayura coupling conditions to construct the N-protected asymmetric biphenyl compounds 23a~c (as shown in Schemes 7-9). N-deprotection of pyrrolidine moieties in trifluoroacetic acid at room temperature yield N-deprotected derivatives 24a~c, which are then coupled with N-Boc-D-phenylglycine to afford the asymmetric biphenyl compounds 25a~c. In one-step fashion, 25a~c can be treated with trifluoroacetic acid, and then be reacted with various alkyl or aryl acetyl chlorides to give the final acylated products 26a~c. Similarly, other substituted compounds (e.g., 30a~c, 34a~c, 38a~c, 42a~c, and 46a~c shown in Schemes 11-13 below) can be prepared.

Scheme 11

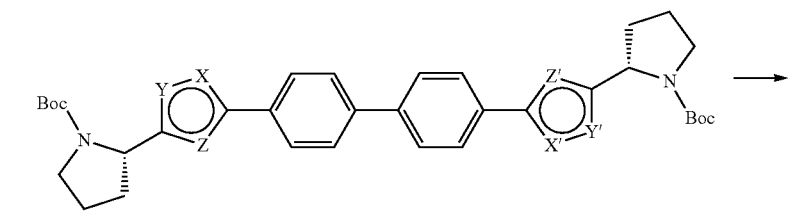

16a: X = N, Y = O, Z = N
16a: X = N, Y = O, Z = N
16a: X = N, Y = O, Z = N
12a: X = CH, Y = S, Z = N
21a: X = CH, Y = N, Z = S
21a: X = CH, Y = N, Z = S

20a: X' = CH, Y' = NH, Z' = N
13a: X' = CH, Y' = S, Z = N
22a: X' = CH, Y' = N, Z' = S
20a: X' = CH, Y' = NH, Z' = N
20a: X' = CH, Y' = NH, Z' = N
13a: X' = CH, Y' = S, Z' = N

23a: X = N, Y = O, Z = N; X' = CH, Y' = NH, Z' = N
27a: X = N, Y = O, Z = N; X' = CH, Y' = S, Z' = N
31a: X = N, Y = O, Z = N; X' = CH, Y' = N, Z' = S
35a: X = CH, Y = S, Z = N; X' = CH, Y' = NH, Z' = N
39a: X = CH, Y = N, Z = S; X' = CH, Y' = NH, Z' = N
43a: X = CH, Y = N, Z = S; X' = CH, Y' = S, Z' = N

-continued

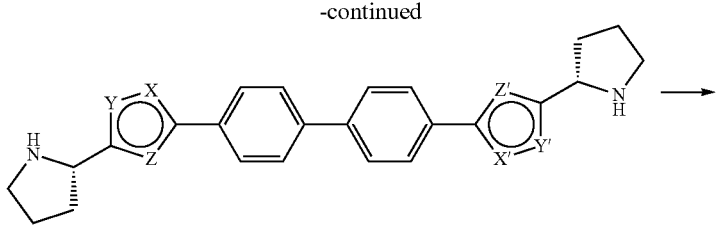

24a: X = N, Y = O, Z = N; X' = CH, Y' = NH, Z' = N
28a: X = N, Y = O, Z = N; X' = CH, Y' = S, Z' = N
32a: X = N, Y = O, Z = N; X' = CH, Y' = N, Z' = S
36a: X = CH, Y = S, Z = N; X' = CH, Y' = NH, Z' = N
40a: X = CH, Y = N, Z = S; X' = CH, Y' = NH, Z' = N
44a: X = CH, Y = N, Z = S; X' = CH, Y' = S, Z' = N

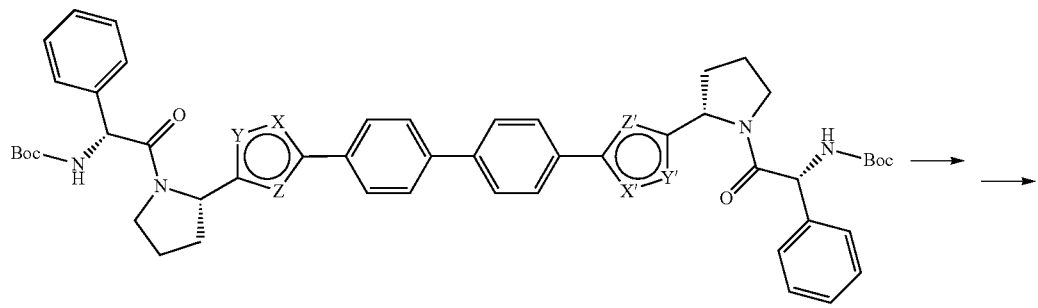

25a: X = N, Y = O, Z = N; X' = CH, Y' = NH, Z' = N
29a: X = N, Y = O, Z = N; X' = CH, Y' = S, Z' = N
33a: X = N, Y = O, Z = N; X' = CH, Y' = N, Z' = S
37a: X = CH, Y = S, Z = N; X' = CH, Y' = NH, Z' = N
41a: X = CH, Y = N, Z = S; X' = CH, Y' = NH, Z' = N
45a: X = CH, Y = N, Z = S; X' = CH, Y' = S, Z' = N

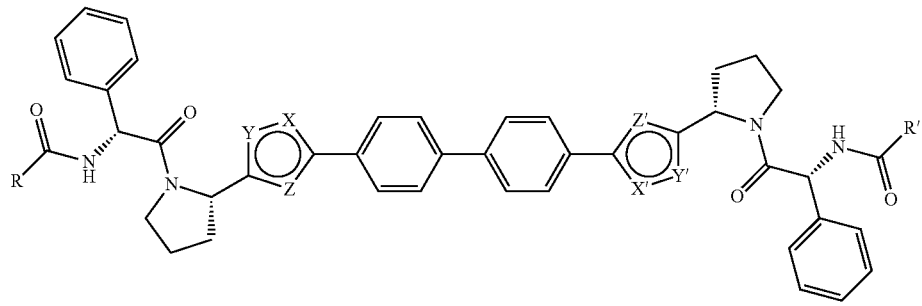

26a: X = N, Y = O, Z = N; X' = CH, Y' = NH, Z' = N
30a: X = N, Y = O, Z = N; X' = CH, Y' = S, Z' = N
34a: X = N, Y = O, Z = N; X' = CH, Y' = N, Z' = S
38a: X = CH, Y = S, Z = N; X' = CH, Y' = NH, Z' = N
42a: X = CH, Y = N, Z = S; X' = CH, Y' = NH, Z' = N
46a: X = CH, Y = N, Z = S; X' = CH, Y' = S, Z' = N

R = R' = cycloalkyl, cycloalkenyl, heterocycloalkyl, or heterocycloalkenyl

Scheme 12
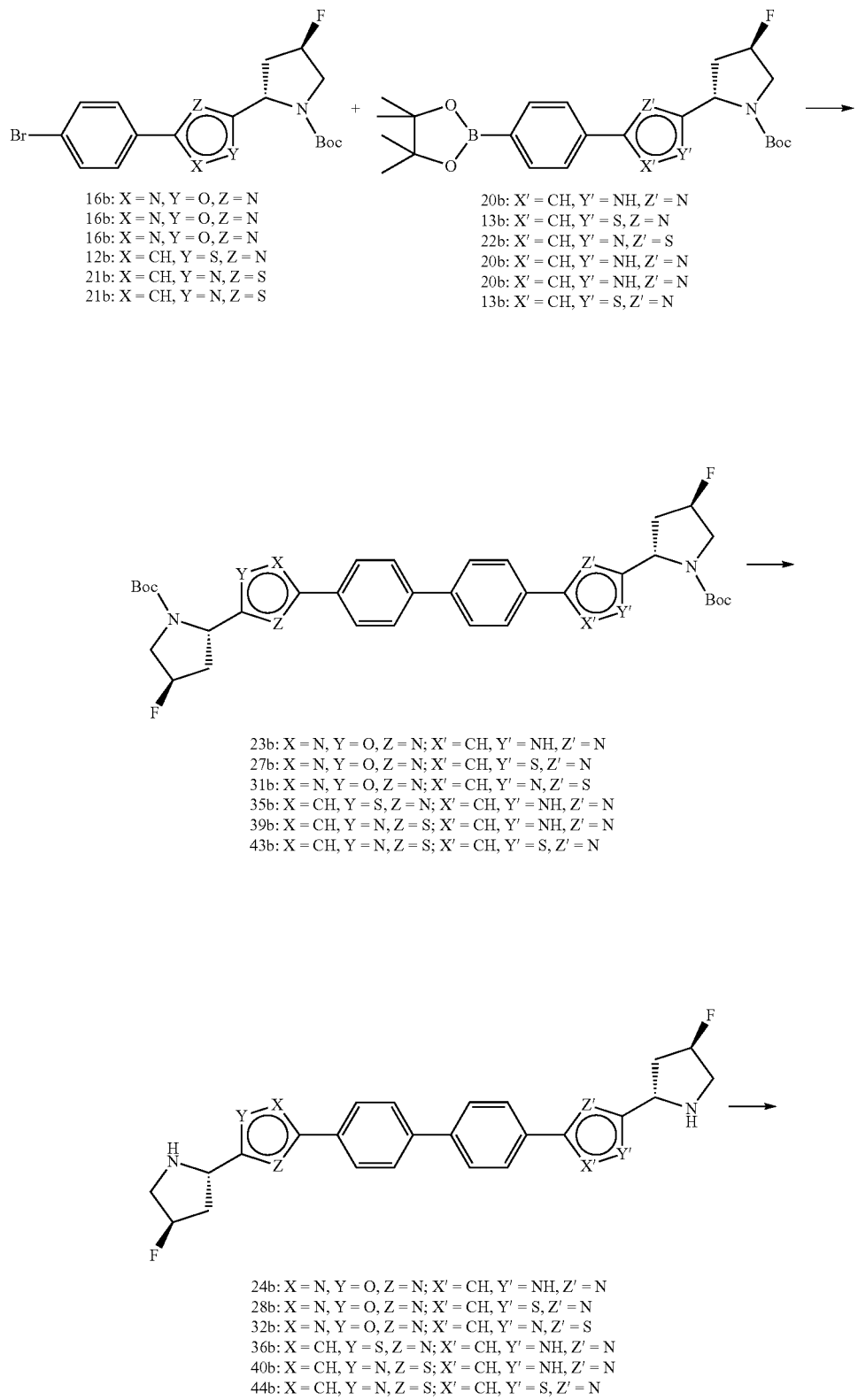

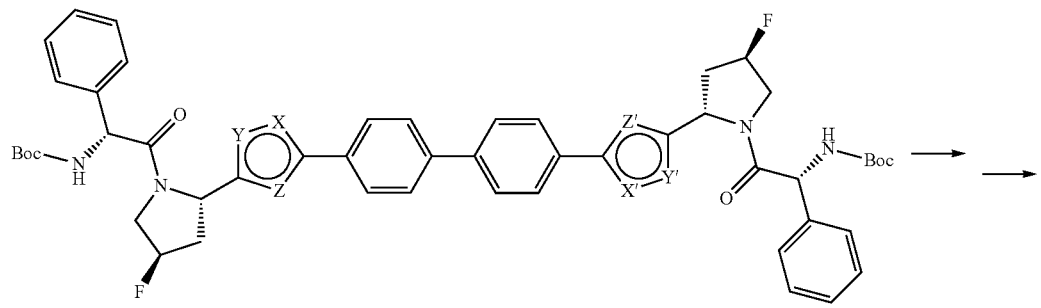

25b: X = N, Y = O, Z = N; X' = CH, Y' = NH, Z' = N
29b: X = N, Y = O, Z = N; X' = CH, Y' = S, Z' = N
33b: X = N, Y = O, Z = N; X' = CH, Y' = N, Z' = S
37b: X = CH, Y = S, Z = N; X' = CH, Y' = NH, Z' = N
41b: X = CH, Y = N, Z = S; X' = CH, Y' = NH, Z' = N
45b: X = CH, Y = N, Z = S; X' = CH, Y' = S, Z' = N

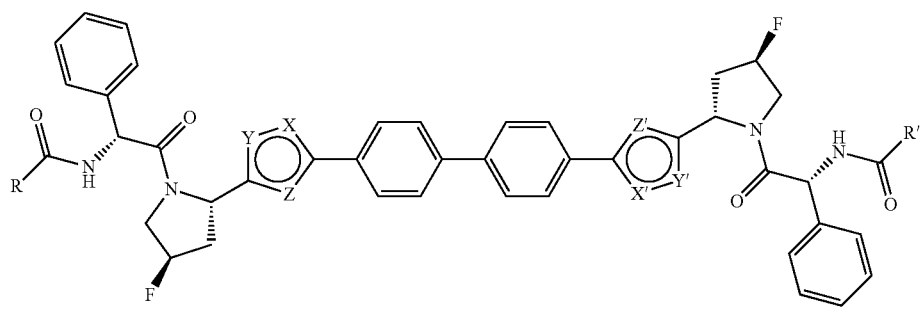

26b: X = N, Y = O, Z = N; X' = CH, Y' = NH, Z' = N
30b: X = N, Y = O, Z = N; X' = CH, Y' = S, Z' = N
34b: X = N, Y = O, Z = N; X' = CH, Y' = N, Z' = S
38b: X = CH, Y = S, Z = N; X' = CH, Y' = NH, Z' = N
42b: X = CH, Y = N, Z = S; X' = CH, Y' = NH, Z' = N
46b: X = CH, Y = N, Z = S; X' = CH, Y' = S, Z' = N

R = R' = cycloalkyl, cycloalkenyl, heterocycloalkyl, or heterocycloalkenyl

Scheme 13

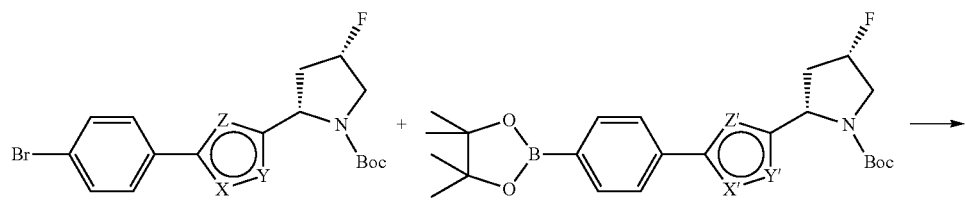

16c: X = N, Y = O, Z = N
16c: X = N, Y = O, Z = N
16c: X = N, Y = O, Z = N
12c: X = CH, Y = S, Z = N
21c: X = CH, Y = N, Z = S
21c: X = CH, Y = N, Z = S

20c: X' = CH, Y' = NH, Z' = N
13c: X' = CH, Y' = S, Z = N
22c: X' = CH, Y' = N, Z = S
20c: X' = CH, Y' = NH, Z' = N
20c: X' = CH, Y' = NH, Z' = N
13c: X' = CH, Y' = S, Z' = N

-continued

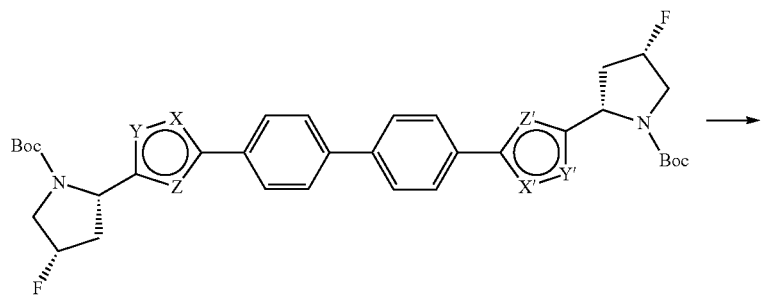

23c: X = N, Y = O, Z = N; X' = CH, Y' = NH, Z' = N
27c: X = N, Y = O, Z = N; X' = CH, Y' = S, Z' = N
31c: X = N, Y = O, Z = N; X' = CH, Y' = N, Z' = S
35c: X = CH, Y = S, Z = N; X' = CH, Y' = NH, Z' = N
39c: X = CH, Y = N, Z = S; X' = CH, Y' = NH, Z' = N
43c: X = CH, Y = N, Z = S; X' = CH, Y' = S, Z' = N

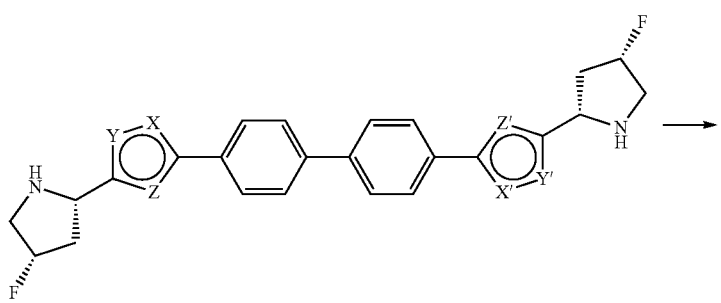

24c: X = N, Y = O, Z = N; X' = CH, Y' = NH, Z' = N
28c: X = N, Y = O, Z = N; X' = CH, Y' = S, Z' = N
32c: X = N, Y = O, Z = N; X' = CH, Y' = N, Z' = S
36c: X = CH, Y = S, Z = N; X' = CH, Y' = NH, Z' = N
40c: X = CH, Y = N, Z = S; X' = CH, Y' = NH, Z' = N
44c: X = CH, Y = N, Z = S; X' = CH, Y' = S, Z' = N

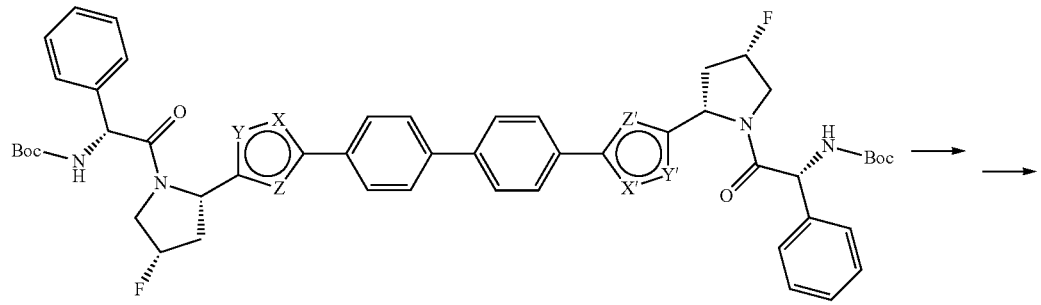

25c: X = N, Y = O, Z = N; X' = CH, Y' = NH, Z' = N
29c: X = N, Y = O, Z = N; X' = CH, Y' = S, Z' = N
33c: X = N, Y = O, Z = N; X' = CH, Y' = N, Z' = S
37c: X = CH, Y = S, Z = N; X' = CH, Y' = NH, Z' = N
41c: X = CH, Y = N, Z = S; X' = CH, Y' = NH, Z' = N
45c: X = CH, Y = N, Z = S; X' = CH, Y' = S, Z' = N

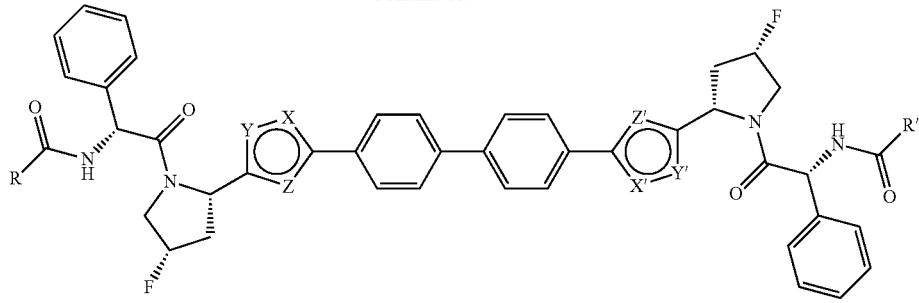

26c: X = N, Y = O, Z = N; X' = CH, Y' = NH, Z' = N
30c: X = N, Y = O, Z = N; X' = CH, Y' = S, Z' = N
34c: X = N, Y = O, Z = N; X' = CH, Y' = N, Z' = S
38c: X = CH, Y = S, Z = N; X' = CH, Y' = NH, Z' = N
42c: X = CH, Y = N, Z = S; X' = CH, Y' = NH, Z' = N
46c: X = CH, Y = N, Z = S; X' = CH, Y' = S, Z' = N

R = R' = cycloalkyl, cycloalkenyl, heterocycloalkyl, or heterocycloalkenyl

The compounds of this invention can also be synthesized in manners similar to those outlined in Schemes 1-13 with necessary modifications as recognized by those skilled in the art.

Compounds thus synthesized can be further purified by flash column chromatography, high performance liquid chromatography, crystallization, or any other suitable methods.

The compounds mentioned herein contain asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of any compound of this invention and a pharmaceutically acceptable carrier, and (2) a method for treating 1-10/infection by administering to a subject in need of this treatment an effective amount of such a compound.

As used herein, the term "treating" refers to administering a compound to a subject that has HCV infection, or has a symptom of or a predisposition toward such a disorder, with the purpose to cure, heal, alleviate, relieve, alter, remedy, ameliorate, improve, or affect the above-described disorder, the symptoms of or the predisposition toward it. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

The compounds described above can be preliminarily screened for their efficacy in treating above-described diseases by an in vitro assay and then confirmed by animal experiments and clinic trials. Other methods will also be apparent to those of ordinary skill in the art.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of (S)-tert-butyl 2-(2-(4-bromophenyl)-2-oxoethylcarbamoyl)pyrrolidine-1-carboxylate (1a)

A solution of N-Boc-L-Proline (5.16 g, 24.0 mmol) and HOBt.H$_2$O (3.67 g, 24.0 mmol) was stirred at room temperature for 10 min and then treated with N-ethyl-N'-(3-dimethylaminopropyl) carbodiimide hydrochloride (EDC.HCl, 4.60 g, 24.0 mmol). The resulting mixture was stirred at room temperature for 30 min and then treated with a yellow solution formed by stirring 2-amino-4'-bromoacetophenone hydrochloride (5.0 g, 20.0 mmol) and N,N-diisopropylethylamine (DIPEA, 2.58 g, 20 mmol) in dichloromethane (DCM, 150 ml) at room temperature for 10 min. The resulting mixture was stirred at room temperature overnight and then filtered through Celite® to remove the precipitate. The filtrate was extracted with DCM and H$_2$O. The organic layer was washed with brine, dried over MgSO$_4$, filtered, and concentrated. The residue was purified with column chromatography (ethyl acetate:hexanes=2:5) to yield pure product 1a as a yellow gel (7.39 g, 90%).

Example 2

Synthesis of (S)-tert-butyl 2-(5-(4-bromophenyethiazol-2-yl)pyrrolidine-1-carboxylate (2a)

To a solution of the ketoamide substrate 1a (25.26 g, 61.42 mmol) in tetrahydrofuran (THF, 300 ml) was added Lawesson's reagent (37.21 g, 92.11 mmol). The resulting mixture was refluxed for 6 hours, cooled to room temperature, and concentrated in vacuo. The residue was purified over silica column chromatography (ethyl acetate:hexanes=1:2) to provide product 2a as a yellow solid (19.6 g, 78%).

Example 3

Synthesis of (S)-tert-butyl 2-(5-(4-(4,4,5,5-tetramethyl-1,3,2-dioxaborolan-2-yl)phenyl)thiazol-2-yl)pyrrolid-ine-1-carboxylate (3a)

A flask charged with Pd(PPh$_3$)$_4$ (0.49 g, 0.43 mmol), potassium acetate (2.09 g, 21.37 mmol), and bis(pinacolato)diboron (5.16 g, 17.1 mmol), compound 2a (3.50 g, 8.55 mmol) and 1,4-dioxane (100 mL) was flushed with nitrogen. The reaction mixture was then stirred at 80° C. for 6 hours. After cooling to ambient temperature, the resulting mixture was filtered. The filtrate was concentrated under reduced pressure and the residue was purified by flash chromatography (ethyl acetate:hexanes=1:2) to give product 3a as a yellow gel (3.88 g, 99%).

Example 4

Synthesis of (2S,2'S)-di-tert-butyl-2,2'-(5,5'-(biphenyl-4,4'-diyl)bis(thiazole-5,2-diyl))dipyrrolidine-1-carboxyl-ate (4a)

A flask charged with PdCl$_2$(dppf) (0.48 g, 0.59 mmol), potassium carbonate (5.87 g, 42.5 mmol), 2a (3.75 g, 9.16 mmol), 3a (3.88 g, 8.5 mmol), and 1,2-dimethoxyethane (100 mL) was flushed with nitrogen. The reaction mixture was then stirred at 80° C. for 18 hrs. After cooling to ambient temperature, the resulting mixture was filtered. The filtrate was concentrated under reduced pressure and the residue was then purified by column chromatography (ethyl acetate:hexanes=1:2) to yield pure product 4a as a yellow gel (2.66 g, 47%).

Example 5

Synthesis of 4,4'-bis(2-((S)-pyrrolidin-2-yl)thiazol-5-yl)biphenyl (5a)

To a solution of compound 4a (2.66 g, 4.04 mmol) in DCM at room temperature was added trifluoroacetic acid. The resulting reaction mixture was stirred for 2 hours, and then concentrated under reduced pressure to give a viscous liquid. To this liquid were added distilled water and DCM, and the resulting mixture was cooled with an ice bath and saturated sodium bicarbonate solution was added until pH=8. The mixture was extracted with DCM (40 mL×8). The combined organic layers were dried over MgSO$_4$, filtered, and concentrated. The residue was purified by flash column chromatography (100% ethyl acetate, then methanol:DCM=1:20) to give pure product 5a (1.83 g, 99%).

Example 6

Synthesis of di-tert-butyl (1R,1'R)-2,2'-((2S,2'S)-2,2'-(5,5'-(biphenyl-4,4'-diyl)bis(thiazole-5,2-diyl))bis(pyrro-lidine-2,1-diyl))bis(2-oxo-1-phenylethane-2,1-diyl)dicarbamate (6a)

To a solution of N-Boc-D-phenylglycine (2.21 g, 8.8 mmol) in DMF (30 ml) was added HOBt.H$_2$O (1.35 g, 8.8 mmol) in one portion at room temperature. After the mixture was stirred at temperature for 10 min, EDC (1.68 g, 8.8 mmol) was added and the resulting mixture was stirred for 30 min. A solution of compound 5a (1.83 g, 4.0 mmol) in DMF (20 mL) was then added. The resulting mixture was stirred overnight at room temperature and then extracted with EtOAc and water (to remove HOBt salts). The organic layer was dried over MgSO$_4$, filtered, and concentrated. The residue was purified by column chromatography on silica gel (methanol:DCM=1:20) to yield product 6a as a white solid (2.77 g, 75%).

Example 7

Synthesis of N,N'-(1R,1'R)-2,2'-((2S,2'S)-2,2'-(5,5'-(biphenyl-4,4'-diyl)bis(thiazole-5,2-diyl))bis(pyrrolidine-2,1-diyl))bis(2-oxo-1-phenylethane-2,1-diyl) dicyclopropanecarboxamide (7a-A)

To a solution of Compound 6a (2.77 g, 3.0 mmol) in DCM (25 mL) was added trifluoroacetic acid (5 mL) at room temperature. The reaction was stirred for 2 hours. After the reaction was completed, it was cooled with an ice bath and saturated sodium bicarbonate solution was added until pH=7~8.

The resulting mixture was extracted with DCM (20 mL×8). The organic layer was dried over MgSO$_4$, filtered, and concentrated. The crude product was used as the starting material for the next step without further purification. A solution of the crude product in THF (20 mL) was cooled with an ice bath, cyclopropanecarbonyl chloride (208 mg, 1.99 mmol) and triethylamine (126 mg, 1.24 mmol) were added. The ice bath was removed and the resulting mixture was stirred at room temperature for 10 min and concentrated under reduced pressure. The residue was extracted with ethyl acetate (10 mL×4). The combined organic layers were washed with brine, dried over MgSO$_4$, filtered and concentrated. The residue was purified by column chromatography on silica gel (MeOH: DCM=1:99) to afford final product 7a-A (390 mg, 54%). LC/MS (ESI): [M+2]$^+$/2: 431, [M+1]$^+$: 861, [M+23]$^+$: 883.

Example 8

Synthesis of (9-tea-butyl 2-carbamoylpyrrolidine-1-carboxylate (10a)

N-Boc-L-proline (5.0 g, 23.2 mmol) was dissolved in 1,4-dioxane (110 ml) at room temperature. To the proline solution were added pyridine (1.1 mL, 13.9 mmol), di-tert-butyl dicarbonate (6.6 g, 30.2 mmol), and ammonium carbonate (2.9 g, 30.2 mmol). The reaction mixture was then stirred at room temperature for 19 hours. The resulting mixture was evaporated under reduced pressure to remove volatile components. To the residue, ethyl acetate (50 ml), 20% aqueous citric acid (100 ml), and brine (50 ml) were added. The mixture was stirred at room temperature for 5 min. The aqueous layer was extracted with ethyl acetate and the organic layer was combined, dried over MgSO$_4$, and filtered. The filtrate was concentrated to yield crude product. And then purified with column chromatography (dichloromethane:methanol=9:1) to give 10a (4.5 g).

Example 9

Preparation of (S)-tert-butyl 2-carbamothioylpyrrolidine-1-carboxylate (11a)

A round-bottomed flask with (S)-tert-butyl 2-carbamoylpyrrolidine-1-carboxylate (compound 10a, 3.0 g, 14.0 mmol) and Lawesson's reagent (6.8 g, 16.8 mmol) was flushed with nitrogen. Dry THF (40 ml) was added as the solvent. The reaction mixture was stirred at 70° C. under nitrogen for 8 hours. After cooled to room temperature, the resulting mixture was evaporated under reduced pressure and purified by column chromatography (ethyl acetate:n-hexane=1:2) to yield pure product 11a (2.7 g).

Example 10

Preparation of (S)-tert-butyl 2-(4-(4-bromophenyl) thiazol-2-yl)pyrrolidine-1-carboxylate (12a)

A solution of (S)-tert-butyl 2-carbamothioylpyrrolidine-1-carboxylate (compound 11a, 2.2 g, 9.6 mmol) and 4-bromophenacyl bromide (2.9 g, 10.5 mmol) in ethanol (50 ml) was stirred at room temperature for 3 hours. The resulting mixture was extracted with ethyl acetate and the organic layer was dried over MgSO$_4$, filtered and concentrated to give crude product. The crude product was purified with column chromatography (ethyl acetate:n-hexane=1:3) to yield pure product 12a (3.3 g).

Example 11

Preparation of (S)-tert-butyl 2-(4-(4-(4,4,5,5-tetramethyl-1,3,2-dioxaborolan-2-yl)phenyl) thiazol-2-yl) pyrrolidine-1-carboxylate (13a)

A round-bottomed flask charged with bis(pinacolato)diboron (1.1 g, 4.4 mmol), Pd(PPh$_3$)$_4$ (0.13 g, 0.11 mmol), and K$_2$CO$_3$ (1.5 g, 11.0 mmol) was flushed with nitrogen at room temperature. A solution of (S)-tert-butyl 2-(2-(4-bromophenyl)thiazol-2-yl)pyrrolidine-1-carboxylate (compound 12a, 1.5 g, 3.7 mmol) in DMSO (20 mL) was added. The reaction was stirred at 80° C. overnight. After cooled to room temperature, the resulting mixture was extracted with ethyl acetate/H$_2$O, dried over MgSO$_4$, filtered, and concentrated to give a yellow liquid. The crude product was purified by column chromatography (ethyl acetate:n-hexane=1:5) to yield product 13a as a white solid (1.1 g).

Example 12

Preparation of 4-bromo-N'-hydroxybenzimidamide (15)

To a solution of 4-bromobenzonitrile (5.0 g, 27.5 mmol) in ethanol (42 ml) at room temperature, hydroxylamine hydrochloride (1.91 g, 27.5 mmol) and DIPEA (4.8 ml, 27.5 mmol) were added. The reaction mixture was stirred at 90° C. for 5 hours. After cooled to room temperature, the resulting mixture was concentrated to yield a colorless viscous liquid. The liquid was extracted with ethyl acetate and the organic layer was dried over magnesium sulfate, filtered and then concentrated to give a crude compound, which was washed with n-hexane to yield product 15 as a white solid (5.0 g).

Example 13

Preparation of (S)-tert-butyl 2-(3-(4-bromophenyl)-1,2,4-oxadiazol-5-yl)pyrrolidine-1-carboxylate (16a)

To a solution of N-Boc-L-proline (2.5 g, 11.6 mmol) in N,N-dimethylformamide (18 mL), O-(Benzotriazol-1-yl)-N,N,N',N'-tetra methyluronium tetrafluoroborate (TBTU, 3.73 g, 11.6 mmol), HOBt.H$_2$O (0.36 g, 2.32 mmol) and DIPEA (10.2 ml, 58.1 mmol) were added. After the reaction mixture was stirred at room temperature for 5 minutes, 4-Bromo-N'-hydroxybenzimidamide 15 (2.5 g, 11.6 mmol) was added. The mixture was then stirred at 110° C. for 2.5 hours. After cooled to room temperature, the resulting mixture was extracted with ethyl acetate, dried over magnesium sulfate, filtered and concentrated to yield a crude yellow liquid, which was purified with chromatography (ethyl acetate: n-hexane=1:10) to give the desired product 16a (2.5 g).

Example 14

Preparation of (S)-tert-butyl 2-(2-(4-bromophenyl)-2-oxoethylcarbamoyl)pyrrolidine-1-carboxylate (18a)

To a suspension of 2-amino-4'-bromoacetophenone hydrochloride 17 (5.0 g, 20.0 mmol) in DCM (150 mL) was added DIPEA (2.6 g, 20 mmol) at room temperature. After stirred for 10 minutes, the suspension became yellow solution. To another flask charged with a DCM (100 mL) solution of N-Boc-L-Proline (5.2 g, 24.0 mmol) was added HOBt.H$_2$O (3.7 g, 24.0 mmol) at room temperature. EDC.HCl (4.6 g, 24.0 mmol) was added to the proline mixture and the mixture was continually stirred at room temperature for 30 minutes. The above-mentioned yellow solution was added to the proline mixture and stirred at room temperature overnight. The resulting mixture was filtered through Celite® to remove the precipitate. The filtrate was extracted with $H_2O$/DCM, and the organic layer was washed with brine, dried over $MgSO_4$, and filtered. After being concentrated under reduced pressure, the crude product was purified by column chromatography (ethyl acetate: n-hexane=2:5) to yield pure product 18a as a yellow gel (7.4 g).

Example 15

Preparation of (S)-tert-butyl 2-(5-(4-bromophenyl)-1H-imidazol-2-yl)pyrrolidine-1-carboxylate (19a)

To the solution of (S)-tert-butyl 2-(2-(4-bromophenyl)-2-oxoethylcarbamoyl)pyrrolidine-1-carboxylate (compound 18a, 5.0 g, 12.2 mmol) in xylene (75 ml) were added ammonium acetate (23.4 g, 304 mmol) and acetic acid (5 ml) at room temperature. The reaction mixture was placed in an oil bath and heated to 160° C. with water being azeotroped into a Dean-Stark trap. After 3 hours, the resulting mixture was cooled to room temperature and then extracted with ethyl acetate and distillated water. The organic layer was dried over $MgSO_4$, filtered, and concentrated under reduced pressure to give a crude product, which was purified with column chromatography (100% ethyl acetate) to yield the pure product 19a (4.4 g).

Example 16

Preparation of (S)-tert-butyl 2-(5-(4-(4,4,5,5-tetramethyl-1,3,2-dioxaborolan-2-yl)phenyl)-1H-imidazol-2-yl)pyrrolidine-1-carboxylate (20a)

A round-bottomed flask charged with bis(pinacolato)diboron (0.8 g, 3.2 mmol), $Pd(PPh_3)_4$ (0.06 g, 0.05 mmol) and KOAc (0.37 g, 3.81 mmol) was flushed with nitrogen at room temperature and to this was added a solution of (S)-tert-butyl 2-(5-(4-bromophenyl)-1H-imidazol-2-yl)pyrrolidine-1-carboxylate (compound 19a, 0.5 g, 1.3 mmol) in 1,4-dioxane (15 ml). The reaction mixture was stirred at 80° C. overnight and then cooled to room temperature. The resulting mixture was extracted with ethyl acetate and distillated water. The organic layer was dried over $MgSO_4$, filtered and concentrated under reduced pressure to give a crude yellow liquid, which was then purified via column chromatography (ethyl acetate: n-hexane=2:1) to yield product 20a as a white solid (0.53 g).

Example 17

Preparation of (S)-tert-butyl 2-(5-(4-bromophenyl) thiazol-2-yl)pyrrolidine-1-carboxylate (21a)

Compound 21a was prepared in a manner similar to that described in Example 2.

Example 18

Preparation of (S)-tert-butyl 2-(5-(4-(4,4,5,5-tetramethyl-1,3,2-dioxaborolan-2-yl)phenyl) thiazol-2-yl) pyrrolidine-1-carboxylate (22a)

Compound 22a was prepared from Compound 21a in a manner similar to that described in Example 3.

Example 19

Preparation of (S)-tert-butyl 2-(4-(4'-(5-((S)-1-(tert-butoxycarbonyl)pyrrolidin-2-yl)-1,2,4-oxadiazol-3-yl)biphenyl-4-yl)-1H-imidazol-2-yl)pyrrolidine-1-carboxylate (23a)

A flask charged with $PdCl_2$(dppf) (0.04 g, 0.051 mmol), sodium bicarbonate (0.37 g, 4.45 mmol), and (S)-tert-butyl 2-(3-(4-bromophenyl)-1,2,4-oxadiazol-5-yl)pyrrolidine-1-carboxylate (compound 16a, 0.50 g, 1.27 mmol) was flushed with nitrogen. A solution of (S)-tert-butyl 2-(5-(4-(4,4,5,5-tetramethyl-1,3,2-dioxaborolan-2-yl)phenyl)-1H-imidazol-2-yl)pyrrolidine-1-carboxylate (compound 20a, 0.67 g, 1.52 mmol) in 1,2-dimethoxyethane (15 ml) was then added. The reaction mixture was stirred at 80° C. under nitrogen for 6 hours. After cooled to room temperature, the resulting mixture was extracted with ethyl acetate/water, dried over magnesium sulfate, filtered and concentrated to give a crude compound, which was purified with chromatography (ethyl acetate: n-hexane=4:1) to yield product 23a as a white solid (0.57 g).

Example 20

Preparation of 5-((S)-pyrrolidin-2-yl)-3-(4'-(2-((S)-pyrrolidin-2-yl)-1H-imidazol-4-yl)biphenyl-4-yl)-1,2,4-oxadiazole (24a)

Compound 24a was prepared from Compound 23a in a manner similar to that described in Example 5.

Example 21

Preparation of Compound 25a

To a solution of N-Boc-D-phenylglycine (0.29 g, 1.15 mmol) in DCM (10 mL) at room temperature, $HOBt.H_2O$ (0.18 g, 1.15 mmol) was added in one portion. The mixture was stirred for 10 minutes and EDC (0.22 g, 1.15 mmol) was added. After 10 minutes, 5-((S)-pyrrolidin-2-yl)-3-(4'-(2-((S)-pyrrolidin-2-yl)-1H-imidazol-4-yl)biphenyl-4-yl)-1,2,4-oxadiazole (Compound 24a, 0.20 g, 0.48 mmol) was added in one portion. The mixture was stirred overnight at room temperature and 10% citric acid (aq.) was added. The mixture was stirred for 10 minutes. Saturated sodium bicarbonate (aq.) was used to adjust the pH value to about 8. The resulting mixture was extracted with ethyl acetate, dried over magnesium sulfate, filtered and concentrated to yield a crude yellow liquid, which was purified with column chromatography (ethyl acetate: n-hexane=2:1) to yield product 25a as a white solid (0.37 g).

Example 22

Preparation of N4R)-2-((S)-2-(4-(4'-(5-((S)-1-((R)-2-(cyclopropanecarboxamido)-2-phenylacetyl)pyrrolidin-2-yl)-1,2,4-oxadiazol-3-yl)biphenyl-4-yl)-1H-imidazol-2-yl)pyrrolidin-1-yl)-2-oxo-1-phenylethyl) cyclopropanecarboxamide (26a)

Compound 26a was prepared from Compound 25a in a manner similar to that described in Example 7.

Example 23

Preparation of (S)-tert-butyl 2-(4-(4'-(5-((S)-1-(tert-butoxycarbonyl)pyrrolidin-2-yl)-1,2,4-oxadiazol-3-yl)biphenyl-4-yl)thiazol-2-yl)pyrrolidine-1-carboxylate (27a)

Compound 27a was prepared in the same manner as described in Example 4 except that Compounds 13a and 16a, instead of Compounds 2a and 3a, were used.

Example 24

Preparation of 5-((S)-pyrrolidin-2-yl)-3-(4'-(2-((S)-pyrrolidin-2-yl)thiazol-4-yl)biphenyl-4-yl)-1,2,4-oxadiazole (28a)

Compound 28a was prepared from Compound 27a in a manner similar to that described in Example 5. The product was used as the starting material for the next step without further purification.

Example 25

Preparation of Compound 29a

Compound 29a was prepared from Compound 28a in a manner similar to that described in Example 21.

Example 26

Preparation of N4R)-2-((S)-2-(4-(4'-(5-((S)-1-((R)-2-(cyclopropanecarboxamido)-2-phenylacetyl)pyrrolidin-2-yl)-1,2,4-oxadiazol-3-yl)biphenyl-4-yl)thiazol-2-yl)pyrrolidin-1-yl)-2-oxo-1-phenylethyl)cyclopropanecarboxamide (30a)

To a solution of Compound 29a (0.20 g, 0.22 mmol) in DCM (10 ml) at room temperature was added trifluoroacetic acid (5 ml). The reaction mixture was stirred for 2 hours. Saturated sodium bicarbonate (aq.) was added to adjust the pH value to about 8. The resulting mixture was extracted with DCM, dried over $MgSO_4$, filtered and concentrated. The crude product was used as the starting material for the next step without further purification.

To a solution of the white solid in DCM (5 ml) at −10° C. were added cyclopropanecarbonyl chloride (0.058 g, 0.55 mmol) and triethylamine (0.08 ml) in one portion. The reaction mixture was stirred for 15 minutes at −10° C. At room temperature, distilled water was added and then extracted with DCM. The organic layer was dried over $MgSO_4$, filtered, and concentrated to give a crude product, which was purified by chromatograph (ethyl acetate: h-hexane=2:1) to yield product 30a as a white solid (0.07 g).

Example 27

Preparation of (S)-tert-butyl 2-(5-(4'-(5-((S)-1-(tert-butoxycarbonyl)pyrrolidin-2-yl)-1,2,4-oxadiazol-3-yl)biphenyl-4-yl)thiazol-2-yl)pyrrolidine-1-carboxylate (31a)

Compound 31a was prepared in the same manner as described in Example 4 except that Compounds 16a and 22a, instead of Compounds 2a and 3a, were used.

Example 28

Preparation of 5-((S)-pyrrolidin-2-yl)-3-(4'-(2-((S)-pyrrolidin-2-yl)thiazol-5-yl)biphenyl-4-yl)-1,2,4-oxadiazole (32a)

Compound 32a was prepared from Compound 31a in a manner similar to that described in Example 5. The product was used as the starting material for the next step without further purification.

Example 29

Preparation of Compound 33a

Compound 33a was prepared from Compound 32a in a manner similar to that described in Example 21.

Example 30

Preparation of N—((R)-2-(S)-2-(5-(4'-(5-((S)-1-((R)-2-(cyclopropanecarboxamido)-2-phenylacetyl)pyrrolidin-2-yl)-1,2,4-oxadiazol-3-yl)biphenyl-4-yl)thiazol-2-yl)pyrrolidin-1-yl)-2-oxo-1-phenylethyl)cyclopropanecarboxamide (34a)

Compound 34a was prepared from Compound 33a in a manner similar to that described in Example 26.

Example 31

Preparation of (S)-tert-butyl 2-(4-(4'-(2-((S)-1-(tert-butoxycarbonyl)pyrrolidin-2-yl)-1H-imidazol-5-yl)biphenyl-4-yl)thiazol-2-yl)pyrrolidine-1-carboxylate (35a)

A flask charged with Compound 12a (0.46 g, 1.13 mmol), (S)-tert-butyl 2-(5-(4,4,5,5-tetramethyl-1,3,2-dioxaborolan-2-yl)phenyl)-1H-imidazol-2-yl)pyrrolidine-1-carboxylate (compound 20a, 0.55 g, 1.25 mmol), $PdCl_2$(dppf) (0.036 g, 0.04 mmol), and sodium bicarbonate (0.33 g, 3.93 mmol) was flushed with nitrogen, then 1,2-dimethoxyethane (6 ml) and distilled water (2 ml) were added as solvent. The reaction mixture was stirred at 80° C. under nitrogen for 5 hours. After cooled to room temperature, the mixture was extracted with ethyl acetate/water, dried over magnesium sulfate, filtered, and then concentrated to give crude compound. The crude compound was purified by column chromatography (ethyl acetate: n-hexane=4:1) to yield a yellow solid (0.47 g).

Example 32

Preparation of 2-((S)-pyrrolidin-2-yl)-4-(4'-(2-((S)-pyrrolidin-2-yl)-1H-imidazol-5-yl)biphenyl-4-yl)thiazole (36a)

Compound 36a was prepared from Compound 35a in a manner similar to that described in Example 5. The product was used as the starting material for the next step without further purification.

Example 33

Preparation of Compound 37a

To a solution of N-Boc-D-phenylglycine (0.37 g, 0.15 mmol) in N,N-dimethylformamide (8 ml) was added HOBt.H₂O (0.25 g, 1.63 mmol) in one portion at room temperature. After the reaction mixture was stirred 15 minutes, EDC (0.31 g, 1.63 mmol) and 2-((S)-pyrrolidin-2-yl)-4-((S)-pyrrolidin-2-yl)-1H-imidazol-5-yl)biphenyl-4-yl)thiazole (Compound 36a, 0.30 g, 0.68 mmol) were added in one portion. After stirred overnight, the resulting mixture was extracted with ethyl acetate, dried over magnesium sulfate, filtered and concentrated to yield crude product. The crude product was purified by column chromatography (ethyl acetate: n-hexane=2:1) to give product 37a as a white solid (0.42 g).

Example 34

Preparation of N—((R)-2-(S)-2-(4-(4'-(2-((5)-1-((R)-2-(cyclopropanecarboxamido)-2-phenylacetyl)pyrrolidin-2-yl)-1H-imidazol-5-yl)biphenyl-4-yl)thiazol-2-yl)pyrrolidin-1-yl)-2-oxo-1-phenylethyl) cyclopropanecarboxamide (38a)

Compound 38a was prepared from Compound 37a in a manner similar to that described in Example 26.

Example 35

Preparation of (S)-tert-butyl 2-(5-(4'-(2-((5)-1-(tert-butoxycarbonyl)pyrrolidin-2-yl)-1H-imidazol-4-yl)biphenyl-4-yl)thiazol-2-yl)pyrrolidine-1-carboxylate (39a)

Compound 39a was prepared in the same manner as described in Example 4 except that Compounds 20a and 21a, instead of Compounds 2a and 3a, were used.

Example 36

Preparation of 2-((S)-pyrrolidin-2-yl)-5-(4'-(2-((S)-pyrrolidin-2-yl)-1H-imidazol-4-yl)biphenyl-4-yl) thiazole (40a)

Compound 40a was prepared from Compound 39a in a manner similar to that described in Example 5. The product was used as the starting material for the next step without further purification.

Example 37

Preparation of Compound 41a

To a solution of N-Boc-D-phenylglycine (0.14 g, 0.56 mmol) in DMF (5 ml) was added HOBt.H₂O (0.086 g, 0.56 mmol) in one portion at room temperature. After the mixture was stirred for 10 minutes, EDC (0.11 g, 0.56 mmol) was added. The resulting mixture was continually stirred for 30 minutes. 2-((5)-pyrrolidin-2-yl)-5-(4'-(2-((S)-pyrrolidin-2-yl)-1H-imidazol-4-yl)biphenyl-4-yl) thiazole (Compound 40a, 0.10 g, 0.23 mmol) was added in one portion and the reaction mixture was stirred overnight at room temperature. After HOBt salt by washing with distilled water, the resulting mixture was extracted with ethyl acetate. The organic layer was dried over magnesium sulfate, filtered, and concentrated to yield a crude product, which was purified by column chromatography (ethyl acetate: n-hexane=1:1) to give Compound 41a as a white solid (0.072 g).

Example 38

Preparation of N—((R)-2-((S)-2-(5-(4'-(2-((S)-1-((R)-2-(cyclopropanecarboxamido)-2-phenylacetyl) pyrrolidin-2-yl)-1H-imidazol-4-yl)biphenyl-4-yl) thiazol-2-yl)pyrrolidin-1-yl)-2-oxo-1-phenyl-ethyl) cyclopropanecarboxamide (42a)

To a solution of Compound 41a (0.072 g, 0.08 mmol) in DMF (2 ml) was added trifluoroacetic acid (1 ml) at room temperature. The reaction mixture was stirred for 2 hours. At room temperature, saturated sodium bicarbonate (aq.) was added to adjust the pH value to about 8. The resulting mixture was extracted with dichloromethane, dried over magnesium sulfate, filtered and concentrated. The product was used as the starting material for the next step without further purification.

To a solution of the former white solid in THF (20 ml) at −40° C. were added cyclopropanecarbonyl chloride (0.030 g, 0.2 mmol) and triethylamine (0.02 ml) in one portion. The reaction mixture was stirred for 2 hours at −40° C. After the solvent was removed, the crude product was purified by column chromatography (methanol:ethyl acetate=1:40) to yield Compound 42a as a white solid (0.033 g).

Example 39

Preparation of (S)-tert-butyl 2-(5-(4'-(2-((5)-1-(tert-butoxycarbonyl)pyrrolidin-2-yl)thiazol-4-yl) biphenyl-4-yl)thiazol-2-yl)pyrrolidine-1-carboxylate (43a)

Compound 43a was prepared in the same manner as described in Example 4 except that Compounds 13a and 21a, instead of Compounds 2a and 3a, were used.

Example 40

Preparation of (5)-4,5'-(biphenyl-4,4'-diyl)bis(2-((S)-pyrrolidin-2-yl)thiazole) (44a)

Compound 44a was prepared from Compound 43a in a manner similar to that described in Example 5. The product was used as the starting material for the next step without further purification.

Example 41

Preparation of Compound 45a

Compound 45a was prepared from Compound 44a in a manner similar to that described in Example 21.

Example 42

Preparation of N—((R)-2-(S)-2-(5-(4'-(2-((S)-1-((R)-2-(cyclopropanecarboxamido)-2-phenylacetyl)pyrrolidin-2-yl)thiazol-4-yl)biphenyl-4-yl)thiazol-2-yl) pyrrolidin-1-yl)-2-oxo-1-phenylethyl) cyclopropanecarboxamide (46a)

Compound 46a was prepared from Compound 45a in a manner similar to that described in Example 26.

Example 43

Compound 47

A solution of bromine (1.3 mL, 25.0 mmol) in glacial acetic acid (15 mL) was added drop-wise to a solution of 4,4'-diacetylbiphenyl (3.0 g, 12.5 mmol) in acetic acid (40 mL) at 50° C. After the addition, the reaction mixture was stirred at room temperature overnight. The precipitate was filtered and re-crystallized from chloroform to give 1,1'-(biphenyl-4,4'-diyl)bis(2-bromoethanone) 47 (3.84 g, 77.5%) as a white solid. LC/MS (ESI): [M+1]$^+$: 397.

Example 44

Compound 48

Sodium diformylamide (3.66 g, 38.5 mmol) was added to a suspension of 1,1'-(biphenyl-4,4'-diyl)bis(2-bromoethanone) 47 (6.1 g, 15.4 mmol) in acetonitrile (85 mL). The reaction mixture was refluxed for 4 hours and then concentrated under reduced pressure. The residue was suspended in 5% HCl in ethanol (300 mL) and refluxed for 4 hours. The reaction mixture was cooled to room temperature and placed in a freezer for 1 hour. The precipitate was collected, washed with ether (200 mL×3), and dried under vacuum to afford 1,1'-(biphenyl-4,4'-diyl)bis(2-aminoethanone) dihydrochloride 48 (4.85 g, 92%). The product was carried on without further purification. LC/MS (ESI): [M+1]$^+$: 269.

Example 45

Compound 49a

To a stirred solution of 1,1'-(biphenyl-4,4'-diyl)bis(2-aminoethanone) dihydrochloride 48 (0.7 g, 2.1 mmol), N-Boc-L-proline (0.9 g, 4.2 mmol), and HATU (1.68 g, 4.4 mmol) in DMF (15 mL) was added diisopropylethyl amine (1.5 mL, 8.4 mmol) drop-wise over 5 minutes. The resulting mixture was stirred at room temperature overnight and concentrated under reduced pressure. The residue was extracted with 20% methanol/chloroform and water. The aqueous phase was washed once with 20% methanol/chloroform. The combined organic layers were washed with brine, dried over MgSO$_4$, filtered, and concentrated under reduced pressure. The crude product was purified through column chromatography on silica gel by gradient elution with 10-50% ethyl acetate/DCM to give product 49a (0.97 g, 69%). LC/MS (ESI): [M+1]$^+$: 663.

Example 46

Compounds 50a and 51a

To a solution of Compound 6a (462 mg, 0.5 mmol) in DCM (5 mL) at room temperature was added trifluoroacetic acid (1 mL). Then, the reaction was stirred at room temperature for 2 hours. After reaction was complete, it was cooled with an ice bath and saturated sodium bicarbonate solution was added until pH=7-8. The resulting mixture was extracted with DCM (10 mL×8). The organic layer was dried over MgSO$_4$, filtered, and concentrated to afford a crude product, which was used as the starting material for the next step without further purification. A solution of the crude product in THF (5 mL) was cooled with an ice bath. Acetyl chloride (94 mg, 1.2 mmol) and triethylamine (121 mg, 1.2 mmol) were added sequentially. After the ice bath was removed, the reaction mixture was stirred at room temperature for 10 min and then concentrated under reduced pressure. The residue was extracted with ethyl acetate (10 mL×4). The combined organic layers were washed with brine, dried over MgSO$_4$, filtered, and concentrated. The residue was purified by column chromatography over silica gel (1% methanol in DCM) to afford final products 50a (160 mg, 40%) and Ma (50 mg, 12%). LC/MS (ESI): [M+2]$^+$/2: 405, [M+1]$^+$: 809, [M+23]$^+$: 831.

Example 47

Compounds 52a and 53a

Compounds 52a and 53a were prepared in the same manner as described in Example 46 except that propionyl chloride, instead of acetyl chloride, was used. LC/MS (ESI): [M+2]$^+$/2: 419, [M+1]$^+$: 837, [M+23]$^+$: 859.

Example 48

Compounds 54a and 55a

Compounds 54a and 55a were prepared in the same manner as described in Example 46 except that butyryl chloride, instead of acetyl chloride, was used. LC/MS (ESI): [M+2]$^+$/2: 433, [M+1]$^+$: 865, [M+23]$^+$: 887.

Example 49

Compounds 56a and 57a

Compounds 56a and 57a were prepared in the same manner as described in Example 46 except that pentanoyl chloride, instead of acetyl chloride, was used. LC/MS (ESI): [M+2]$^+$/2: 447, [M+1]$^+$: 893, [M+23]$^+$: 915.

Example 50

Compounds 58a and 59a

Compounds 58a and 59a were prepared in the same manner as described in Example 46 except that hexanonyl chloride, instead of acetyl chloride, was used. LC/MS (ESI): [M+2]$^+$/2: 461, [M+1]$^+$: 921, [M+23]$^+$: 943.

Example 51

Compounds 60a and 61a

Compounds 60a and 61a were prepared in the same manner as described in Example 46 except that isobutyryl chloride, instead of acetyl chloride, was used. LC/MS (ESI): [M+2]$^+$/2: 433, [M+1]$^+$: 865, [M+23]$^+$: 887.

Example 52

Compounds 62a and 63a

Compounds 62a and 63a were prepared in the same manner as described in Example 46 except that 2-ethyl-butyryl chloride, instead of acetyl chloride, was used. LC/MS (ESI): [M+2]$^+$/2:461, [M+1]$^+$: 921, [M+23]$^+$: 943.

Example 53

Compounds 64a and 65a

Compounds 64a and 65a were prepared in the same manner as described in Example 46 except that 2,2-dimethyl propionyl chloride, instead of acetyl chloride, was used. LC/MS (ESI): $[M+2]^+/2$: 447, $[M+1]^+$: 893, $[M+23]^+$: 915.

Example 54

Compounds 66a and 67a

Compounds 66a and 67a were prepared in the same manner as described in Example 46 except that cyclobutane carbonyl chloride, instead of acetyl chloride, was used. LC/MS (ESI): $[M+2]$445, $[M+1]^+$: 889, $[M+23]^+$: 911.

Example 55

Compounds 68a and 69a

Compounds 68a and 69a were prepared in the same manner as described in Example 46 except that cyclopentane carbonyl chloride, instead of acetyl chloride, was used. LC/MS (ESI): $[M+2]^+/2$: 459, $[M+1]^+$: 917, $[M+23]^+$: 939.

Example 56

Compounds 70a and 71a

Compounds 70a and 71a were prepared in the same manner as described in Example 46 except that cyclohexane carbonyl chloride, instead of acetyl chloride, was used. LC/MS (ESI): $[M+2]^+/2$: 473, $[M+1]^+$: 945, $[M+23]^+$: 967.

Example 57

Compounds 72a and 73a

Compounds 72a and 73a were prepared in the same manner as described in Example 46 except that benzoyl chloride, instead of acetyl chloride, was used. LC/MS (ESI): $[M+2]^+/2$: 467, $[M+1]^+$: 933, $[M+23]^+$: 955.

Example 58

Compounds 74a and 75a

Compounds 74a and 75a were prepared in the same manner as described in Example 46 except that phenylacetyl chloride, instead of acetyl chloride, was used. LC/MS (ESI): $[M+2]^+/2$: 481, $[M+1]^+$: 961, $[M+23]^+$: 983.

Example 59

Compounds 76a and 77a

Compounds 76a and 77a were prepared in the same manner as described in Example 46 except that furan-2-carbonyl chloride, instead of acetyl chloride, was used. LC/MS (ESI): $[M+2]^+/2$: 457, $[M+1]^+$: 913, $[M+23]^+$: 935.

Example 60

Compounds 78a and 79a

Compounds 78a and 79a were prepared in the same manner as described in Example 46 except that furan-3-carbonyl chloride, instead of acetyl chloride, was used. LC/MS (ESI): $[M+2]^+/2$: 457, $[M+1]^+$: 913, $[M+23]^+$: 935.

Example 61

Compounds 80a and 81a

Compounds 80a and 81a were prepared in the same manner as described in Example 46 except that thiophene-2-carbonyl chloride, instead of acetyl chloride, was used. LC/MS (ESI): $[M+2]^+/2$: 473, $[M+1]^+$: 945, $[M+23]^+$: 967.

Example 62

Compounds 82a and 83a

Compounds 82a and 83a were prepared in the same manner as described in Example 46 except that thiophene-3-carbonyl chloride, instead of acetyl chloride, was used. LC/MS (ESI): $[M+2]^+/2$: 473, $[M+1]^+$: 945, $[M+23]^+$: 967.

Example 63

Compounds 84a and 85a

Compounds 84a and 85a were prepared in the same manner as described in Example 46 except that isonicotinoyl chloride, instead of acetyl chloride, was used. LC/MS (ESI): $[M+2]^+/2$: 468, $[M+1]^+$: 935, $[M+23]^+$: 957.

Example 64

Compounds 86a and 87a

Compounds 86a and 87a were prepared in the same manner as described in Example 46 except that nicotinoyl chloride, instead of acetyl chloride, was used. LC/MS (ESI): $[M+2]^+/2$: 468, $[M+1]^+$: 935, $[M+23]^+$: 957.

Example 65

Compounds 87a and 88a

Compounds 87a and 88a were prepared in the same manner as described in Example 46 except that pyridine-2-carbonyl chloride, instead of acetyl chloride, was used. LC/MS (ESI): $[M+2]^+/2$: 468, $[M+1]^+$: 935, $[M+23]^+$: 957.

Example 66

Compounds 90a and 91a

Compounds 90a and 91a were prepared in the same manner as described in Example 46 except that pyrrolidine-1-carbonyl chloride, instead of acetyl chloride, was used. LC/MS (ESI): $[M+2]^+/2$: 460, $[M+1]^+$: 919, $[M+23]^+$: 941.

Example 67

Compound 92a

Compound 92a was prepared in the same manner as described in Example 46 except that piperidine-1-carbonyl chloride, instead of acetyl chloride, was used. LC/MS (ESI): $[M+2]$474, $[M+1]^+$: 947, $[M+23]^+$: 969.

Example 68

Compound 95a

To a solution of N-methoxycarbonyl-D-valine (420 mg, 2.4 mmol) in DCM (10 mL) was added HOBt.H$_2$O (367 mg, 2.4 mmol) in one portion and stirred at room temperature for 10 min. To the reaction mixture, EDC (460 mg, 2.4 mmol) was added and continually stirred for 30 min. A solution of compound 5a (458 mg, 1.0 mmol) in DCM (5 mL) was added and then stirred overnight at room temperature. After HOBt salt was removed by washing with water, the organic layer was dried over MgSO$_4$, filtered and concentrated to give viscous yellow liquid. The liquid was purified by column chromatography over silica gel (methanol:DCM=1:20) to yield white solid 95a (425 mg, 55%). LC/MS (ESI): [M+2]$^+$/2: 387, [M+1]$^+$: 773, [M+23]$^+$: 795.

Example 69

Compound 96a

Compound 96a was prepared in the same manner as described in Example 68 except that N-ethoxycarbonyl-D-valine, instead of N-methoxycarbonyl-D-valine, was used. LC/MS (ESI): [M+2]$^+$/2: 401, [M+1]$^+$: 801, [M+23]$^+$: 823.

Example 70

Compound 97a

Compound 97a was prepared in the same manner as described in Example 68 except that N-phenoxycarbonyl-D-valine, instead of N-methoxycarbonyl-D-valine, was used. LC/MS (ESI): [M+2]$^+$/2: 449, [M+1]$^+$: 897, [M+23]$^+$: 919.

Example 71

Compound 98a

Compound 98a was prepared in the same manner as described in Example 68 except that N-cyclopropanecarbonyl-D-alanine, instead of N-methoxycarbonyl-D-valine, was used. LC/MS (ESI): [M+2]$^+$/2: 369, [M+1]$^+$: 737, [M+23]$^+$: 759.

Example 72

Compound 99a

Compound 99a was prepared in the same manner as described in Example 68 except that (R)-2-(cyclopropanecarbonyl-amino)-butyric acid, instead of N-methoxycarbonyl-D-valine, was used. LC/MS (ESI): [M+2]$^+$/2: 383, [M+1]$^+$: 765, [M+23]$^+$: 787.

Example 73

Compound 100a

Compound 100a was prepared in the same manner as described in Example 68 except that (R)-2-(cyclopropanecarbonyl-amino)-pentanoic acid, instead of N-methoxycarbonyl-D-valine, was used. LC/MS (ESI): [M+2]$^+$/2: 397, [M+1]$^+$: 793, [M+23]$^+$: 815.

Example 74

Compound 101a

Compound 101a was prepared in the same manner as described in Example 68 except that (R)-2-(cyclopropanecarbonyl-amino)-hexanoic acid, instead of N-methoxycarbonyl-D-valine, was used. LC/MS (ESI): [M+2]$^+$/2: 411, [M+1]$^+$: 821, [M+23]$^+$: 843.

Example 75

Compound 102a

Compound 102a was prepared in the same manner as described in Example 68 except that N-cyclopropanecarbonyl-D-valine, instead of N-methoxycarbonyl-D-valine, was used. LC/MS (ESI): [M+2]$^+$/2: 397, [M+1]$^+$: 793, [M+23]$^+$: 815.

Example 76

Compound 103a

Compound 103a was prepared in the same manner as described in Example 68 except that N-cyclopropanecarbonyl-D-leucine, instead of N-methoxycarbonyl-D-valine, was used. LC/MS (ESI): [M+2]$^+$/2: 411, [M+1]$^+$: 821, [M+23]$^+$: 843.

Example 77

Compound 104a

Compound 104a was prepared in the same manner as described in Example 68 except that (R)-2-(cyclopropanecarbonyl-amino)-3,3-dimethyl-butyric acid, instead of N-methoxycarbonyl-D-valine, was used. LC/MS (ESI): [M+2]$^+$/2: 411, [M+1]$^+$: 821, [M+23]$^+$: 843.

Example 78

Compound 105a

Compound 105a was prepared in the same manner as described in Example 68 except that (R)-cyclohexyl-(cyclopropanecarbonyl-amino)-acetic acid, instead of N-methoxycarbonyl-D-valine, was used. LC/MS (ESI): [M+2]$^+$/2: 437, [M+1]$^+$: 873, [M+23]$^+$: 895.

Example 79

Compound 106a

Compound 106a was prepared in the same manner as described in Example 68 except that N-methoxycarbonyl-L-alanine, instead of N-methoxycarbonyl-D-valine, was used. LC/MS (ESI): [M+2]$^+$/2: 359, [M+1]$^+$: 717, [M+23]$^+$: 739.

Example 80

Compound 107a

Compound 107a was prepared in the same manner as described in Example 68 except that (S)-2-methoxycarbonylamino-butyric acid, instead of N-methoxycarbonyl-D-valine, was used. LC/MS (ESI): [M+2]$^+$/2: 373, [M+1]$^+$: 745, [M+23]$^+$: 767.

Example 81

Compound 108a

Compound 108a was prepared in the same manner as described in Example 68 except that (S)-2-methoxycarbony-

97 lamino-pentanoic acid, instead of N-methoxycarbonyl-D-valine, was used. LC/MS (ESI): [M+2]$^+$/2: 387, [M+1]$^+$: 773, [M+23]$^+$: 795.

Example 82

Compound 109a

Compound 109a was prepared in the same manner as described in Example 68 except that (S)-2-methoxycarbonylamino-hexanoic acid, instead of N-methoxycarbonyl-D-valine, was used. LC/MS (ESI): [M+2]$^+$/2: 401, [M+1]: 801, [M+23]$^+$: 823.

Example 83

Compound 110a

Compound 110a was prepared in the same manner as described in Example 68 except that N-methoxycarbonyl-L-leucine, instead of N-methoxycarbonyl-D-valine, was used. LC/MS (ESI): [M+2]$^+$/2: 401, [M+1]$^+$: 801, [M+23]$^+$: 823.

Example 84

Compound 111a

Compound 111a was prepared in the same manner as described in Example 68 except that (S)-2-methoxycarbonylamino-3,3-dimethyl-butyric acid, instead of N-methoxycarbonyl-D-valine, was used. LC/MS (ESI): [M+2]$^+$/2: 401, [M+1]$^+$: 801, [M+23]$^+$: 823.

Example 85

Compound 112a

Compound 112a was prepared in the same manner as described in Example 68 except that N-methoxycarbonyl-L-valine, instead of N-methoxycarbonyl-D-valine, was used. LC/MS (ESI): [M+2]$^+$/2: 387, [M+1]$^+$: 773, [M+23]$^+$: 795.

Example 86

Compound 113a

Compound 113a was prepared in the same manner as described in Example 68 except that N-ethoxycarbonyl-L-valine, instead of N-methoxycarbonyl-D-valine, was used. LC/MS (ESI): [M+2]$^+$/2: 401, [M+1]$^+$: 801, [M+23]$^+$: 823.

Example 87

Compound 114a

Compound 114a was prepared in the same manner as described in Example 68 except that N-phenoxycarbonyl-L-valine, instead of N-methoxycarbonyl-D-valine, was used. LC/MS (ESI): [M+2]$^+$/2: 449, [M+1]$^+$: 897, [M+23]$^+$: 919.

Example 88

Compound 115a

Compound 115a was prepared in the same manner as described in Example 1 except that N-Boc-D-Proline, instead of N-Boc-L-Proline, was used. LC/MS (ESI): [M+1]$^+$: 411.

98

Example 89

Compound 116a

Compound 116a was prepared in a manner similar to that described in Example 2. LC/MS (ESI): [M+1]$^+$: 409.

Example 90

Compound 117a

Compound 117a was prepared in a manner as described in Example 3 except that Compound 116a, instead of Compound 2a, was used. LC/MS (ESI): [M+1]$^+$: 456.

Example 91

Compound 118a

Compound 118a was prepared in the same manner as described in Example 4 except that Compounds 116a and 117a, instead of Compounds 2a and 3a, were used. LC/MS (ESI), [M+1]$^+$: 659.

Example 92

Compound 119a

Compound 119a was prepared from Compound 118a in a manner similar to that described in Example 5. LC/MS (ESI): [M+2]$^+$/2: 230, [M+1]$^+$: 459, [M+23]$^+$: 481.

Example 93

Compound 120a

Compound 120a was prepared in the same manner as described in Example 68 except that N-Boc-L-phenylglycine, instead of N-methoxycarbonyl-D-valine, was used. LC/MS (ESI): [M+2]$^+$/2: 463, [M+1]$^+$: 925, [M+23]$^+$: 947.

Example 94

Compound 121a

Compound 121a was prepared in the same manner as described in Example 68 except that N-Boc-D-phenylglycine, instead of N-methoxycarbonyl-D-valine, and 119a, instead of 5a, were used. LC/MS (ESI): [M+2]$^+$/2: 463, [M+1]$^+$: 925, [M+23]$^+$: 947.

Example 95

Compound 122a

Compound 122a was prepared in the same manner as described in Example 68 except that N-Boc-L-phenylglycine, instead of N-methoxycarbonyl-D-valine, and 119a, instead of 5a, were used. LC/MS (ESI): [M+2]$^+$/2: 463, [M+1]$^+$: 925, [M+23]$^+$: 947.

Example 96

Compounds 123a and 124a

Compounds 123a and 124a were prepared in the same manner as described in Example 46 except that cyclopropanecarbonyl chloride, instead of acetyl chloride, and 120a, instead of 6a, were used. LC/MS (ESI): [M+2]$^+$/2: 431, [M+1]$^+$: 861, [M+23]$^+$: 883.

Example 97

Compounds 125a and 127a

Compounds 125a and 127a were prepared in the same manner as described in Example 46 except that cyclopropanecarbonyl chloride, instead of acetyl chloride, and 121a, instead of 6a, were used. LC/MS (ESI): [M+2]$^+$/2: 431, [M+1]$^+$: 861, [M+23]$^+$: 883.

Example 98

Compounds 126a and 127a

Compounds 126a and 127a were prepared in the same manner as described in Example 46 except that cyclopropanecarbonyl chloride, instead of acetyl chloride, and 122a, instead of 6a, were used. LC/MS (ESI): [M+2]$^+$/2: 431, [M+1]$^+$: 861, [M+23]$^+$: 883.

Example 99

Compound 128a

Compound 128a was prepared in the same manner as described in Example 68 except that D-valine, instead of N-methoxycarbonyl-D-valine, was used. LC/MS (ESI): [M+1]$^+$: 657.

Example 100

Compound 129a

Compound 129a was prepared in the same manner as described in Example 68 except that L-valine, instead of N-methoxycarbonyl-D-valine, was used. LC/MS (ESI): [M+1]$^+$: 657.

Example 101

Inhibiting HCV Replication

The inhibitory activity of compounds of this invention against HCV replication was assessed using Ava5-EG (Δ4AB)SEAP, a reporter-based cell line, according to the methods described in Lee et al., Anal. Biochem., 316:162-70 (2003) and Lee et al., J. Virol Methods, 116:27-33 (2004). Briefly, Ava5-EG(Δ4AB)SEAP cells were cultured in a medium containing 500 μg/mL G418 (geneticin) and 10 μg/mL blasticidin in a 5% CO$_2$ incubator. G418 and blasticidin were purchased from Invitrogen (Carlsbad, Calif.). The cells were seeded in a 96-well plate (5×10$^3$ cells/100 μL-well) and incubated at 37° C. for 24 hours. They were then treated with a solution of a test compound in DMSO at various concentrations. After 48 hours, the culture medium in each well was replaced with a fresh medium containing the test compound at the same concentrations to remove secreted alkaline phosphatase (SEAP) accumulated in the culture medium, if any. The cells were cultured for additional 24 hours. The culture medium was then collected and tested for SEAP activity using a Phospha-Light assay kit (Tropix, Foster, Calif., USA).

Compounds 6a, 7a-A, 7b-A, 7c-A, 7a-B, 7b-B, 7c-B, 25a, 26a, 29a, 30a, 33a, 34a, 37a, 38a, 41a, 42a, 45a, 46a, 50a-77a, 80a, 81a, 84a, 85a, 88a-98a, and 100a-129a were tested in this assay. All of the test compounds inhibited HCV replication. Unexpectedly, 6a, 7a-A, 7b-A, 7c-A, 7a-B, 7b-B, 7c-B, 25a, 26a, 29a, 30a, 33a, 34a, 37a, 38a, 41a, 42a, 45a, 46a, 50a, 51a, 52a, 54a, 56a, 58a, 60a, 61a, 66a, 67a, 68a, 70a, 74a, 76a, 84a, 90a, 92a showed EC$_{50}$ values (i.e., the concentration of a test compound at which 50% HCV replication is inhibited) 0.5 μM or lower. More unexpectedly, 50a, 52a, 54a, 56a, 60a, 66a, 68a, 90a, and 92a showed EC$_{50}$ values lower than 0.04 μM.

Example 102

Cytotoxicity Assay

Viability of cells after treatment (see Example 43 above) was determined by the MTS assay described in Cory et al., Cancer Commun. 3:207-12 (1991). Briefly, Ava5-EG(Δ4AB) SEAP cells were treated with a test compound as described above. After 48 hours, each culture medium was replaced with a fresh medium containing the test compound at the same concentration. The cells were cultured for additional 24 hours. To each well was added 100 μl of a solution containing phenol red-free DMEM, [3-(4,5-dimethylthiozol-2-yl)-5-(3-carboxymethoxyphenyl)-2-(4-sulfophenyl)-2H-tetrazolium, inner salt] (Promega, Madison, Wis.), and phenazine methosulfate (Sigma, St. Louis, Mo.) at a ratio of 80:20:1. The cells were incubated at 37° C. for 1-4 hours in a 5% CO$_2$ incubator. The absorbance at 490 nm in each well was measured.

Compounds 6a, 7a-A, 7b-A, 7c-A, 7a-B, 7b-B, 7c-B, 25a, 26a, 29a, 30a, 33a, 34a, 37a, 38a, 41a, 42a, 45a, 46a, 50a-77a, 80a, 81a, 84a, 85a, 88a-98a, and 100a-129a were tested in this assay. Unexpectedly, all of the test compounds showed CC$_{50}$ values (i.e., the concentration of a test compound at which 50% of the cells are killed) greater than 50 μM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

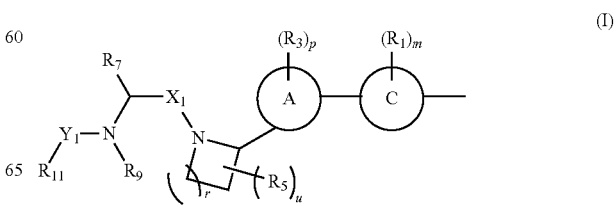

-continued

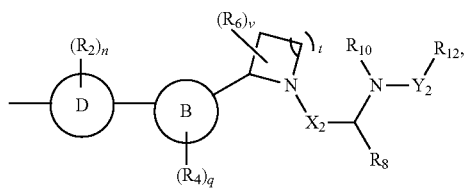

wherein
A is

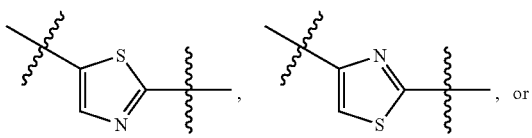

B is

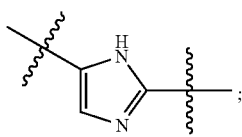

each of C and D, independently, is phenylene;
each of $R_1$, $R_2$, $R_3$, $R_4$, $R_5$, and $R_6$, independently, is alkyl, alkenyl, alkynyl, aryl, heteroaryl, cycloalkyl, cycloalkenyl, heterocycloalkyl, halo, heterocycloalkenyl, cyano, or nitro;
each of $R_7$ and $R_8$, independently, is H, alkyl, alkenyl, alkynyl, aryl, heteroaryl, cycloalkyl, cycloalkenyl, heterocycloalkyl, or heterocycloalkenyl;

each of $R_9$ and $R_{10}$, independently, is H or alkyl;
each of $R_{11}$ and $R_{12}$, independently, is H, alkyl, alkenyl, alkynyl, aryl, heteroaryl, cycloalkyl, cycloalkenyl, heterocycloalkyl, or heterocycloalkenyl;
each of $X_1$ and $X_2$, independently, is C(O) or C(S);
each of $Y_1$ and $Y_2$, independently, is deleted, SO, $SO_2$, C(O), C(O)O, C(O)$NR_a$, C(S)$NR_a$, or $SO_2NR_a$, in which $R_a$ is H, alkyl, cycloalkyl, heterocycloalkyl, aryl, or heteroaryl;
each of m and n, independently, is 0, 1, 2, 3, or 4;
each of p and q, independently, is 0 or 1;
each of r and t, independently, is 1, 2, or 3; and
each of u and v, independently, is 0, 1, 2, 3, 4, 5, 6, 7, or 8.

2. The compound of claim 1, wherein the compound is of formula (II):

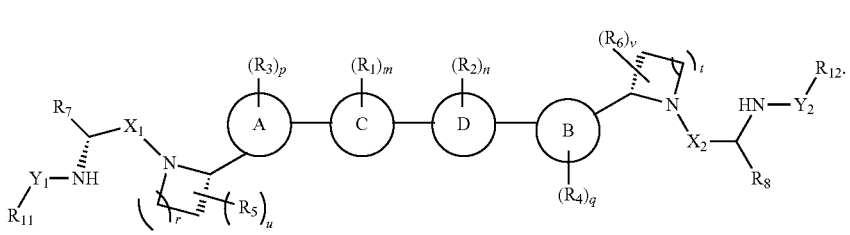

(II)

3. The compound of claim 2, wherein each of A and B is

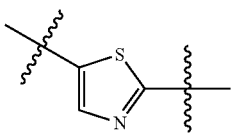 [SMILES: *c1cnc(*)s1]

and each of C and D is phenylene.

4. The compound of claim 3, wherein each of $X_1$ and $X_2$ is C(O) and each of $Y_1$ and $Y_2$, independently, is $SO_2$, C(O), or C(O)O.

5. The compound of claim 4, wherein each of $R_7$ and $R_8$ is phenyl.

6. The compound of claim 5, wherein each of $R_{11}$ and $R_{12}$, independently, is $C_{1-5}$ alkyl or $C_{3-5}$ cycloalkyl.

7. The compound of claim 6, wherein each of t and r is 2.

8. The compound of claim 2, wherein
A is

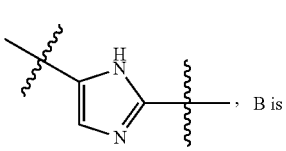, B is 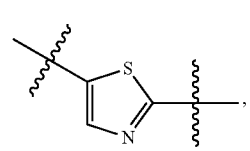, and
each of C and D is phenylene.

9. The compound of claim 1, wherein each of A and B is

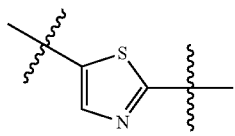

and each of C and D is phenylene.

10. The compound of claim 9, wherein each of $R_7$ and $R_8$ is phenyl.

11. The compound of claim 10, wherein each of $R_{11}$ and $R_{12}$, independently, is $C_{1-5}$ alkyl or $C_{3-5}$ cycloalkyl.

12. The compound of claim 11, wherein the compound is of formula (II):

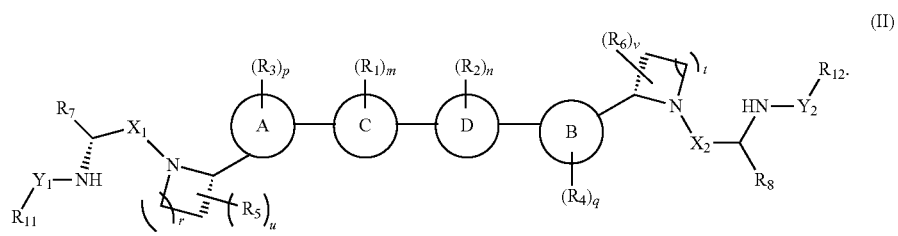

13. The compound of claim 1, wherein each of $R_7$ and $R_8$ is phenyl.

14. The compound of claim 13, wherein each of $R_{11}$ and $R_{12}$, independently, is $C_{1-5}$ alkyl or $C_{3-5}$ cycloalkyl.

15. The compound of claim 14, wherein the compound is of formula (II):

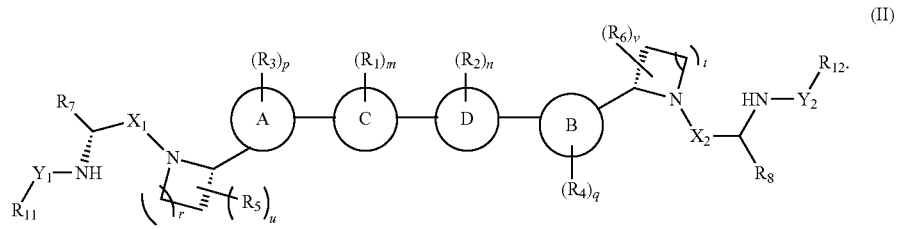

16. The compound of claim 1, wherein each of $R_{11}$ and $R_{12}$, independently, is $C_{1-5}$ alkyl or $C_{3-5}$ cycloalkyl.

17. The compound of claim 1, wherein each of t and r is 2.

18. The compound of claim 1, wherein each of p, m, n, q, u and v is 0.

19. The compound of claim 1, wherein each of p, m, n, and q is 0, each of u and v is 1, and each $R_5$ and $R_6$ is F.

20. The compound of claim 1, wherein the compound is of formula (III):

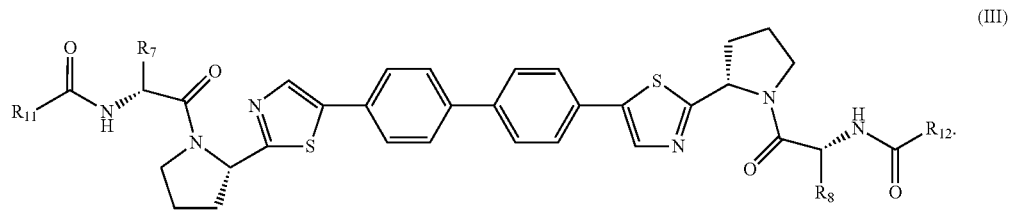

21. The compound of claim 20, wherein each of $R_7$ and $R_8$ is phenyl.

22. The compound of claim 21, wherein each of $R_{11}$ and $R_{12}$, independently, is alkyl, cycloalkyl, or heterocycloalkyl.

23. The compound of claim 22, wherein each of $R_{11}$ and $R_{12}$, independently, is heterocycloalkyl or alkyl substituted with amino or heterocycloalkyl.

24. The compound of claim 1, wherein the compound is one of compounds:

6a

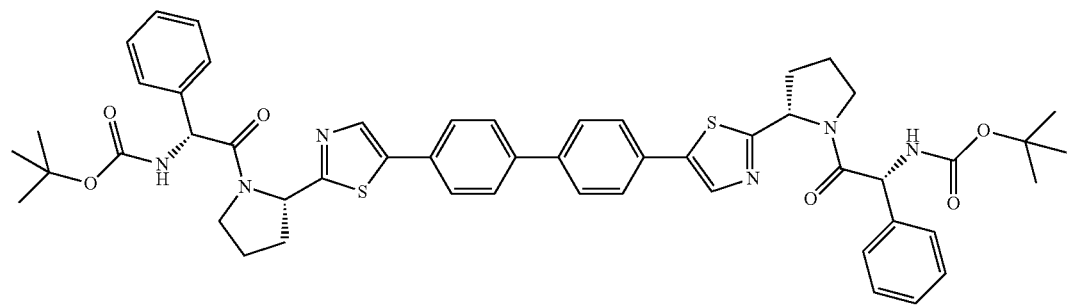

7a-A

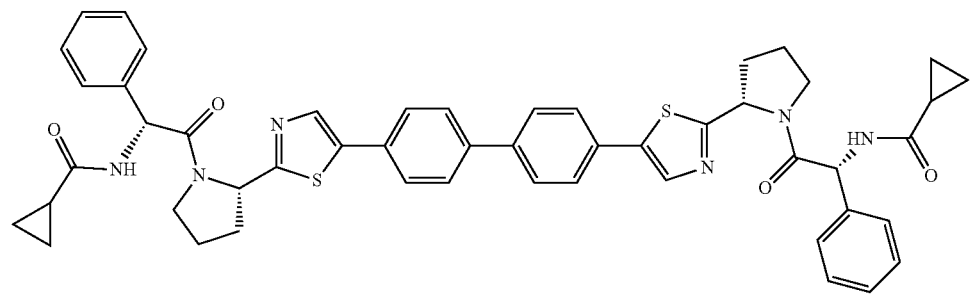

7b-A

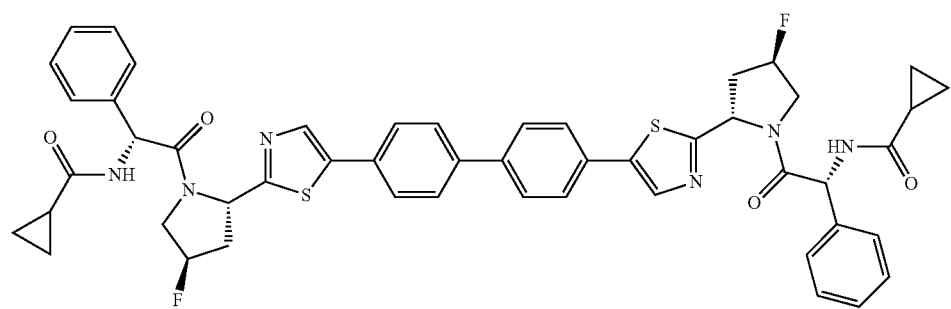

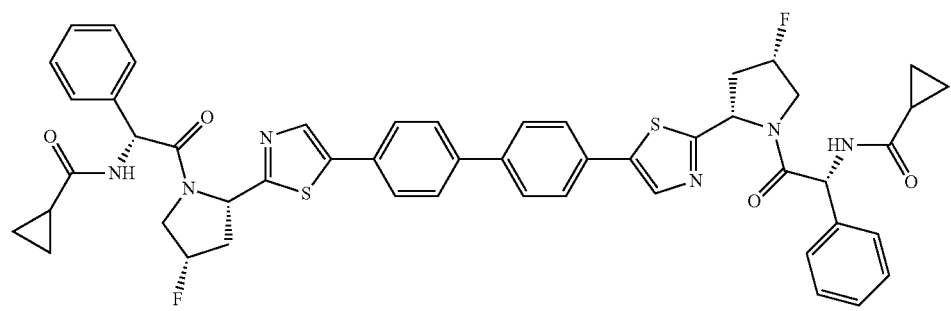

-continued
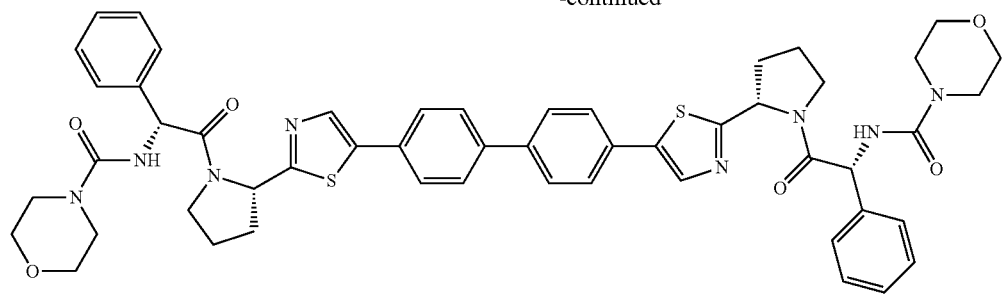
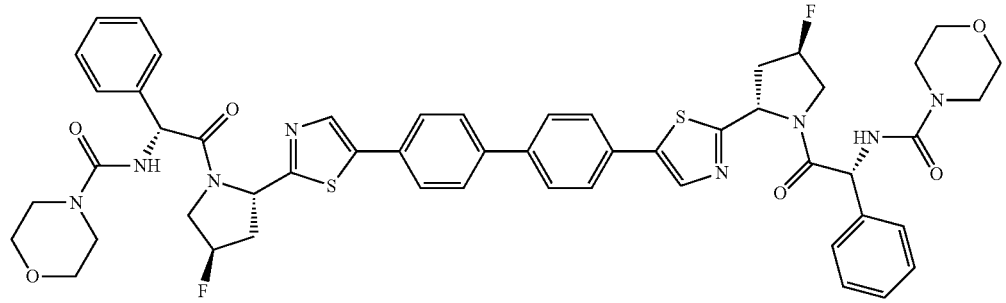
7c-B
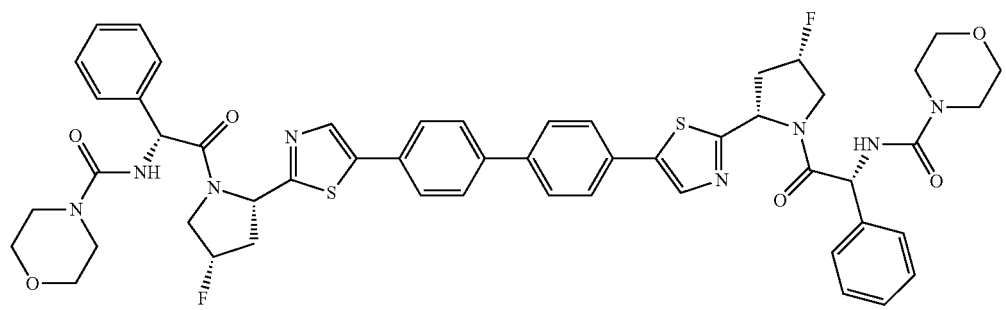
37a
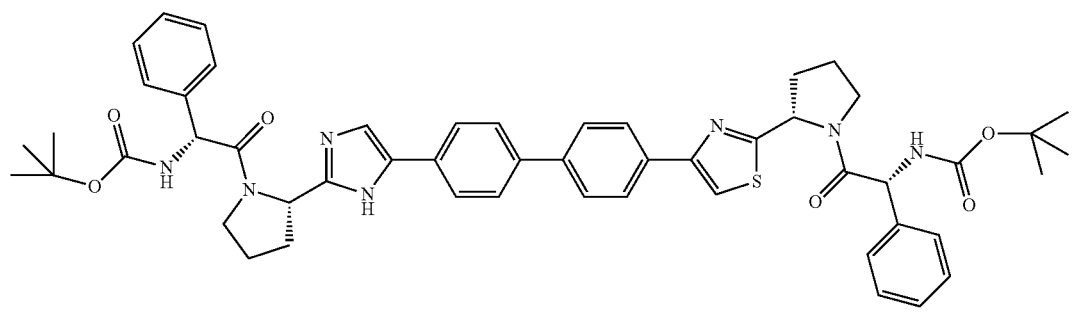
38a
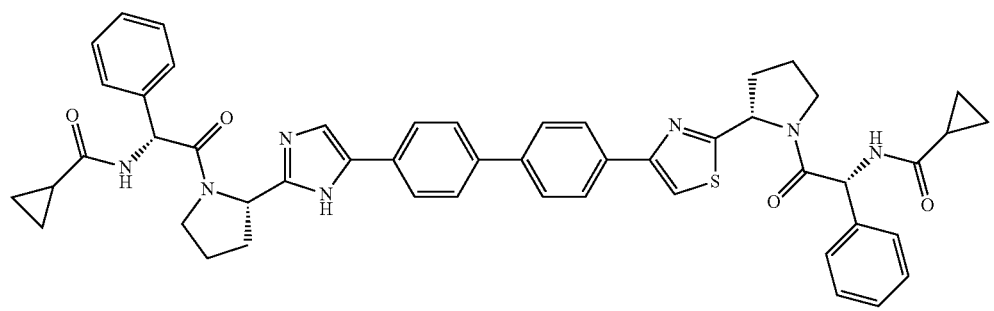

41a
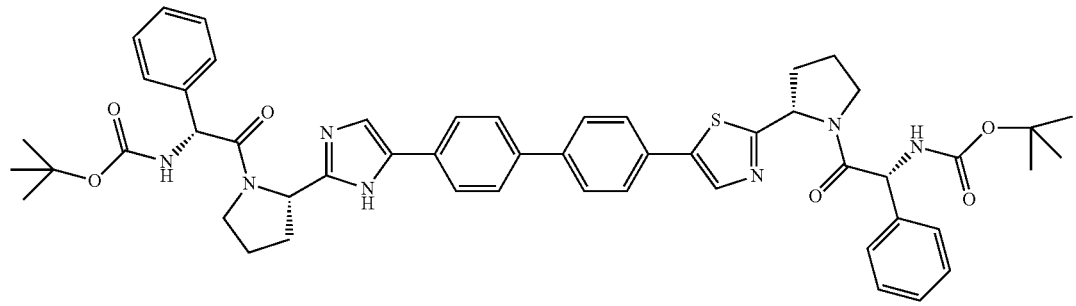
42a
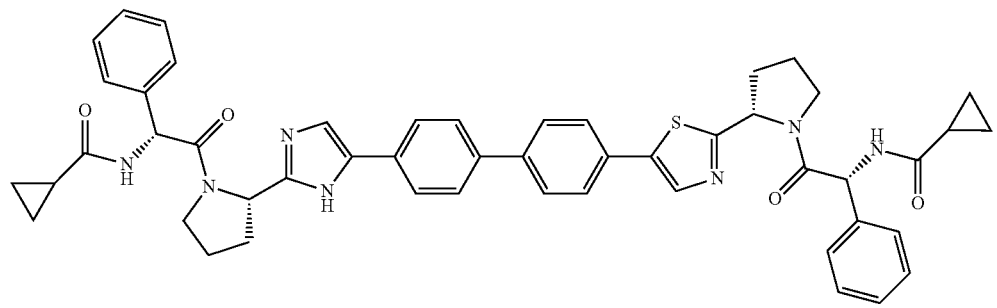
45a
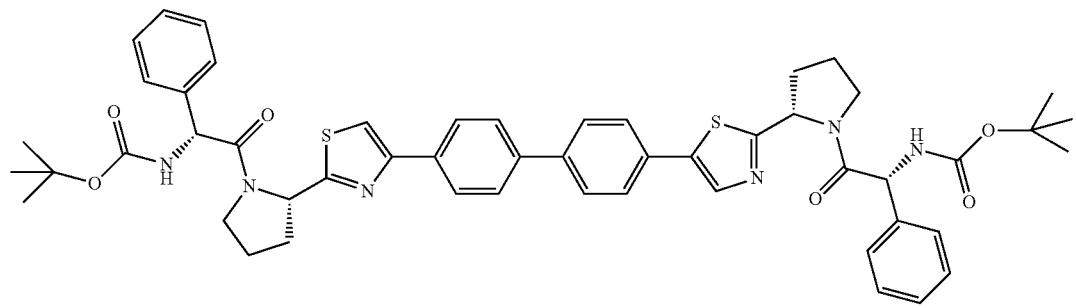
46a
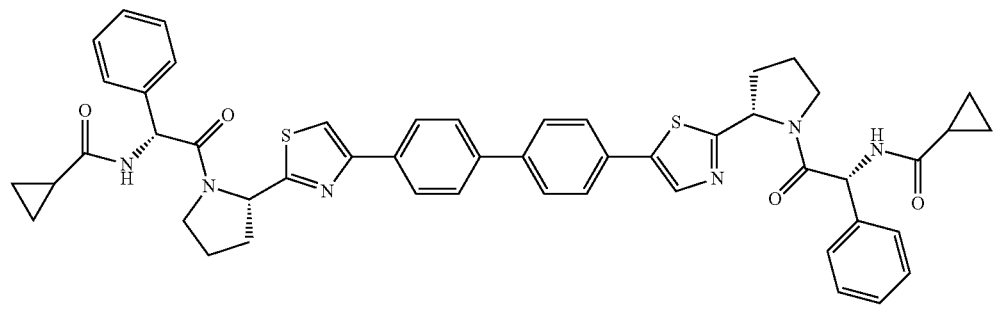
50a
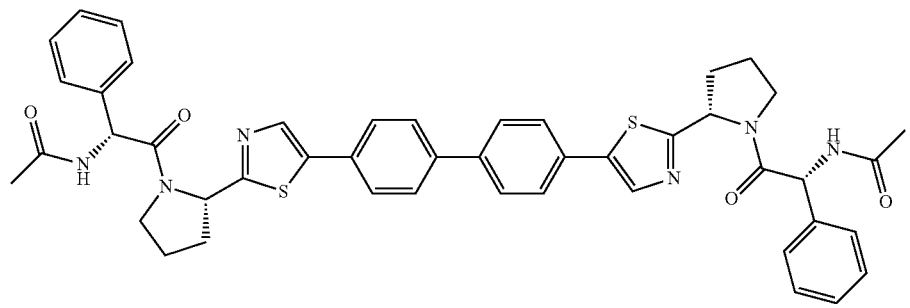

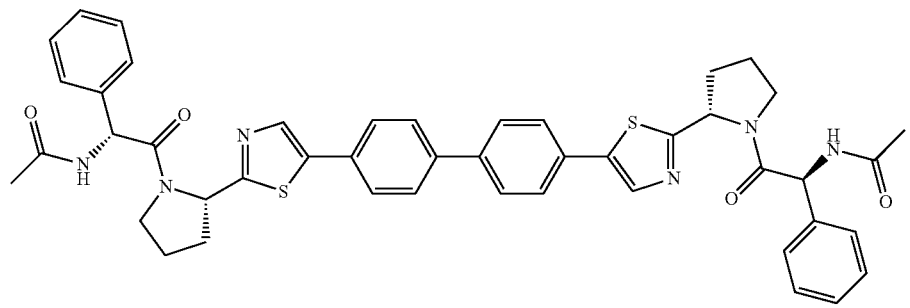
51a
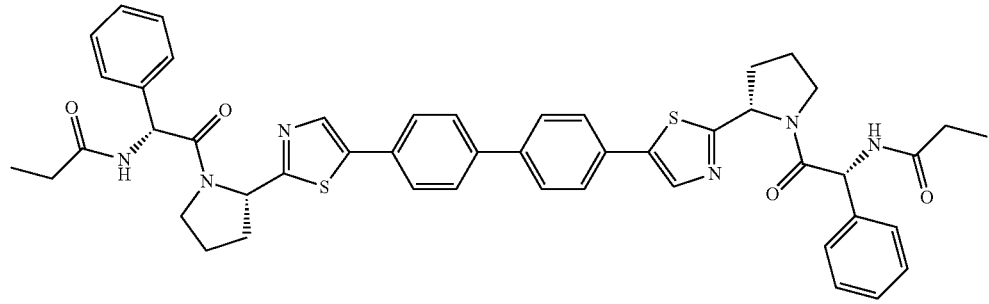
52a
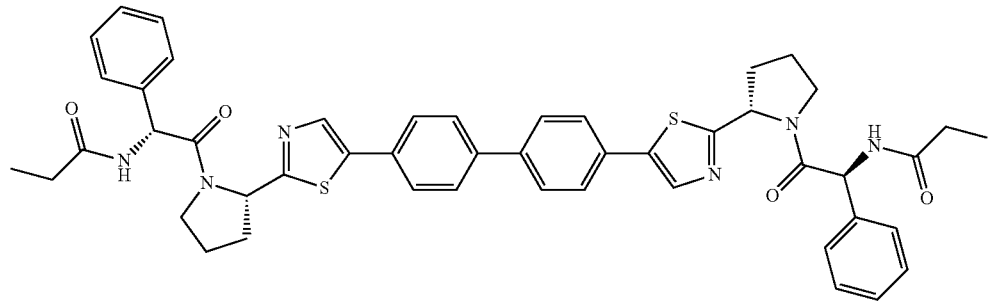
53a
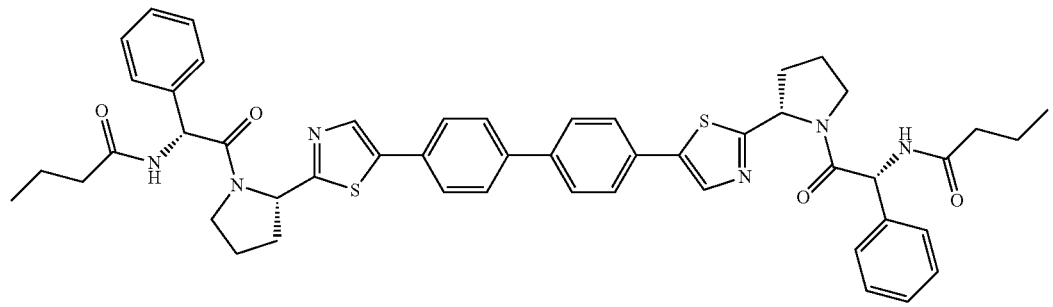
54a
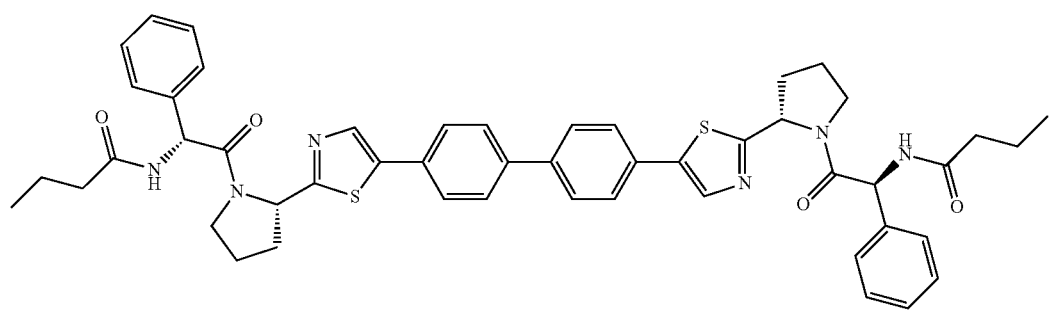
55a

56a
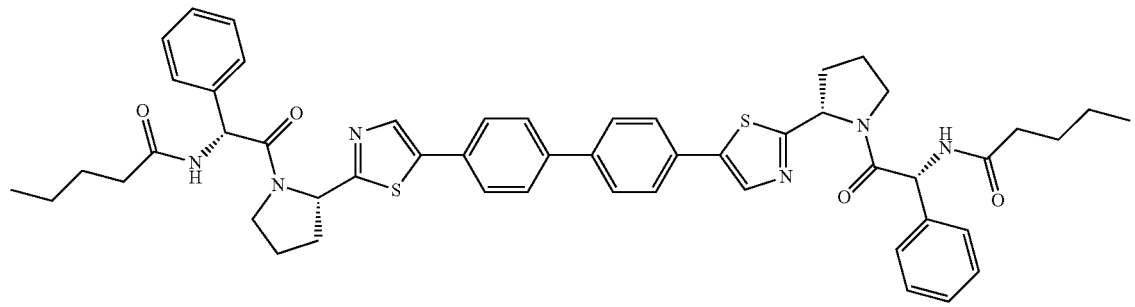
57a
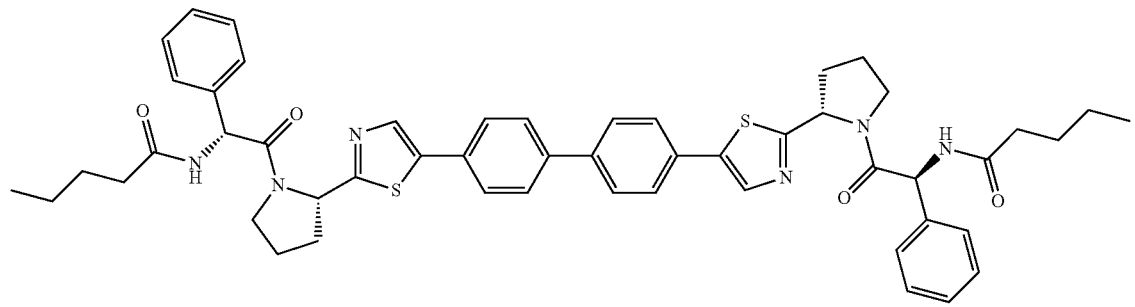
58a
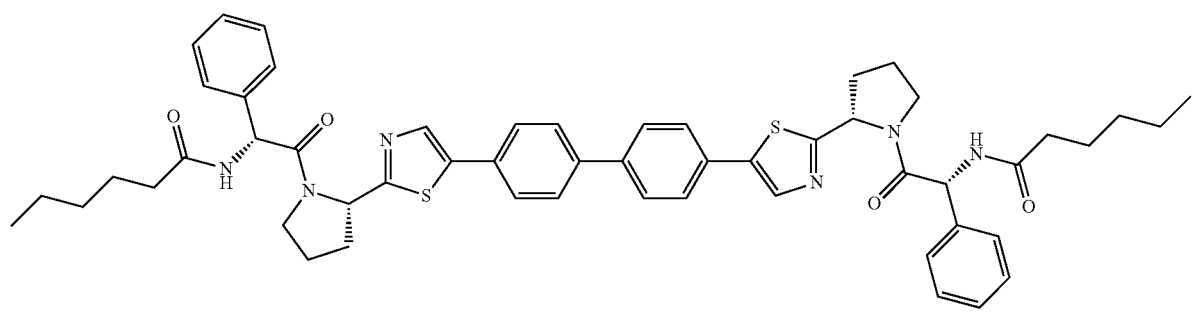
59a
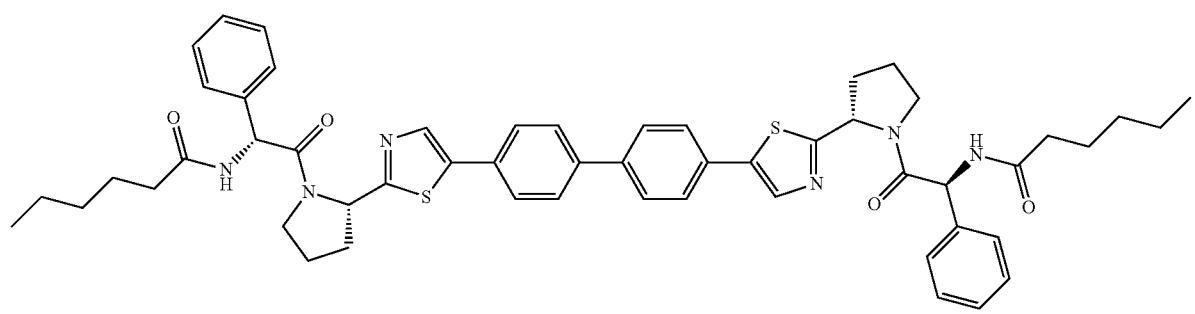
60a
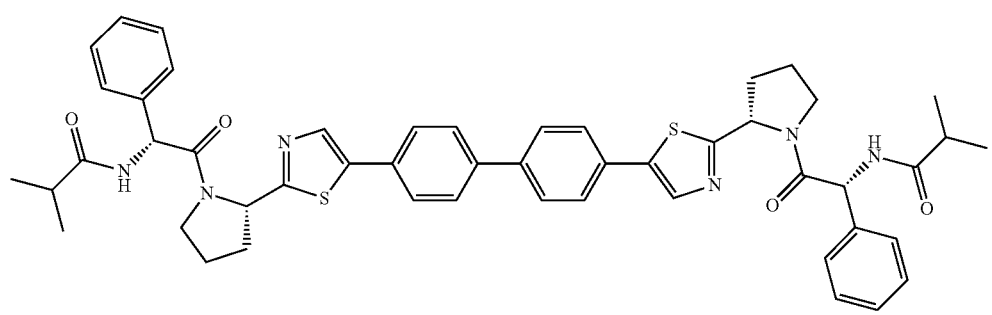

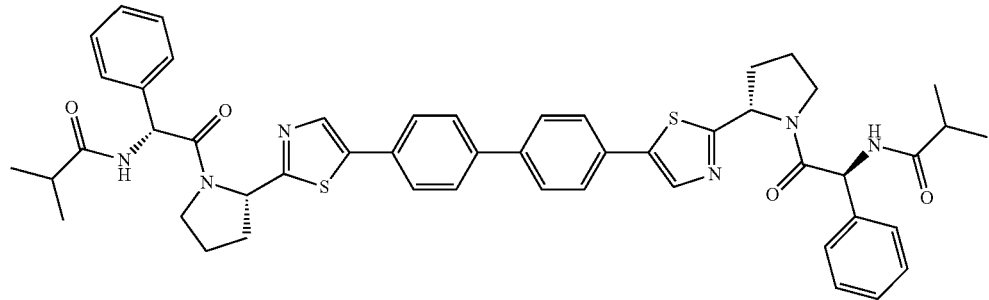
61a
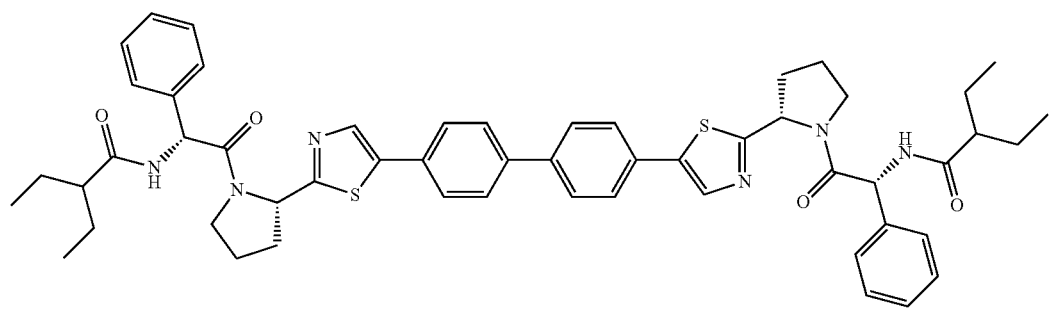
62a
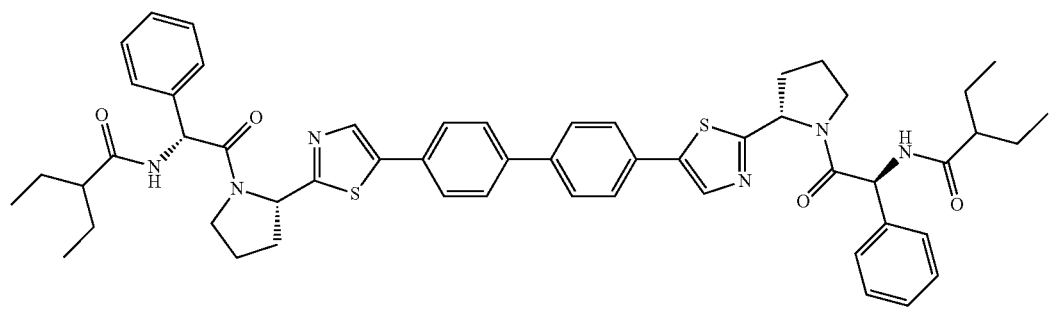
63a
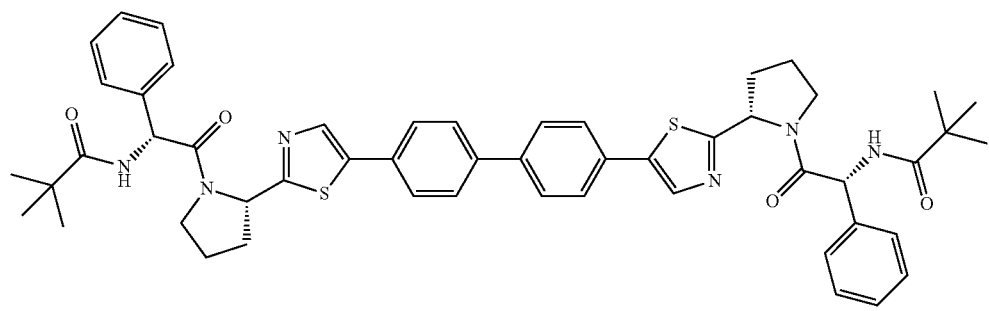
64a
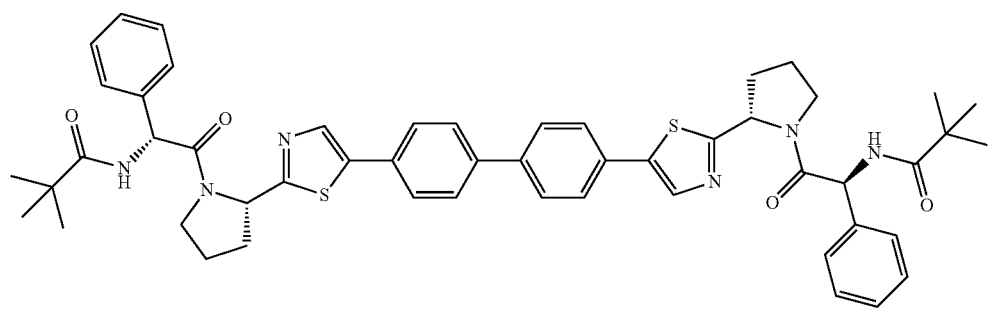
65a

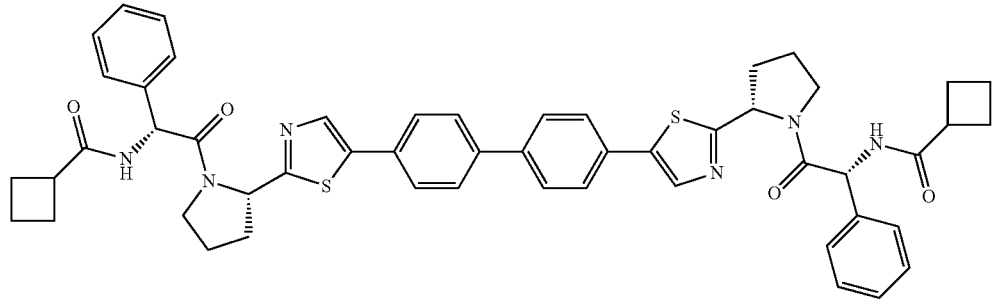
66a
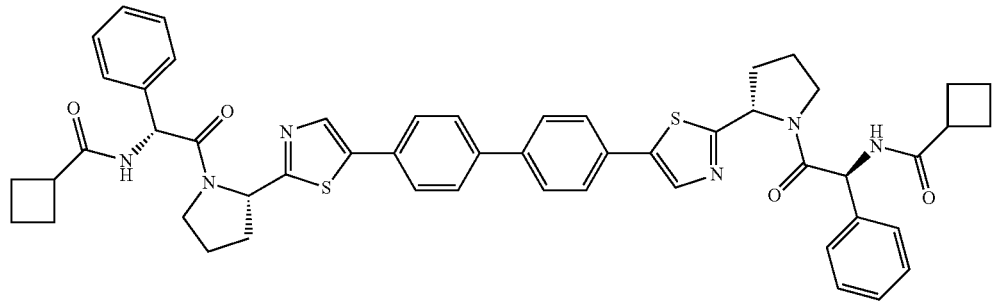
67a
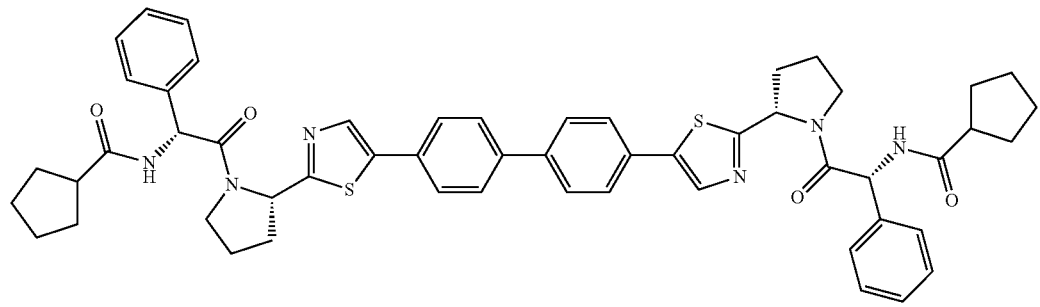
68a
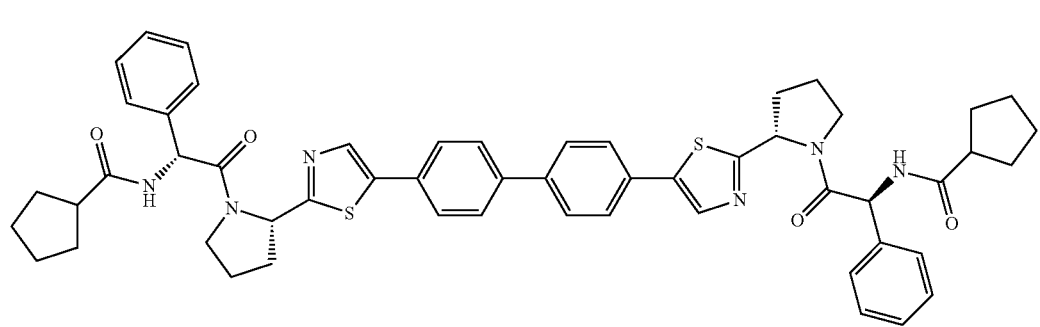
69a
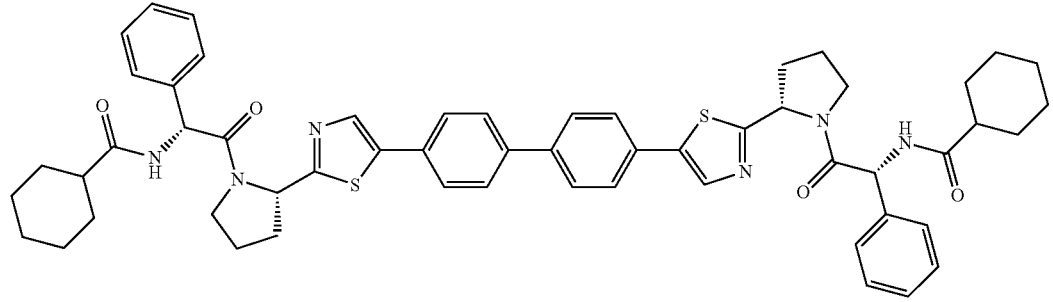
70a

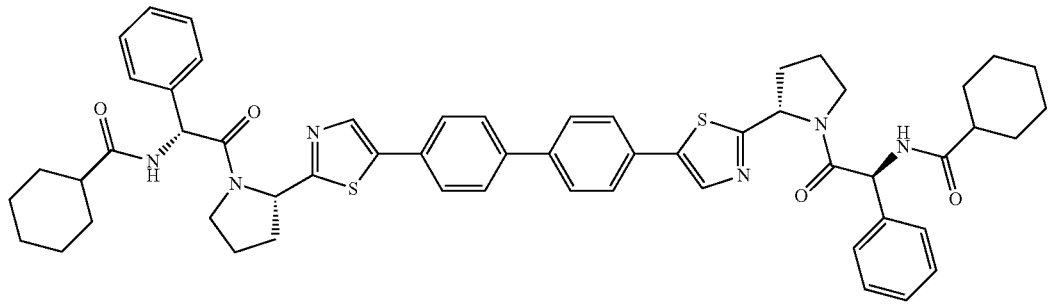
71a
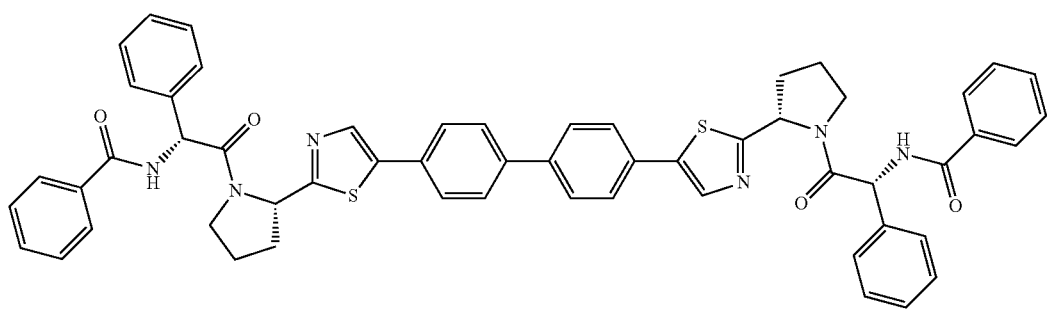
72a
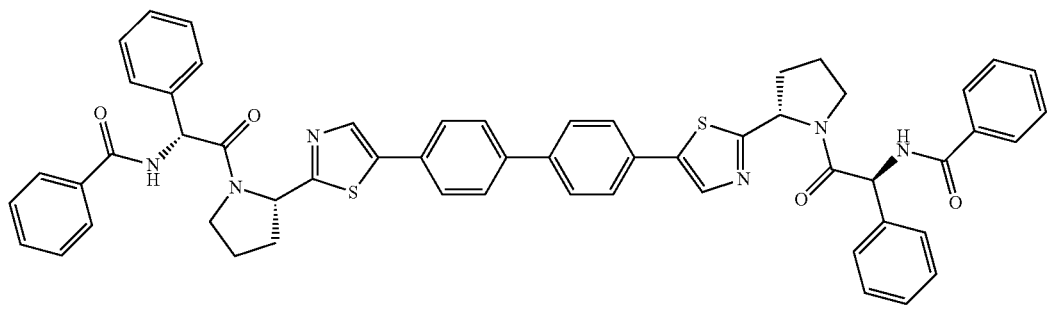
73a
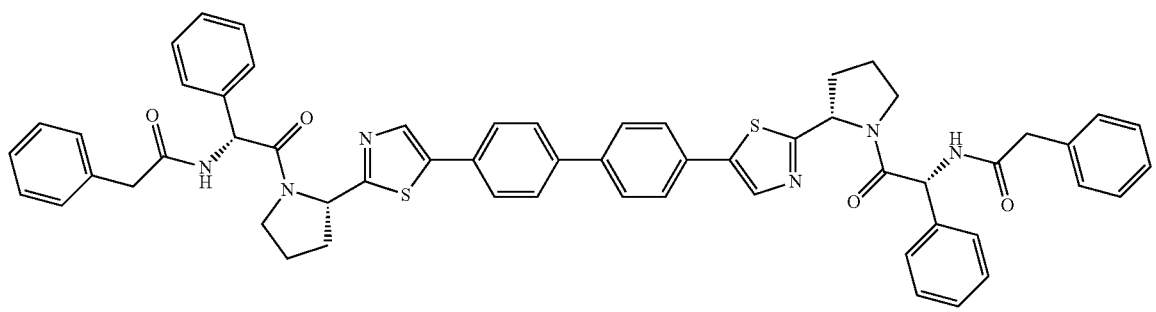
74a
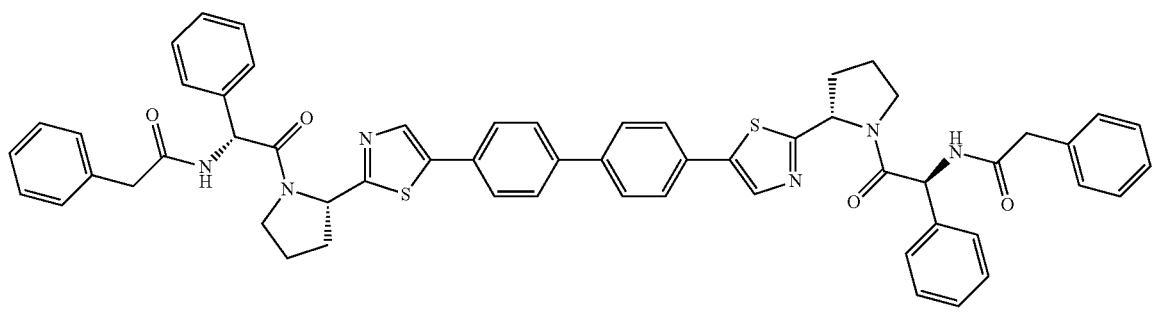
75a

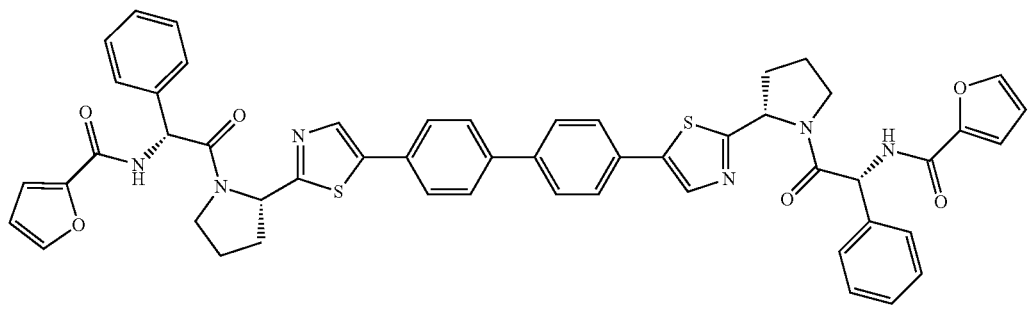
76a
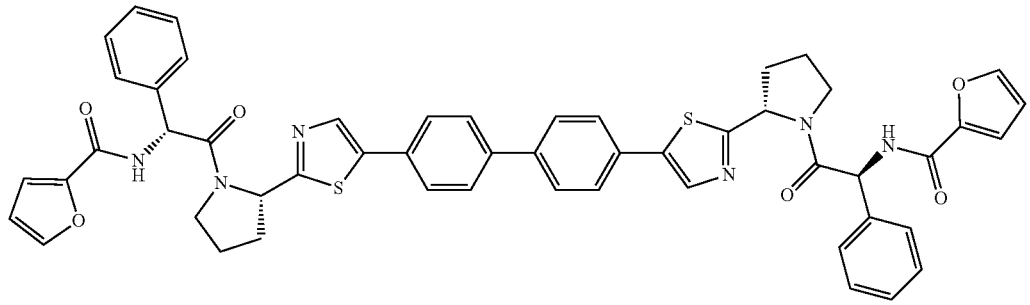
77a
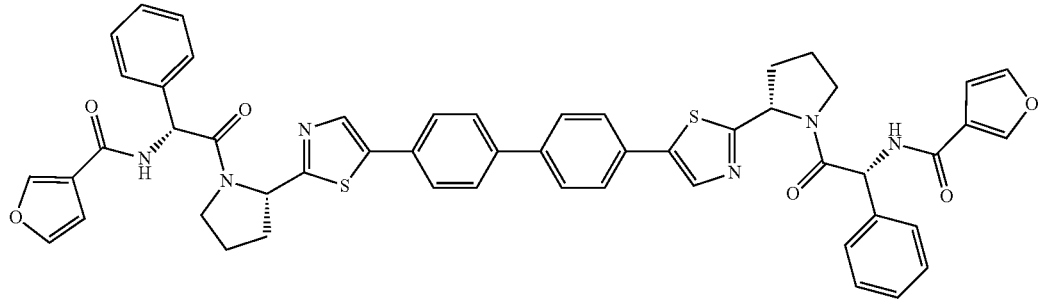
78a
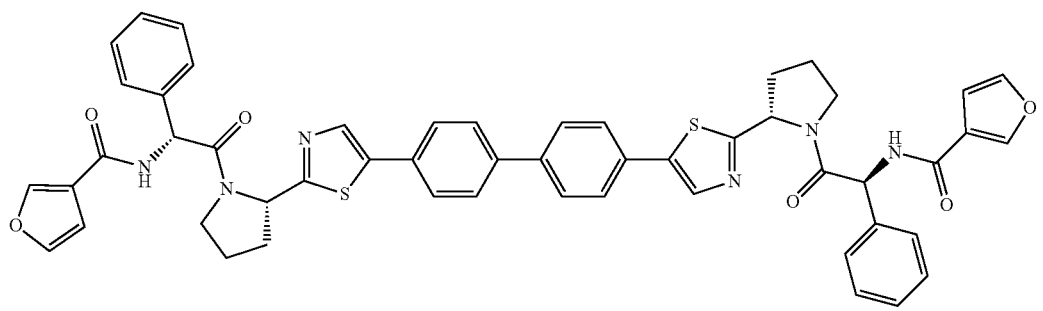
79a
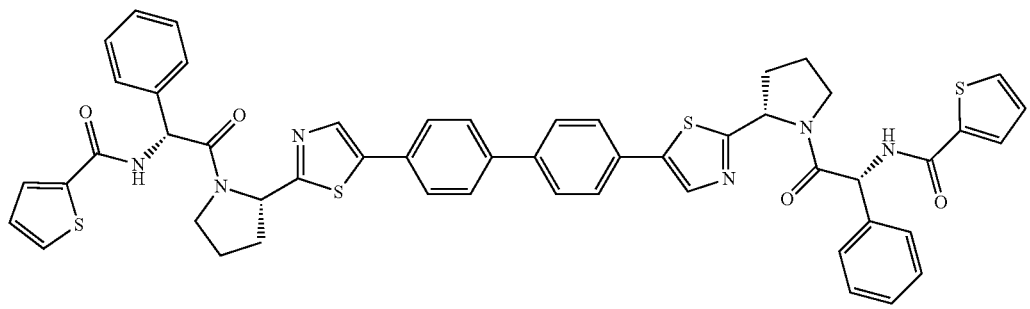
80a

-continued
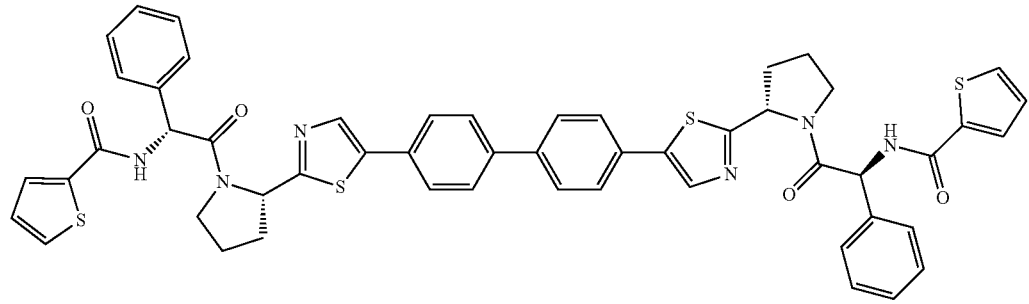
81a
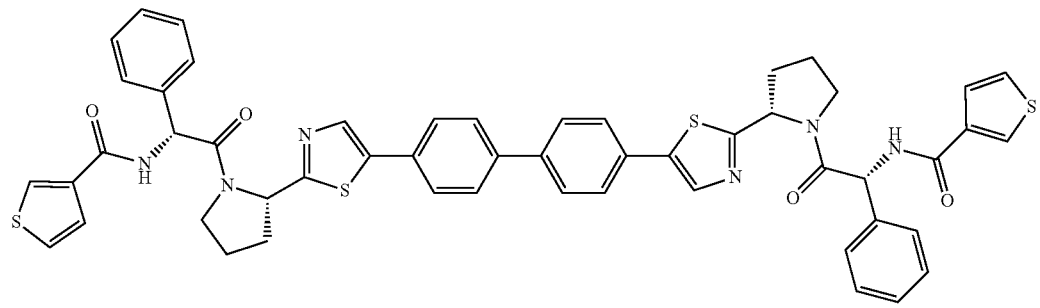
82a
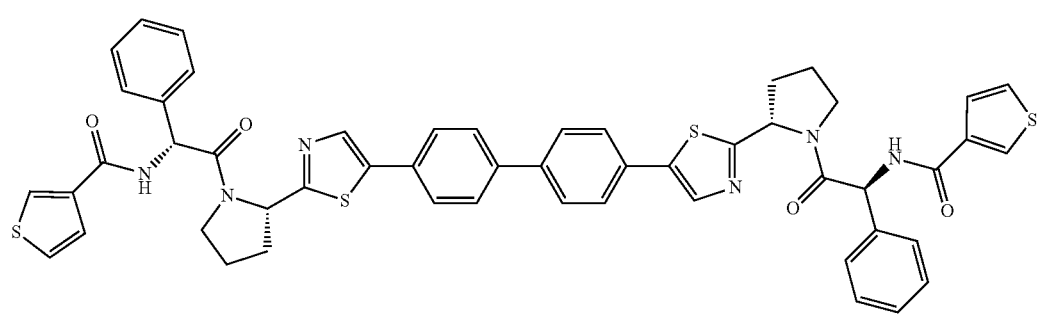
83a
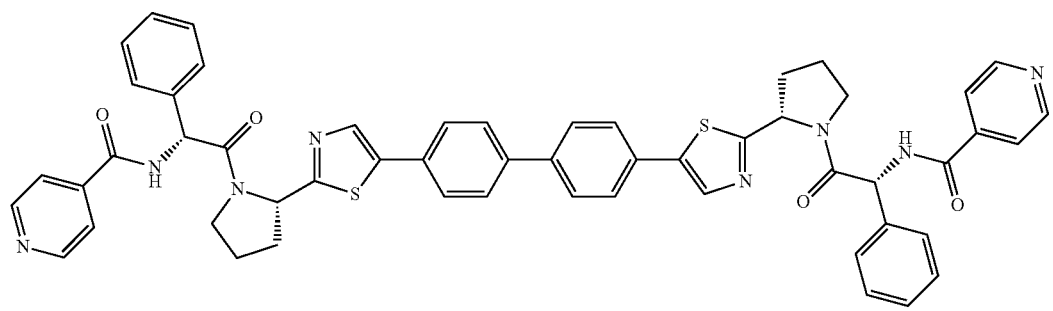
84a
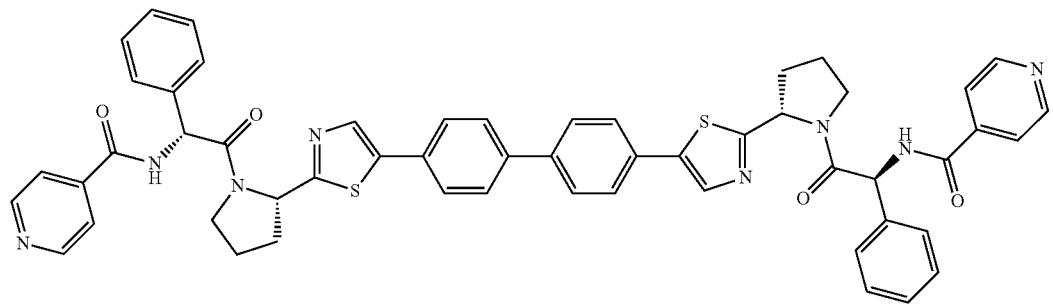
85a -continued
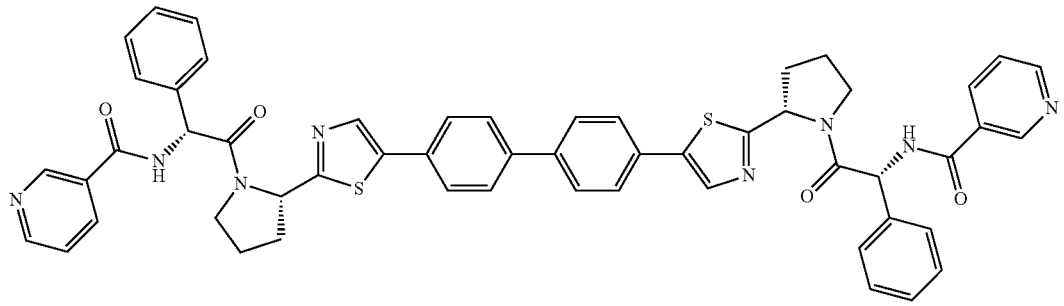
86a
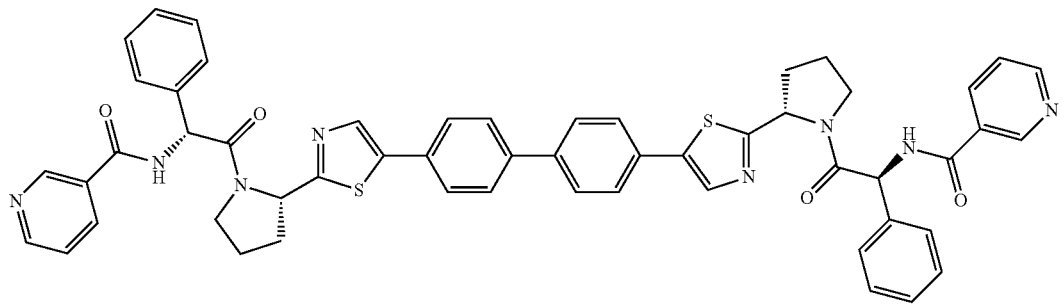
87a
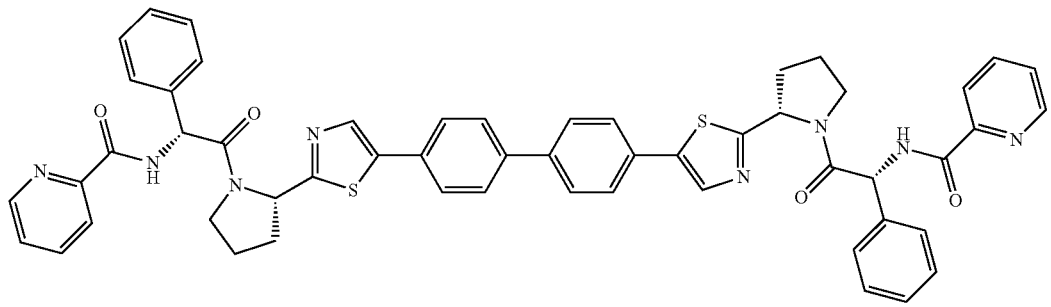
88a
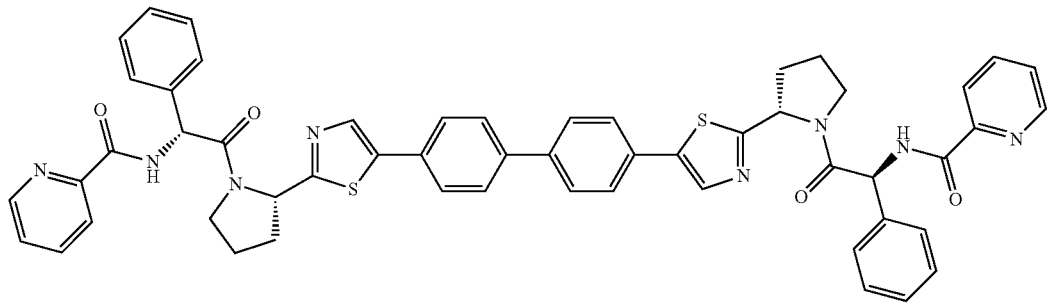
89a
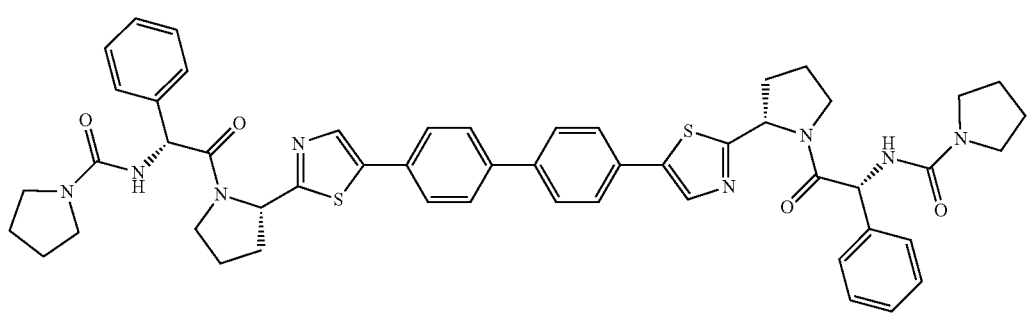
90a -continued
91a
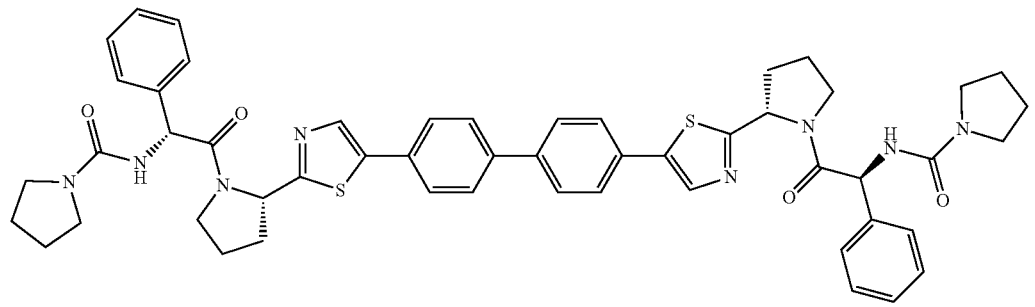
92a
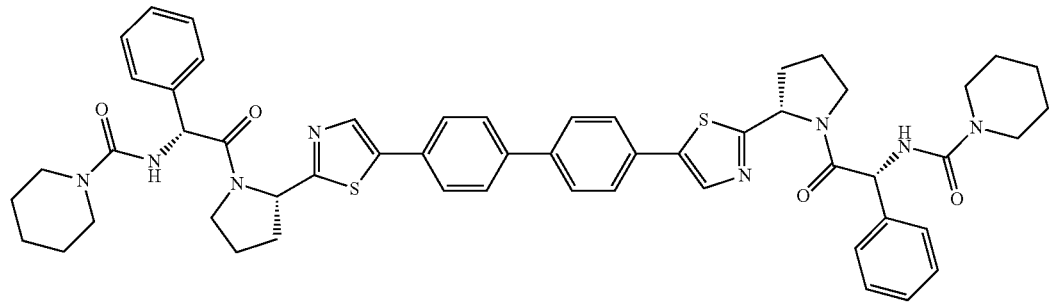
95a
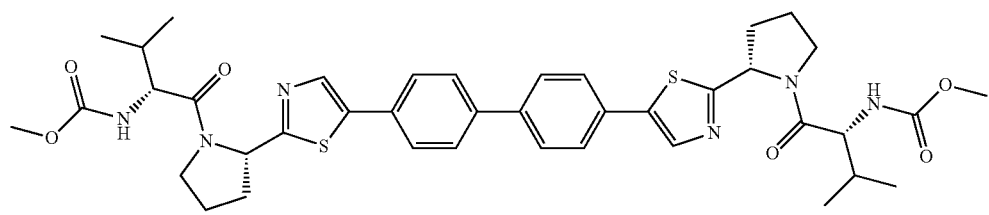
96a
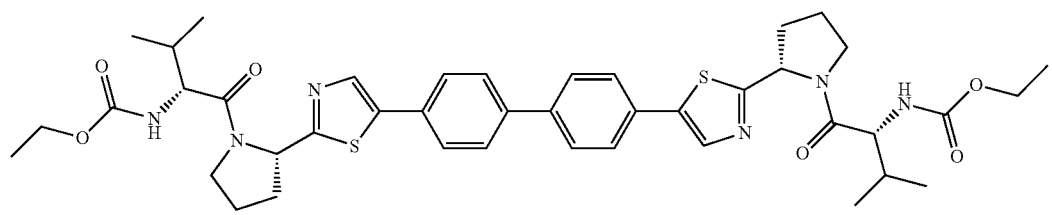
97a
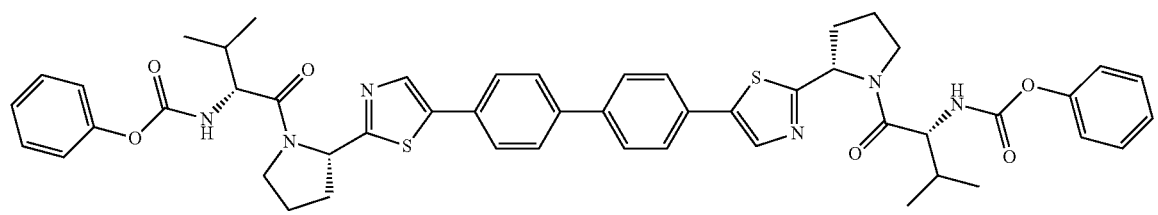
98a
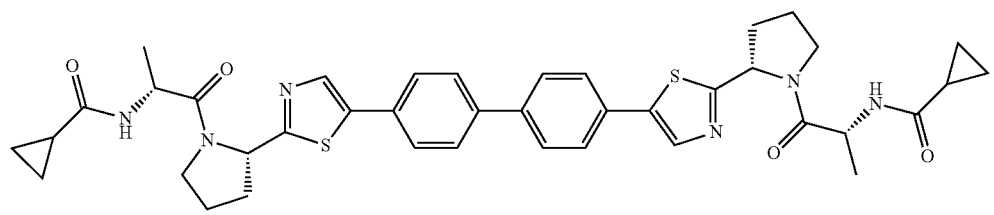

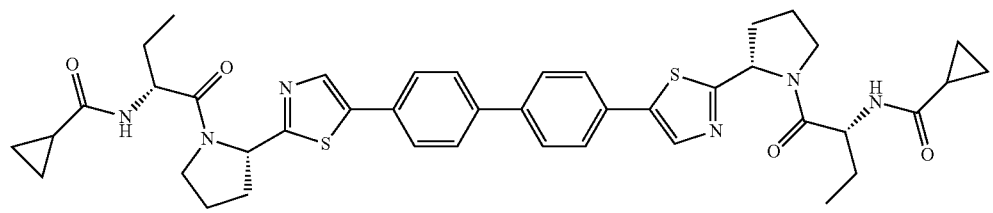
99a
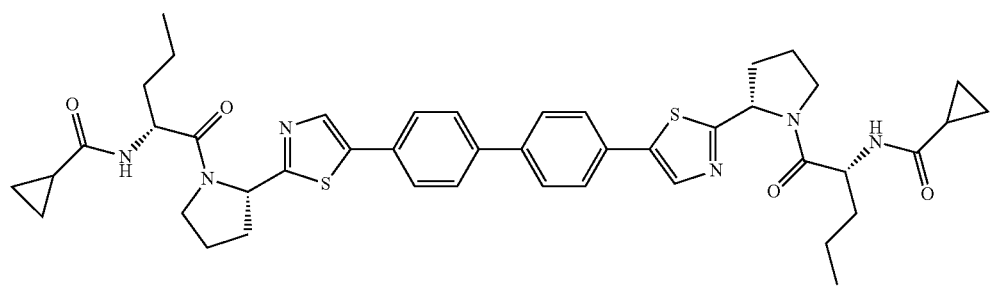
100a
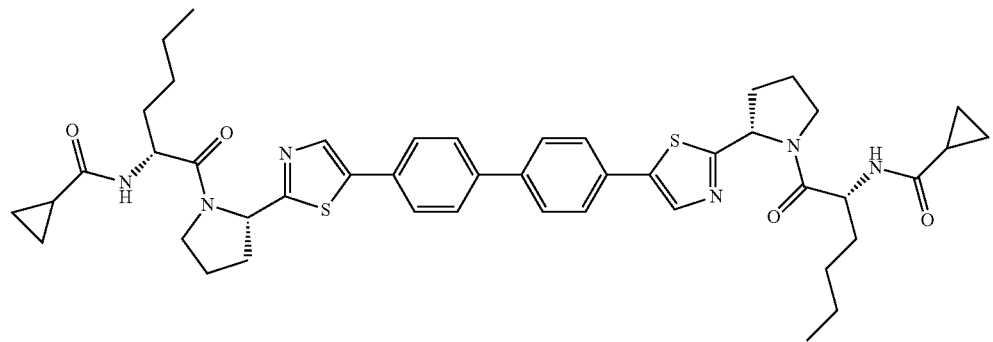
101a
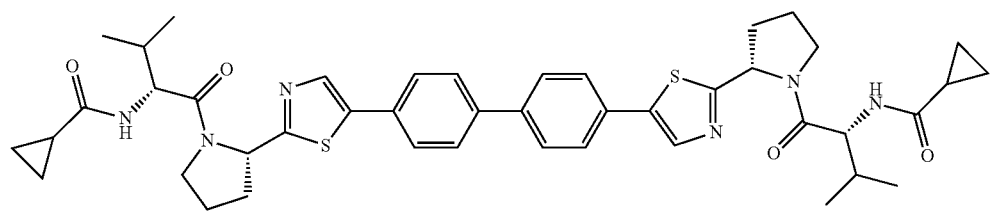
102a
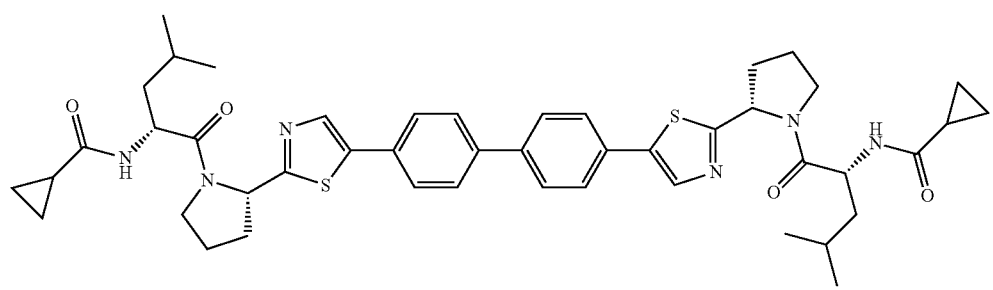
103a -continued
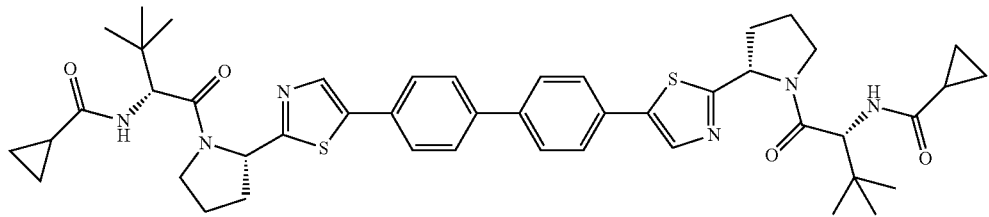
104a
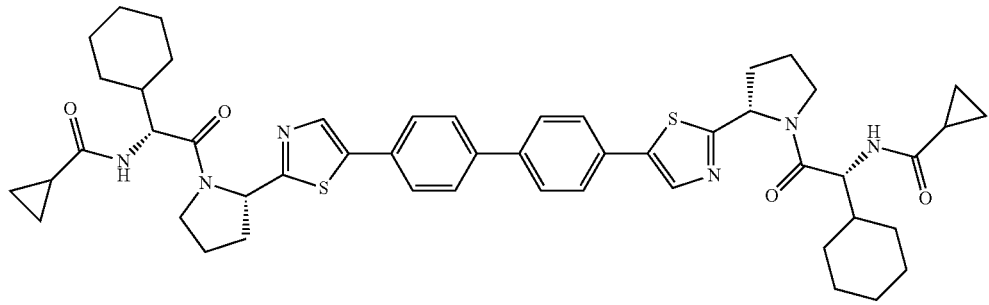
105a
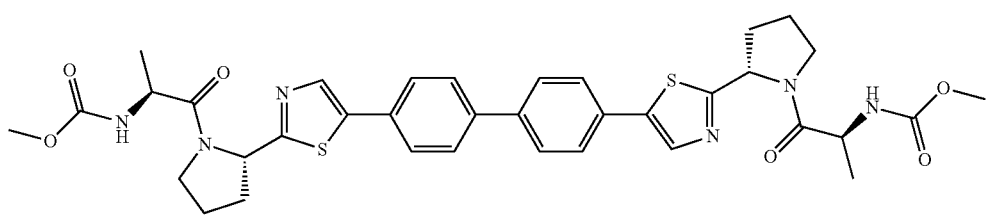
106a
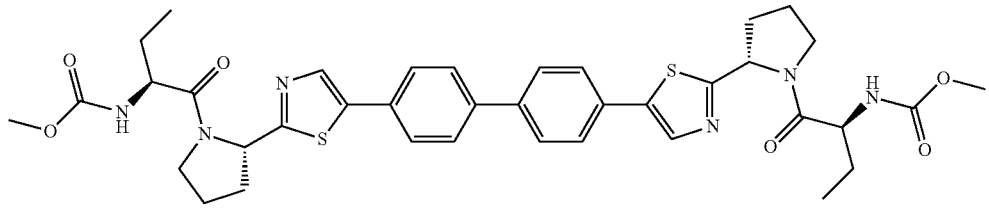
107a
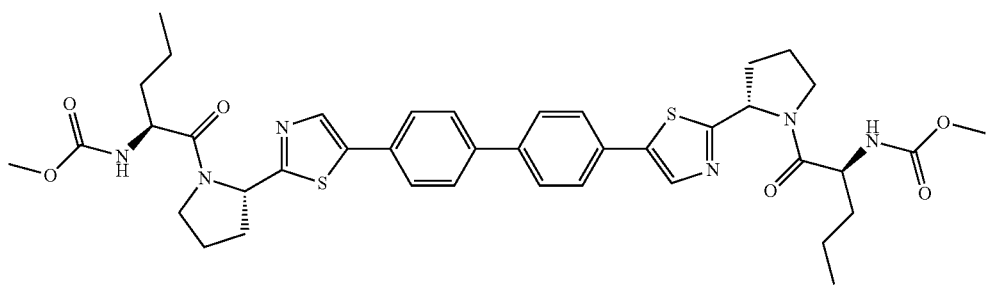
108a
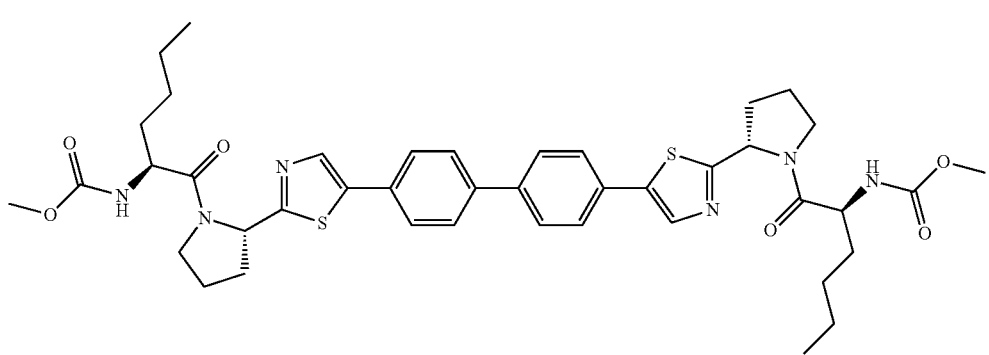
109a -continued
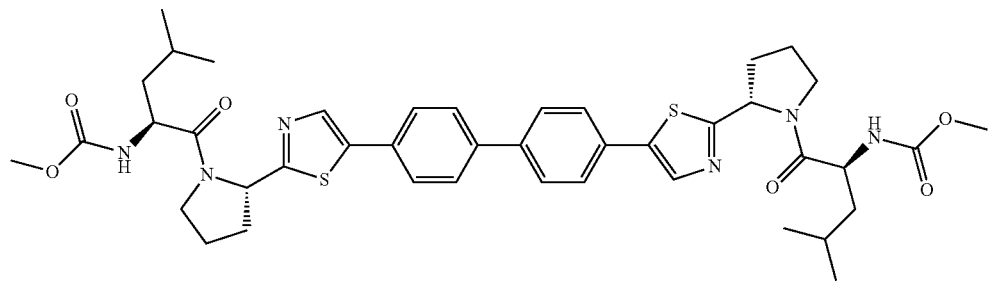
110a
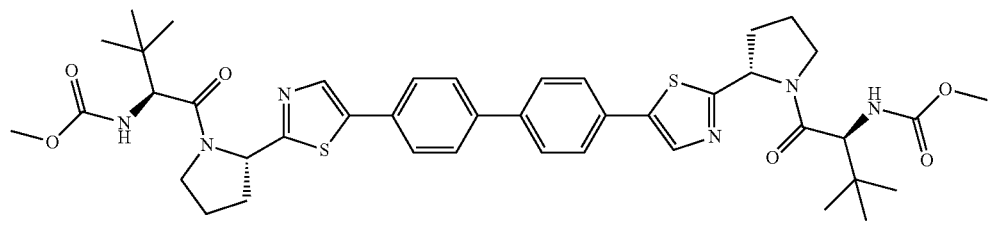
111a
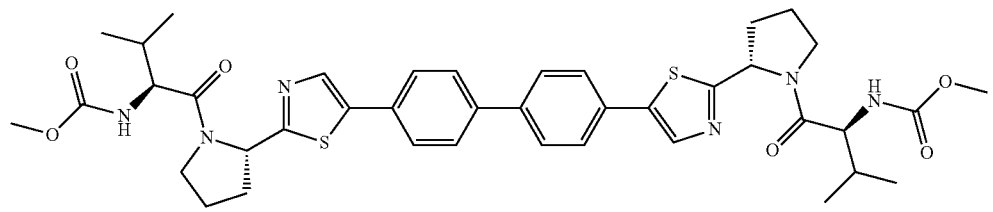
112a
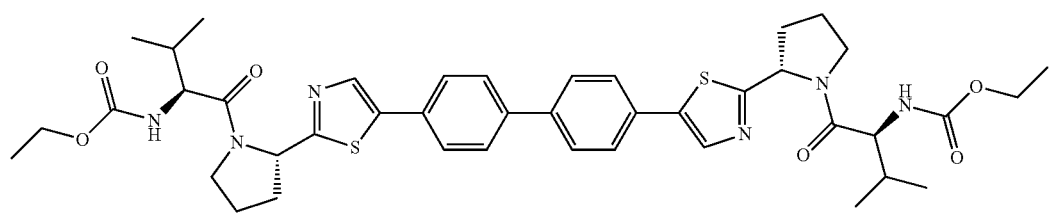
113a
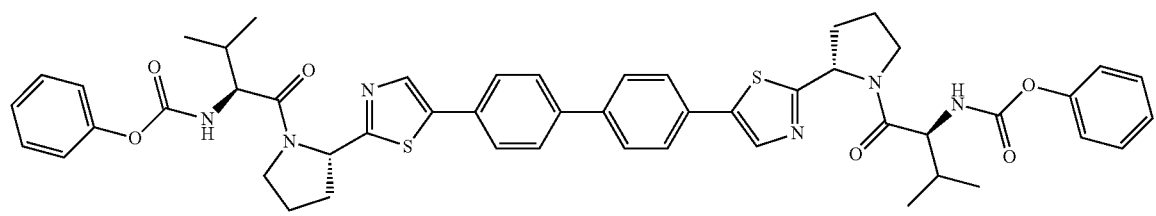
114a
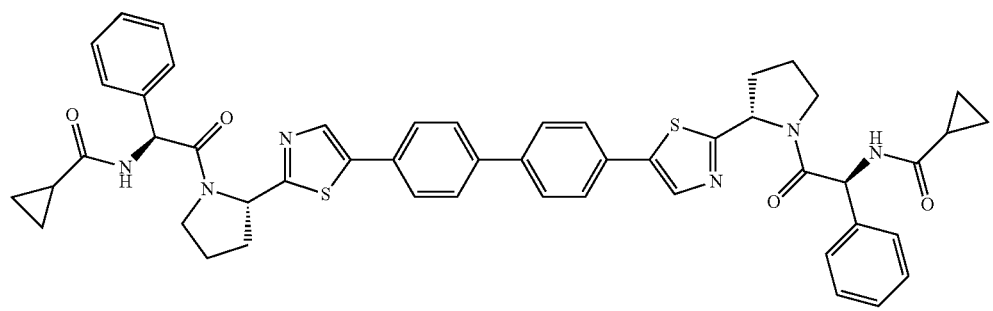
123a

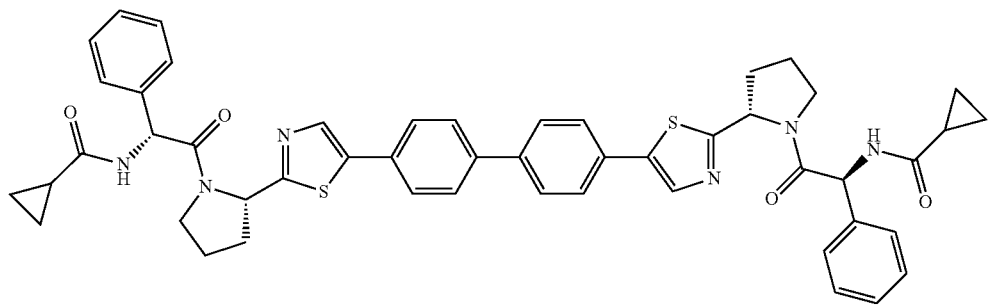
124a
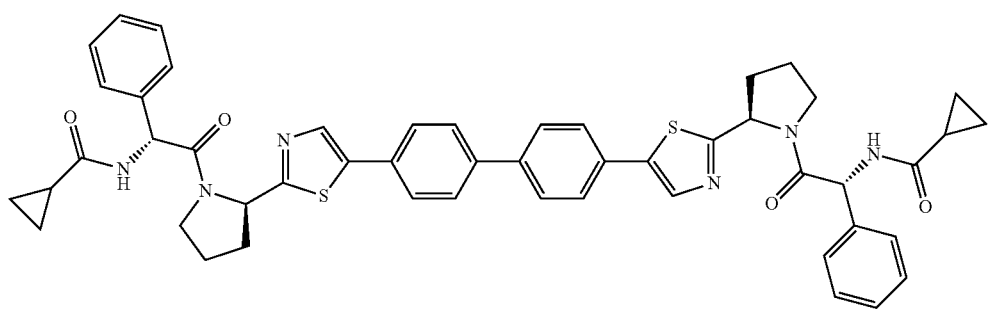
125a
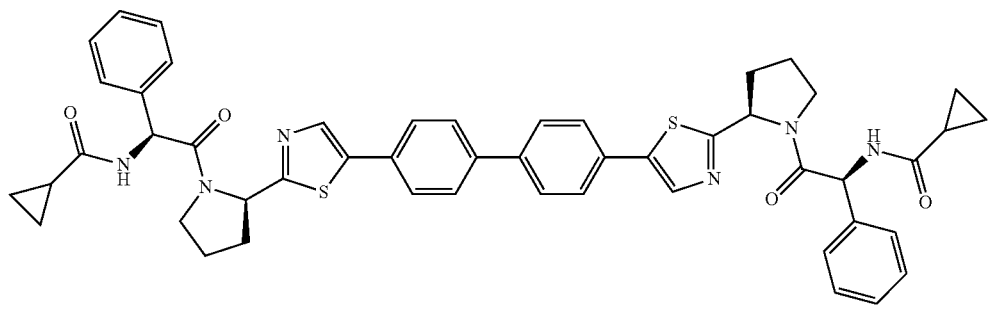
126a
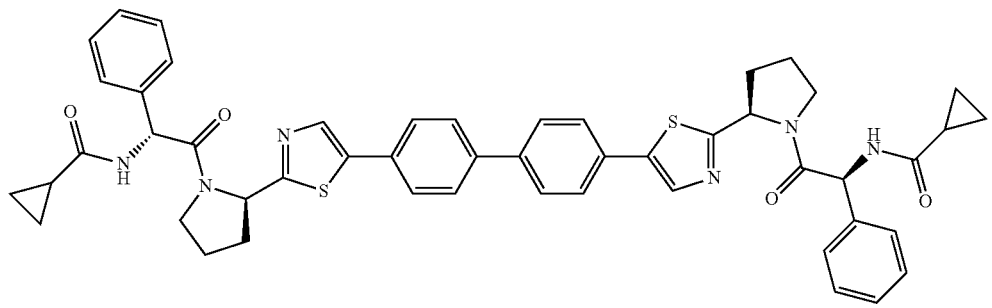
127a
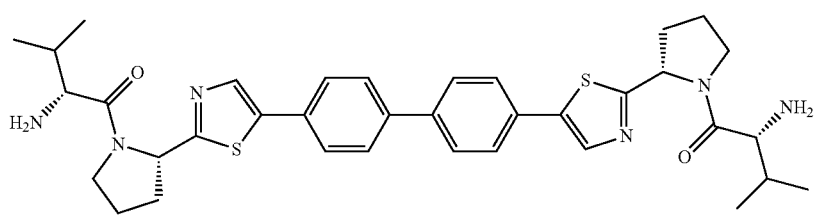
128a -continued
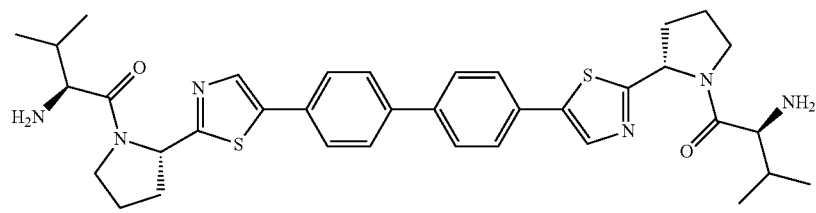
129a
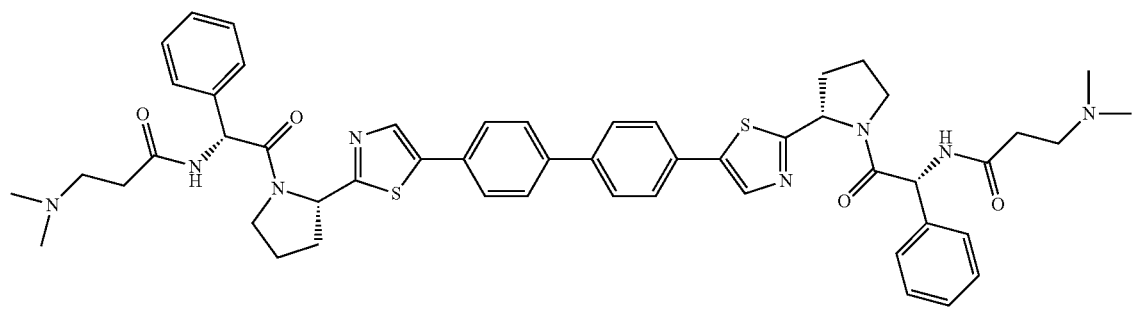
130a
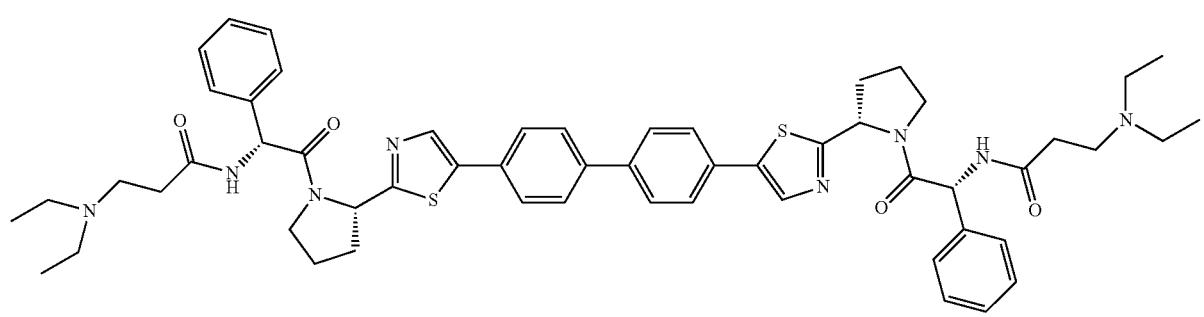
131a
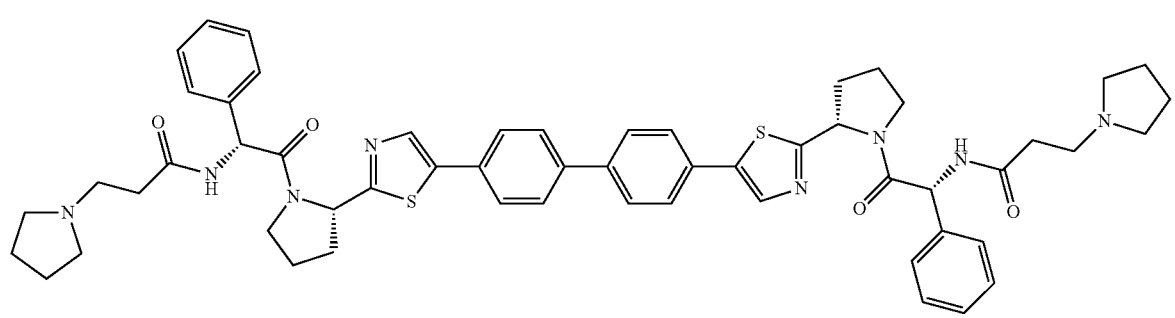
132a
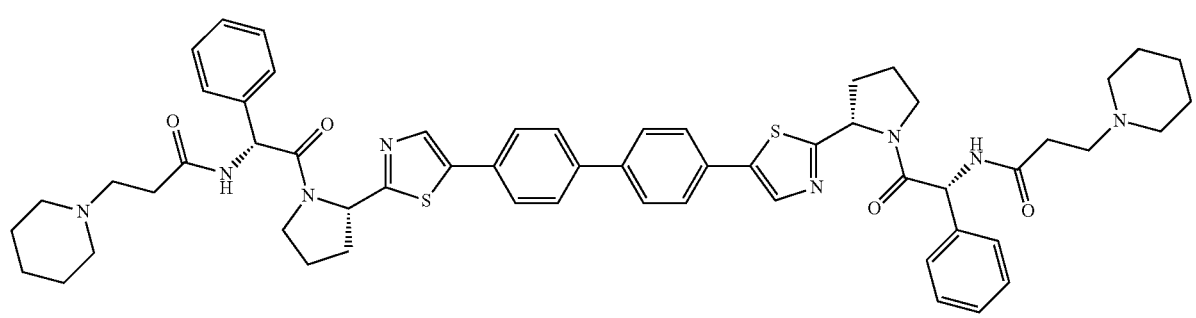
133a -continued
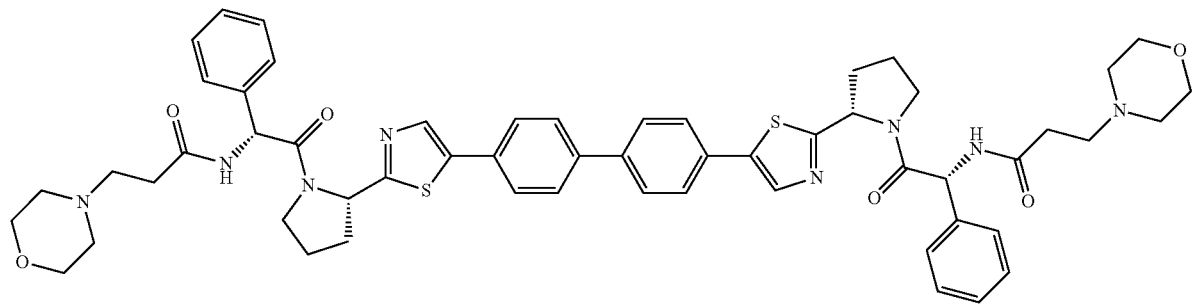
134a
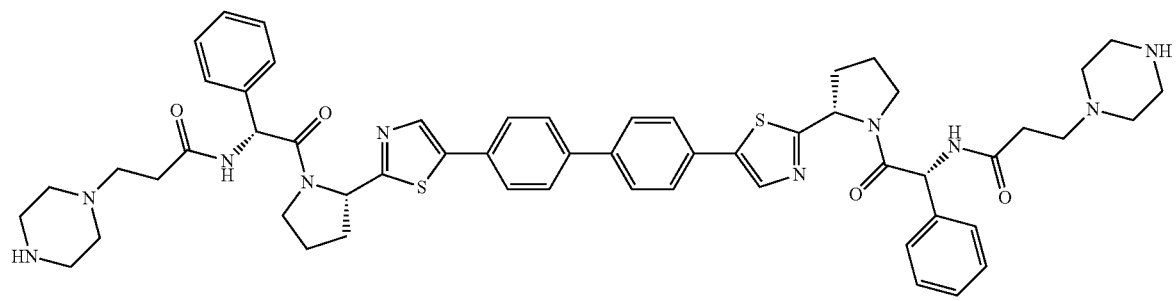
135a
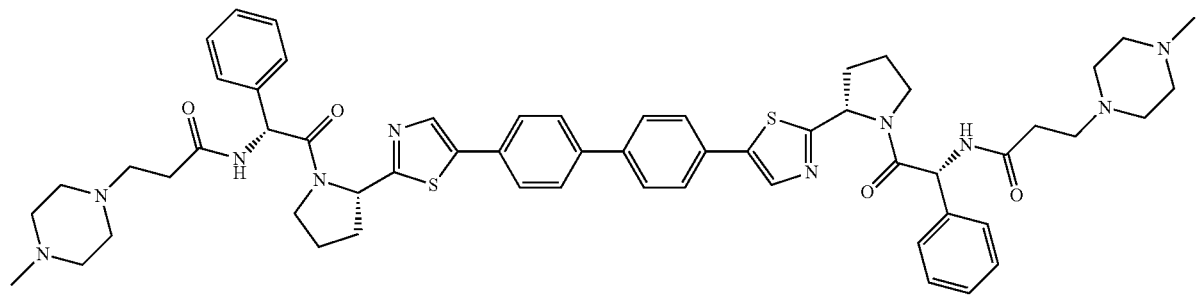
136a
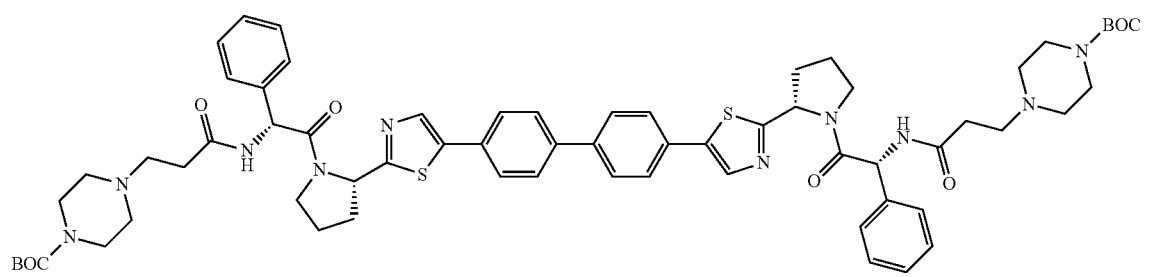
137a
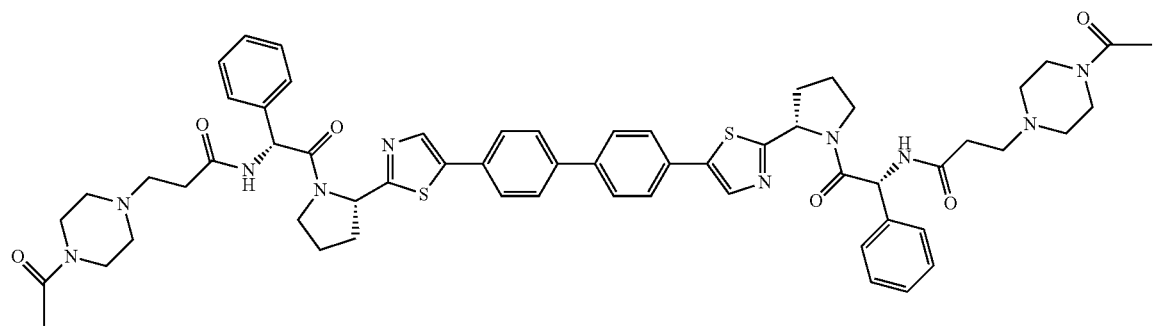
138a -continued
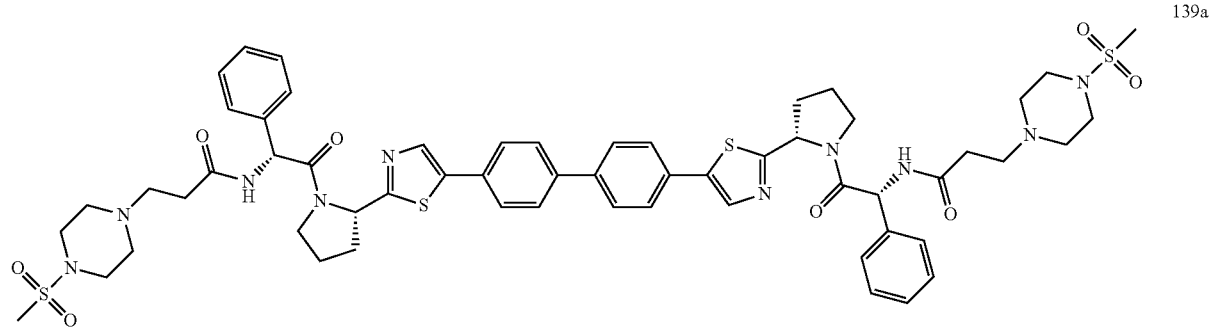
139a
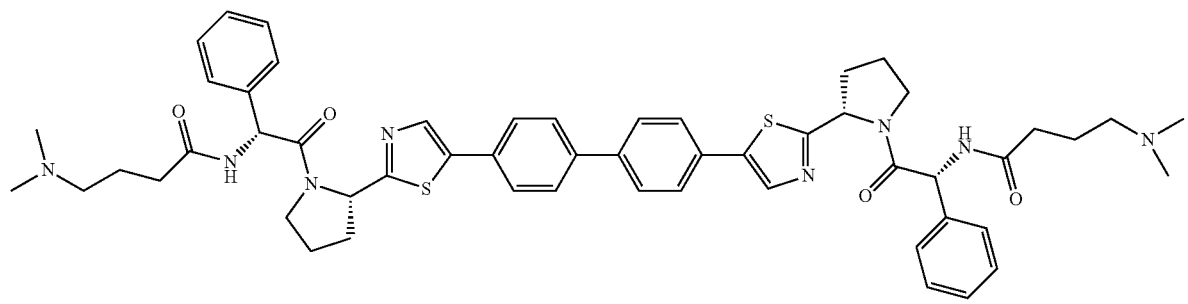
140a
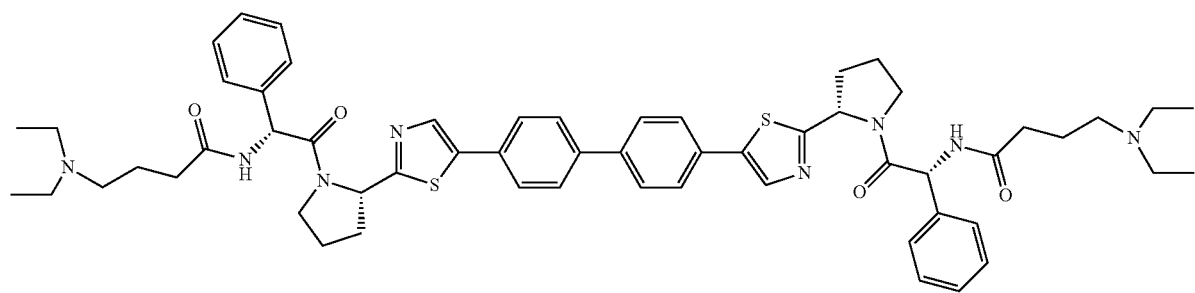
141a
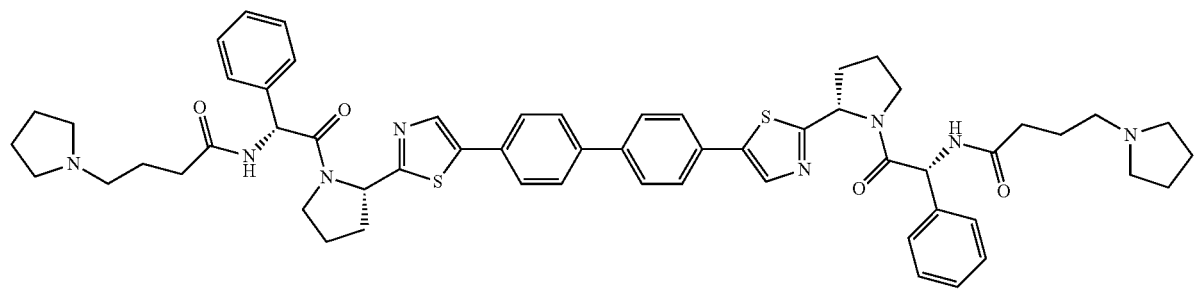
142a
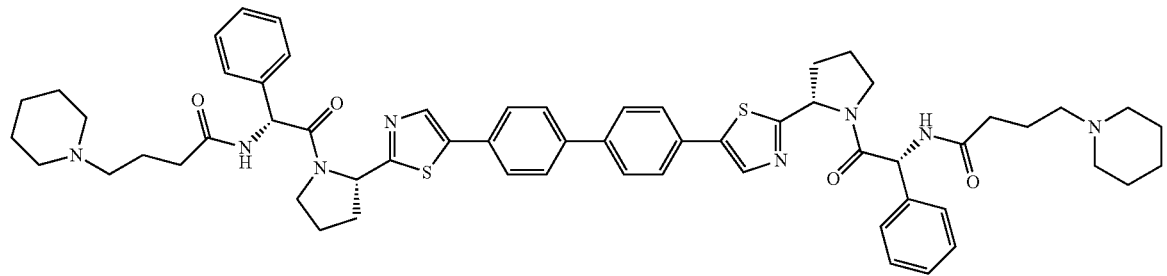
143a -continued
144a
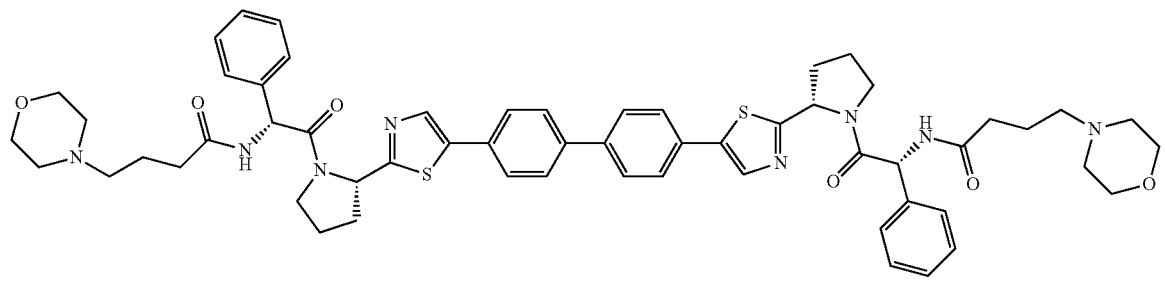
145a
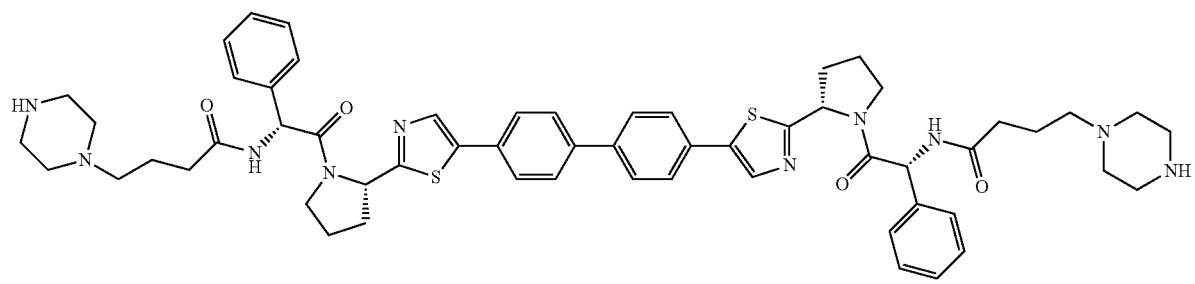
146a
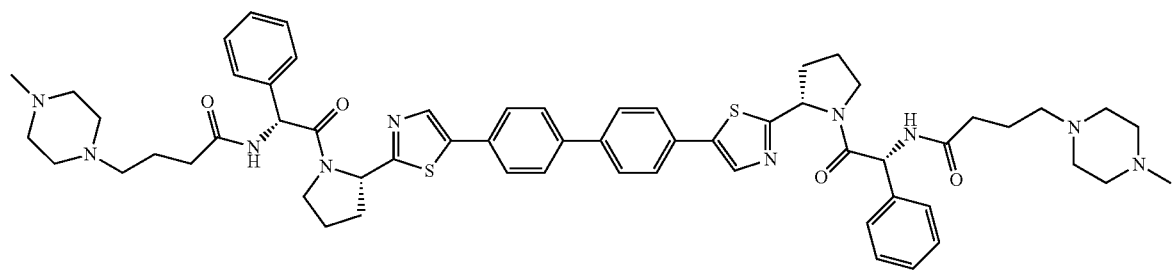
147a
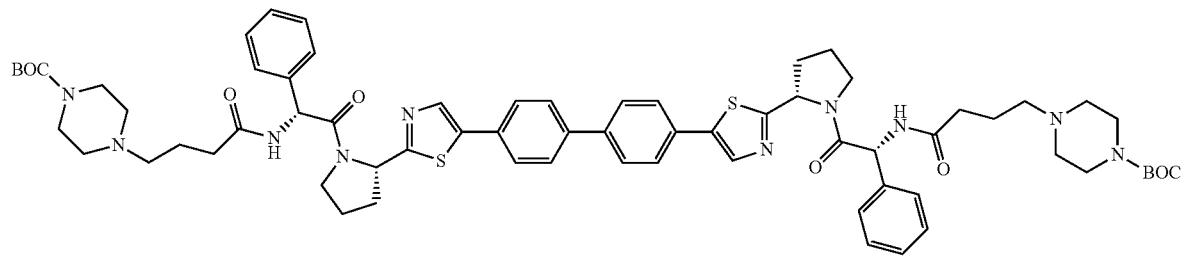
148a
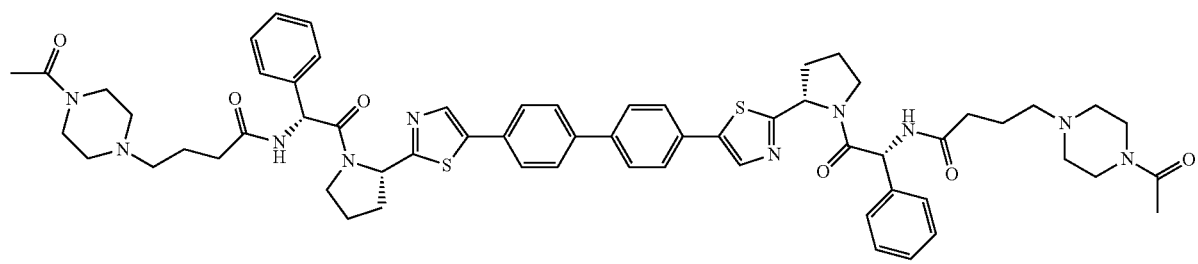

-continued
149a
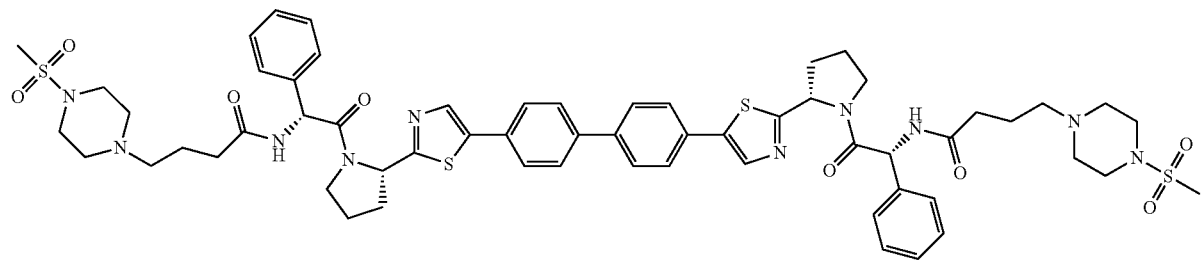
150a
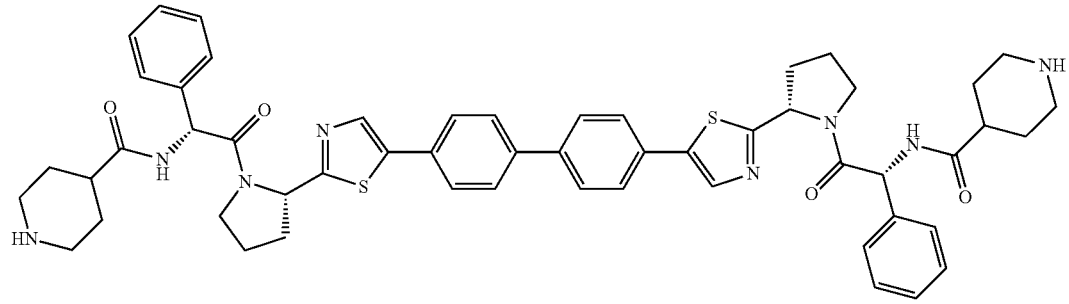
151a
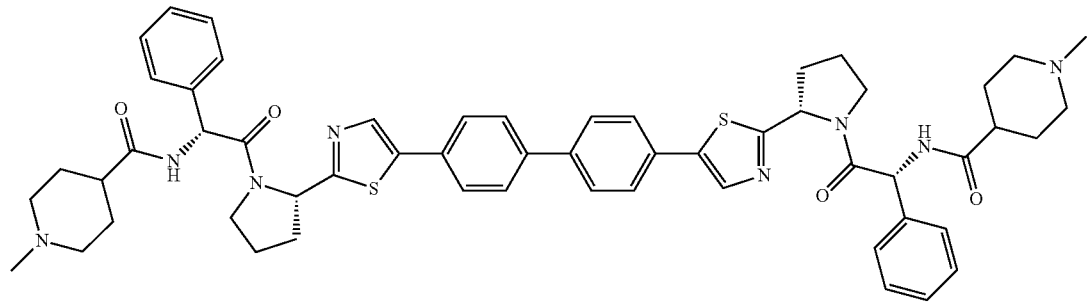
152a
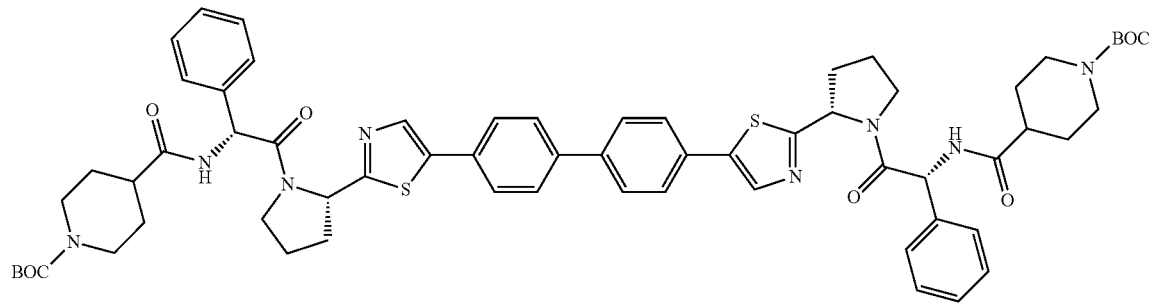
153a
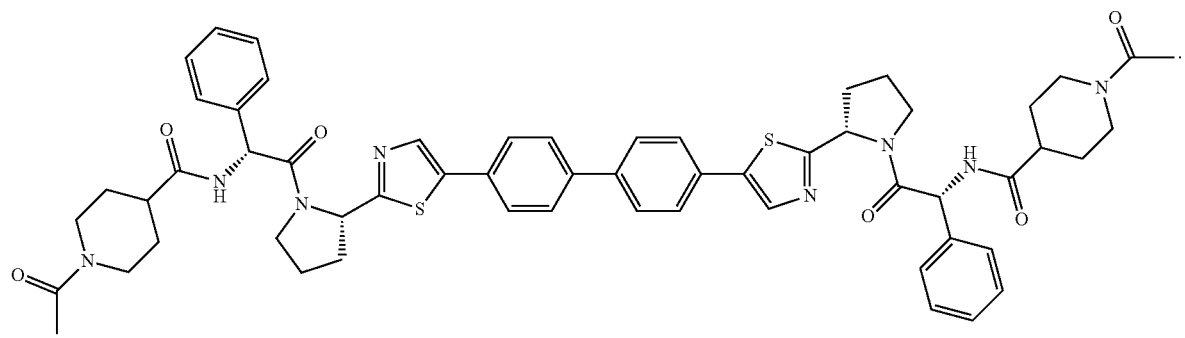

25. A method for treating hepatitis C virus infection, comprising administering to a subject in need thereof an effective amount of a compound of claim 1.

26. A pharmaceutical composition, comprising a compound of claim 1 and a pharmaceutically acceptable carrier.

27. The compound of claim 8, wherein each of $X_1$ and $X_2$ is C(O) and each of $Y_1$ and $Y_2$, independently, is $SO_2$, C(O), or C(O)O.

28. The compound of claim 27, wherein each of $R_7$ and $R_8$ is phenyl.

29. The compound of claim 28, wherein each of $R_{11}$ and $R_{12}$, independently, is $C_{1-5}$ alkyl or $C_{3-5}$ cycloalkyl.

30. The compound of claim 29, wherein each of t and r is 2.

\* \* \* \* \*